(12) United States Patent
Desai et al.

(10) Patent No.: US 7,250,443 B2
(45) Date of Patent: Jul. 31, 2007

(54) PYRROLE BASED INHIBITORS OF GLYCOGEN SYNTHASE KINASE 3

(75) Inventors: Manoj C. Desai, Pleasant Hill, CA (US); Simon Ng, Walnut Creek, CA (US); Zhi-Jie Ni, Fremont, CA (US); Keith B. Pfister, San Ramon, CA (US); Savithri Ramurthy, Walnut Creek, CA (US); Sharadha Subramanian, San Ramon, CA (US); Allan S. Wagman, Belmont, CA (US)

(73) Assignee: Chiron Corporation, Emeryville, CA (US)

( * ) Notice: Subject to any disclaimer, the term of this patent is extended or adjusted under 35 U.S.C. 154(b) by 249 days.

(21) Appl. No.: 10/646,625

(22) Filed: Aug. 21, 2003

(65) Prior Publication Data

US 2004/0077707 A1    Apr. 22, 2004

Related U.S. Application Data

(60) Provisional application No. 60/405,846, filed on Aug. 23, 2002.

(51) Int. Cl.
*A61K 31/4025* (2006.01)
*A61K 31/401* (2006.01)
*C07D 43/02* (2006.01)

(52) U.S. Cl. .................. 514/422; 514/426; 546/279.1; 548/542; 548/557

(58) Field of Classification Search ................ 514/422, 514/426; 546/279.1; 548/542, 557
See application file for complete search history.

(56) References Cited

U.S. PATENT DOCUMENTS 2,488,336 A    11/1949    Scott
3,461,130 A    8/1969    Petersen et al.
3,534,061 A    10/1970    Black
4,985,560 A    1/1991    Sabb et al.

FOREIGN PATENT DOCUMENTS

| WO | WO 97/20821 A1 | 6/1997 |
| WO | WO 99/65897 A1 | 12/1999 |
| WO | WO 01/02409 A1 | 1/2001 |
| WO | WO 01/44206 A1 | 6/2001 |
| WO | WO 01/44246 A1 | 6/2001 |

OTHER PUBLICATIONS

Di Santo, R., et al., "Design, Synthesis and QSAR Studies on N-Aryl Heteroarylisopropanolamines, a New Class of Non-Peptidic HIV-1 Protease Inhibitors," *Bioorganic & Medicinal Chemistry* 10:2511-2526, 2002.

Losada, J., and I. del Peso, "Synthesis, Electrochemical Properties and Electro-Oxidative Polymerization of Copper(II) and Nickel(II) Complexes With N'-Benzoylthiourea Ligands Containing Pyrrole Groups," *Transition Metal Chemistry* 25(1):112-117, 2000.

Naji A., et al., "Electrodeposition of Functionalized Pyrrole (N-[3-(Dimethylpyridyl-2-yl)Aminopropyl], N-(3-Aminopropyl), N-(3-Acetamidopropyl) and N-(2-Cyanoethyl)) on Stainless Steel Gauze for Membrane Preparation," *Journal of Applied Electrochemistry* 31:547-557, 2001.

*Primary Examiner*—Kamal A. Saeed
(74) *Attorney, Agent, or Firm*—Dennis K. Shelton; Alisa A. Harbin

(57) ABSTRACT

New pyrrole based compounds, compositions and methods of inhibiting the activity of glycogen synthase kinase (GSK3) in vitro and of treatment of GSK3 mediated disorders in vivo are provided. The methods, compounds and compositions of the invention may be employed alone, or in combination with other pharmacologically active agents in the treatment of disorders mediated by GSK3 activity, such as diabetes, Alzheimer's disease and other neurodegenerative disorders, obesity, atherosclerotic cardiovascular disease, essential hypertension, polycystic ovary syndrome, syndrome X, ischemia, traumatic brain injury, bipolar disorder, immunodeficiency or cancer.

42 Claims, No Drawings

PYRROLE BASED INHIBITORS OF GLYCOGEN SYNTHASE KINASE 3

CROSS-REFERENCE TO RELATED APPLICATION

This application claims the benefit of U.S. Provisional Application No. 60/405,846, filed Aug. 23, 2002.

FIELD OF THE INVENTION

This invention relates to new pyrrole derivatives that inhibit the activity of glycogen synthase kinase 3 (GSK3), to pharmaceutical compositions containing the compounds and to the use of the compounds and compositions, alone or in combination with other pharmaceutically active agents. The compounds and compositions provided by the present invention have utility in the treatment of disorders mediated by GSK3 activity, such as diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency and cancer.

BACKGROUND OF THE INVENTION

Glycogen synthase kinase 3 (GSK3) is a serine/threonine kinase for which two isoforms, $\alpha$ and $\beta$, have been identified. Woodgett, *Trends Biochem. Sci.*, 16:177-81 (1991). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signaling molecules include IGF-1 and EGF. Saito et al., *Biochem. J.*, 303:27-31 (1994); Welsh et al., *Biochem. J.* 294:625-29 (1993); and Cross et al., *Biochem. J.*, 303:21-26 (1994).

Agents that inhibit GSK3 activity are useful in the treatment of disorders that are mediated by GSK3 activity. In addition, inhibition of GSK3 mimics the activation of growth factor signaling pathways and consequently GSK3 inhibitors are useful in the treatment of diseases in which such pathways are insufficiently active. Examples of diseases that can be treated with GSK3 inhibitors are described below.

Diabetes

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the $\beta$ cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parental route. Since GSK3 inhibition stimulates insulin-dependent processes, it is consequently useful in the treatment of type 1 diabetes.

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30-40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK3 inhibition stimulates insulin-dependent processes and is consequently useful in the treatment of type 2 diabetes. Recent data obtained using lithium salts provides evidence for this notion. The lithium ion has recently been reported to inhibit GSK3 activity. Klein et al., *PNAS* 93:8455-9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK3 activity, possibly because of its documented effects on molecular targets other than GSK3. The purine analog 5-iodotubercidin, also a GSK3 inhibitor, likewise stimulates glycogen synthesis and antagonizes inactivation of glycogen synthase by glucagon and vasopressin in rat liver cells. Fluckiger-Isler et al., *Biochem J* 292:85-91 (1993); and Massillon et al., *Biochem J* 299:123-8 (1994). However, this compound has also been shown to inhibit other serine/threonine and tyrosine kinases. Massillon et al., *Biochem J* 299:123-8 (1994).

One of the main goals in the management of patients with diabetes mellitus is to achieve blood glucose levels as close to normal as possible. In general, obtaining normal postprandial blood glucose levels is more difficult than normalizing fasting hyperglycemia. In addition, some epidemiological studies suggest that postprandial hyperglycemia (PPHG) or hyperinsulinemia are independent risk factors for the development of macrovascular complications of diabetes mellitus. Recently, several drugs with differing pharmacodynamic profiles have been developed which target PPHG. These include insulin lispro, amylin analogues, alpha-glucosidase inhibitors and meglitinide analogues. Insulin lispro has a more rapid onset of action and shorter duration of efficacy compared with regular human insulin. In clinical trials, the use of insulin lispro has been associated with improved control of PPHG and a reduced incidence of hypoglycemic episodes. Repaglinide, a meglitinide analogue, is a short-acting insulinotropic agent which, when given before meals, stimulates endogenous insulin secretions and lowers postprandial hyperglycemic excursions. Both insulin lispro and repaglinide are associated with postprandial hyperinsulinemia. In contrast, amylin analogues reduce PPHG by slowing gastric emptying and delivery of nutrients to the absorbing surface of the gut. Alpha-glucosidase inhibitors such as acarbose, miglitol and voglibose also reduce PPHG primarily by interfering with the carbohydrate-digesting enzymes and delaying glucose absorption. Yamasaki et al., *Tohoku J Exp Med* 1997 November; 183(3):173-83. The GSK inhibitors of the present invention are also useful, alone or in combination with the agents set forth above, in the treatment of postprandial hyperglycemia as well as in the treatment of fasting hyperglycemia.

Alzheimer's Disease

GSK3 is also involved in biological pathways relating to Alzheimer's disease (AD). The characteristic pathological features of AD are extracellular plaques of an abnormally processed form of the amyloid precursor protein (APP), so called β-amyloid peptide (β-AP) and the development of intracellular neurofibrillary tangles containing paired helical filaments (PHF) that consist largely of hyperphosphorylated tau protein. GSK3 is one of a number of kinases that have been found to phosphorylate tau protein in vitro on the abnormal sites characteristic of PHF tau, and is the only kinase also demonstrated to do this in living cells and in animals. Lovestone et al., *Current Biology* 4:1077-86 (1994); and Brownlees et al., *Neuroreport* 8: 3251-3255 (1997). Furthermore, the GSK3 kinase inhibitor, LiCl, blocks tau hyperphosphorylation in cells. Stambolic et al., *Current Biology* 6:1664-8 (1996). Thus GSK3 activity may contribute to the generation of neurofibrillary tangles and consequently to disease progression. Recently it has been shown that GSK3β associates with another key protein in AD pathogenesis, presenillin 1 (PS1). Takashima et al., *PNAS* 95:9637-9641 (1998). Mutations in the PS1 gene lead to increased production of β-AP, but the authors also demonstrate that the mutant PS1 proteins bind more tightly to GSK3β and potentiate the phosphorylation of tau, which is bound to the same region of PS1.

Interestingly it has also been shown that another GSK3 substrate, β-catenin, binds to PS1. Zhong et al., *Nature* 395:698-702 (1998). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSK3β with mutant PS1 may account for the reduced levels of β-catenin that have been observed in the brains of PS1-mutant AD patients and to the disease related increase in neuronal cell-death. Consistent with these observations, it has been shown that injection of GSK3 antisense but not sense, blocks the pathological effects of β-AP on neurons in vitro, resulting in a 24 hr delay in the onset of cell death. Takashima et al., *PNAS* 90:7789-93. (1993). In these latter studies, the effects on cell-death are preceded (within 3-6 hours of β-AP administration) by a doubling of intracellular GSK3 activity, suggesting that in addition to genetic mechanisms may increase GSK3 activity. Further evidence for a role for GSK3 in AD is provided by the observation that the protein expression level (but, in this case, not specific activity) of GSK3 is increased by 50% in postsynaptosomal supernatants of AD vs. normal brain tissue. Pei et al., *J Neuropathol Exp* 56:70-78 (1997).

Even more recently, it has been shown that therapeutic concentrations of lithium, a known GSK3 inhibitor, block the production of β-AP by interfering with amyloid precursor protein (APP) cleavage. Phiel et al., *Nature* 423(22): 435-438 (2003). Since GSK3 also phosphorylates tau protein, the principal component of neurofibrillary tangles, inhibition of GSK3 provides both a reduction in amyloid plaques and neurofibrillary tangles, and is useful in the treatment of Alzheimer's disease.

Other CNS Disorders

In addition to the effects of lithium described above, there is a long history of the use of lithium to treat bipolar disorder (manic depressive syndrome). This clinical response to lithium may reflect an involvement of GSK3 activity in the etiology of bipolar disorder, in which case GSK3 inhibitors could be relevant to that indication. In support of this notion it was recently shown that valproate, another drug commonly used in the treatment of bipolar disorder, is also a GSK3 inhibitor. Chen et al., *J. Neurochemistry* 72:1327-1330 (1999). One mechanism by which lithium and other GSK3 inhibitors may act to treat bipolar disorder is to increase the survival of neurons subjected to aberrantly high levels of excitation induced by the neurotransmitter, glutamate. Nonaka et al., *PNAS* 95: 2642-2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (ALS) and multiple sclerosis (MS). Thomas, *J. Am. Geriatr. Soc.* 43:1279-89 (1995). Consequently GSK3 inhibitors are believed to be a useful treatment in these and other neurodegenerative disorders.

Immune Potentiation

GSK3 phosphorylates transcription factor NF-AT and promotes its export from the nucleus, in opposition to the effect of calcineurin. Beals et al., *Science* 275:1930-33 (1997). Thus, GSK3 blocks early immune response gene activation via NF-AT, and GSK3 inhibitors may tend to permit or prolong activation of immune responses. Thus GSK3 inhibitors are believed to prolong and potentiate the immunostimulatory effects of certain cytokines, and such an effect may enhance the potential of those cytokines for tumor immunotherapy or indeed for immunotherapy in general.

Other Disorders

Lithium also has other biological effects. It is a potent stimulator of hematopoiesis, both in vitro and in vivo. Hammond et al., *Blood* 55: 26-28 (1980). In dogs, lithium carbonate eliminated recurrent neutropenia and normalized other blood cell counts. Doukas et al. *Exp Hematol* 14: 215-221(1986). If these effects of lithium are mediated through the inhibition of GSK3, GSK3 inhibitors may have even broader applications.

Since inhibitors of GSK3 are useful in the treatment of many diseases, the identification of new inhibitors of GSK3 would be highly desirable.

SUMMARY OF THE INVENTION

It has now been surprisingly discovered that glycogen synthase kinase 3 (GSK3) activity can be inhibited in vitro or in vivo by certain pyrrole based derivatives. Accordingly, the present invention provides new compounds, compositions and methods of inhibiting the activity of GSK3 in vitro and of treatment of GSK3 mediated disorders in vivo. In one aspect, the present invention provides new compounds having GSK3 inhibition activity of the following formula (I):

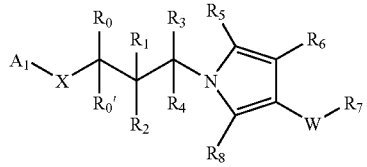

wherein:
X is nitrogen, oxygen, or optionally substituted carbon;
W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;
A$_1$ is optionally substituted aryl, heteroaryl, or a protecting group;
R$_0$ and R$_0$' are independently selected from the group consisting of hydrogen and methyl;
R$_1$, R$_2$, R$_3$, and R$_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;
R$_5$ and R$_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;
R$_6$ is selected from the group consisting of hydrogen, and optionally substituted aryl, heteroaryl, and heterocylo;
R$_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, amino-carbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;
the tautomers thereof;
or a pharmaceutically acceptable salt thereof.

In other preferred embodiments, novel compounds of the invention are provided by the compounds of formula (II):

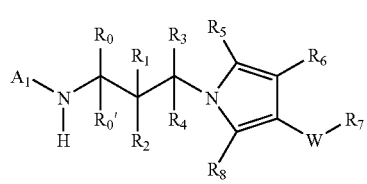

wherein:
W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;
A$_1$ is optionally substituted aryl, heteroaryl, or a protecting group;
R$_0$ and R$_0$' are independently selected from the group consisting of hydrogen and methyl;
R$_1$, R$_2$, R$_3$, and R$_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;
R$_5$ and R$_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;
R$_6$ is selected from the group consisting of hydrogen, and optionally substituted aryl, heteroaryl, and heterocylo;
R$_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, amino-carbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

the tautomers thereof;

or a pharmaceutically acceptable salt thereof.

In yet other particularly preferred embodiments, novel compounds of the invention are provided by the compounds of formula (III):

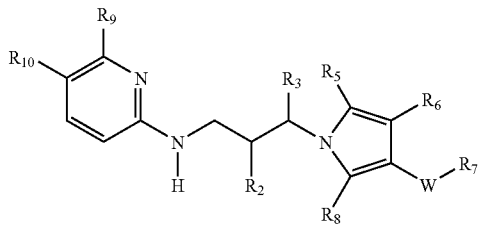

(III)

wherein W is absent or is selected from the group consisting of —O—, —S—, —NH—, —NH—CO—, —CO—, —CO$_2$—, —CH$_2$—, —CF$_2$—, —CONH—, and —NR'—, where R' is alkyl, substituted alkyl, cycloalkyl, aryl, heteroaryl, heterocyclyl;

$R_2$ and $R_3$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkyl-carbonyl, heteroarylcarbonyl, heteroaralkylcarbonyl, aryl and heteroaryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;

$R_6$ is selected from the group consisting of hydrogen, and optionally substituted aryl, heteroaryl, and heterocylo;

$R_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

$R_9$ and $R_{10}$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl; the tautomers thereof; or a pharmaceutically acceptable salt thereof.

The methods, compounds and compositions of the invention may be employed alone, or in combination with other pharmacologically active agents in the treatment of disorders mediated by GSK3 activity, such as in the treatment of diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

DETAILED DESCRIPTION OF THE PREFERRED EMBODIMENT

In accordance with the present invention, compounds, compositions and methods are provided for the inhibition of glycogen synthase kinase 3 (GSK3) activity, either in vitro or in vivo. In one aspect, the present invention provides new compounds having GSK3 inhibition activity of the following formula (I):

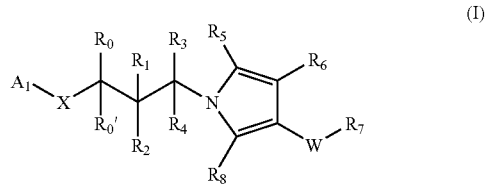

(I)

wherein:

X is nitrogen, oxygen, or optionally substituted carbon;

W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;

$A_1$ is optionally substituted aryl or heteroaryl;

$R_0$ and $R_0'$ are independently selected from the group consisting of hydrogen and methyl;

$R_1$, $R_2$, $R_3$, and $R_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;

$R_6$ is selected from the group consisting of hydrogen, and optionally substituted aryl, heteroaryl, and heterocylo;

$R_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, amino-carbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

the tautomers thereof;

or a pharmaceutically acceptable salt thereof.

In other preferred embodiments, novel compounds of the invention are provided by the compounds of formula (II):

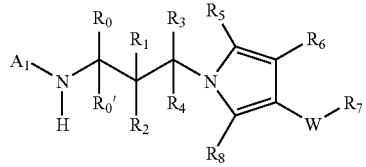

(II)

wherein:

W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;

$A_1$ is optionally substituted aryl, heteroaryl, or a protecting group;

$R_0$ and $R_0'$ are independently selected from the group consisting of hydrogen and methyl;

$R_1$, $R_2$, $R_3$, and $R_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;

$R_6$ is selected from the group consisting of hydrogen, and optionally substituted aryl, heteroaryl, and heterocylo;

$R_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

the tautomers thereof;

or a pharmaceutically acceptable salt thereof.

In yet other particularly preferred embodiments, novel compounds of the invention are provided by the compounds of formula (III):

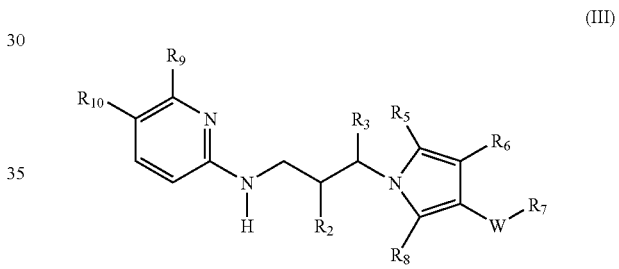

(III)

wherein W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;

$R_2$ and $R_3$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkyl-carbonyl, heteroarylcarbonyl, heteroaralkylcarbonyl, aryl and heteroaryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkyl-carbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heteroarylaryl, heteroarylheteroaryl, heterocycloalkyl, heterocyclo-carbonyloxy, heteroarylcarbonyloxy, and arylsulfonamido;

$R_6$ is selected from the group consisting of hydrogen, and optionally substituted aryl, heteroaryl, and heterocylo;

$R_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, hetero-arylcarbonyl, heteroaralkylcarbonyl, alkylcarbonyloxy, arylcarbonyloxy, aralkyl-carbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, amino-carbonyl, aminoaryl, alkylsulfonyl, sulfonamido, aminoalkoxy, alkylamino, heteroarylamino, alkylcarbonylamino, alkylaminocarbonylamino, arylaminocarbonyl-amino, aralkylcarbonylamino, heteroarylcarbonylamino, arylcarbonylamino, heteroaryl-carbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

$R_9$ and $R_{10}$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxy-pyridyl, methoxynitropyridyl, methoxycyanopyridyl and nitrothiazolyl; the tautomers thereof; or a pharmaceutically acceptable salt thereof.

The constituent $A_1$ (formulas (I) and (II), above) can be an aromatic ring having from 3 to 10 carbon ring atoms and optionally 1 or more ring heteroatoms. Thus, in one embodiment, A can be optionally substituted carbocyclic aryl. Alternatively, A is optionally substituted heteroaryl, such as, for example, substituted or unsubstituted pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, which may substituted with at least one and not more than 3 substitution groups. Representative substitution groups can be independently selected from the group consisting of, for example, nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerhetero-aralkylcarbonyl, alkylthio, aminoalkyl and cyanoalkyl.

In a presently particularly preferred embodiment of the invention, $A_1$ has the formula:

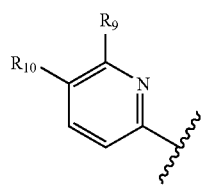

(IV)

wherein $R_9$ and $R_{10}$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkyl-carbonyl, lowerheteroaralkylcarbonyl, alkylthio, aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxy-pyridyl, methoxynitropyridyl, methoxycyanopyridyl and nitrothiazolyl.

In other embodiments of the invention at least one of $R_1$, $R_2$, $R_3$, and $R_4$ may be hydrogen, or unsubstituted or substituted loweralkyl selected from the group consisting of haloloweralkyl, heterocycloaminoalkyl, and loweralkylaminoloweralkyl; or loweralkyl-aminoloweralkyl. Presently preferred embodiments of the invention include compounds wherein $R_1$, $R_2$, and $R_3$ are hydrogen and $R_4$ is selected from the group consisting of hydrogen, methyl, ethyl, aminoethyl, dimethylaminoethyl, pyridylethyl, piperidinyl, pyrrolidinylethyl, piperazinylethyl and morpholinylethyl.

Other presently preferred compounds of the invention include compounds of formula (I) wherein at least one of $R_5$ and $R_7$ is selected from the group consisting of substituted and unsubstituted aryl, heteroaryl and biaryl. In presently preferred embodiments, at least one of $R_5$ and $R_8$ is a substituted or unsubstituted moiety of the formula:

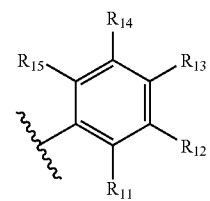

(V)

wherein $R_{11}$, $R_{12}$, $R_{13}$, $R_{14}$, and $R_{15}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkylcarbonylamino, heteroaralkylcarbonylamino, arylcarbonyl-amino, heteroarylcarbonylamino aminocarbonyl, loweralkylaminocarbonyl, amino-aralkyl, loweralkylaminoalkyl, aryl, heteroaryl, cycloheteroalkyl, aralkyl, alkyl-carbonyloxy, arylcarbonyloxy, aralkylcarbonyloxy, arylcarbonyloxyalkyl, alkylcarbonyl-oxyalkyl, heteroarylcarbonyloxyalkyl, aralkycarbonyloxyalkyl, and heteroaralkcarbonyl-oxyalkyl. Presently particularly preferred compounds are obtained wherein $R_{11}$, $R_{12}$, $R_{14}$ and $R_{15}$ are hydrogen and $R_{13}$ is selected from the group consisting of halo, loweralkyl, hydroxy, loweralkoxy, haloloweralkyl, aminocarbonyl, alkylaminocarbonyl and cyano; $R_{11}$, $R_{13}$, and $R_{15}$ are hydrogen and $R_{12}$ and $R_{14}$ are independently selected from the group consisting of halo, loweralkyl, hydroxy, loweralkoxy, haloloweralkyl and cyano; $R_{11}$, $R_{12}$, $R_{14}$, and $R_{15}$ are hydrogen and $R_{13}$ is heteroaryl; $R_{11}$, $R_{12}$, $R_{14}$, and $R_{15}$ are hydrogen and $R_{13}$ is a heterocycloalkyl; and wherein at least one of $R_{11}$, $R_{12}$, $R_{13}$, $R_{14}$, and $R_{15}$ are halo and the remainder of $R_{11}$, $R_{12}$, $R_{13}$, $R_{14}$, and $R_{15}$ are hydrogen.

In some representative embodiments, at least one of $R_5$ and $R_8$ is selected from the group consisting of dichlorophenyl, difluorophenyl, trifluoromethylphenyl, chloro-fluorophenyl, bromochlorophenyl, ethylphenyl, methylchlorophenyl, imidazolylphenyl, cyanophenyl, morphlinophenyl and cyanochlorophenyl.

In other representative embodiments of the invention, $R_6$ is substituted or unsubstituted aryl or heteroaryl, such as, for example, substituted or unsubstituted pyridyl, pyrimidinyl, piperazinyl, thiazolyl, indolyl, imidazolyl, oxadiazolyl, tetrazolyl, pyrazinyl, triazolyl, thienyl, furanyl, quinolinyl, pyrrolyopyridyl, benzothiazolyl, benzopyridyl, benzotriazolyl, and benzimidazolyl. In yet other embodiments, $R_6$ may be a monoketopiperazinyl group having the structure:

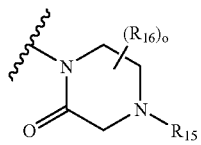

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloarylloweralkyl carbocyclic and heterocyclic; or $R_8$ can be taken with another $R_{16}$ or with $R_{15}$ to form a carbocyclic, heterocyclic or aryl ring; and o is an integer between 1 and 6. In representative embodiments of this aspect of the invention, $R_{15}$ is loweralkyl, such as methyl, ethyl, n-propyl, isopropyl, cyclopropyl, n-butyl, iso-butyl or t-butyl, or $R_{15}$ is taken with $R_{16}$ to form a group having the structure:

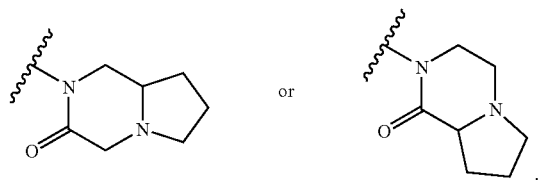

Presently preferred, representative compounds of this group include, for example, the compounds of Examples 1-362, below.

The following abbreviations and definitions are used throughout this application:

"GSK-3" is an abbreviation that stands for glycogen synthase kinase

"AD" is an abbreviation that stands for Alzheimer Disease.

"MS" is an abbreviation that stands for multiple sclerosis.

"ALS" is an abbreviation that stands for amyotropic lateral sclerosis.

"DMAP" is an abbreviation that stands for dimethylaminopropylamine.

"DIC" is an abbreviation that stands for diisopropylcarbodiimide.

"TOSMIC" is an abbreviation that stands for tosylmethyl isocyanide.

"DMSO" is an abbreviation that stands for dimethyl sulfoxide.

"DMF" is an abbreviation that stands for N,N-dimethylformamide.

"DMA" is an abbreviation that stands for N,N-dimethylacetamide.

"TFA" is an abbreviation that stands for trifluoroacetic acid.

"HBTU" is an abbreviation that stands for 2-(1H-benzotriazol-1-yl)-1,3,3-tetramethyluronium hexafluorophospate.

Generally, reference to a certain element such as hydrogen or H is meant to include all isotopes of that element. For example, if an R group is defined to include hydrogen or H, it also includes deuterium and tritium.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above, such as, for example, adamantyl, 3-methyl-1-(methylethyl)cyclopentane, and 2-methylbicyclo[2.2.0]hexane groups. The phrase "alkyl groups" includes primary alkyl groups, secondary alkyl groups, and tertiary alkyl groups. Preferred alkyl groups include straight and branched chain alkyl groups and cyclic alkyl groups having 1 to 12 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, dialkylamine, heterocyclylamine, diheterocyclylamine, (alkyl)(heterocyclyl)amine, or (aryl)(heterocyclyl)amine group.

As used herein, representative heterocyclo groups include, for example, those listed and shown below (where the point of attachment of the substituent group, and the other substituent groups shown below, is through the upper left-hand bond). These heterocyclo groups can be further substituted and may be attached at various positions as will be apparent to those having skill in the organic and medicinal chemistry arts in conjunction with the disclosure herein. Those heterocyclo groups include, for example, pyrrolidine, piperidine, methylpyrrolidine, pyrrolidine-3-ylamine, dimethylpyrrolidin-3-ylamine, 2-aminoquinuclidine, pyrrolidin-2-one, tetrahydrofuranyl, pyrrolidin-3-ol, 4-piperidylpiperidine, 1-benzyl-4-piperidylamine, homopiperidine, homopiperizine, homomorpholine, methylpyrrolidine,

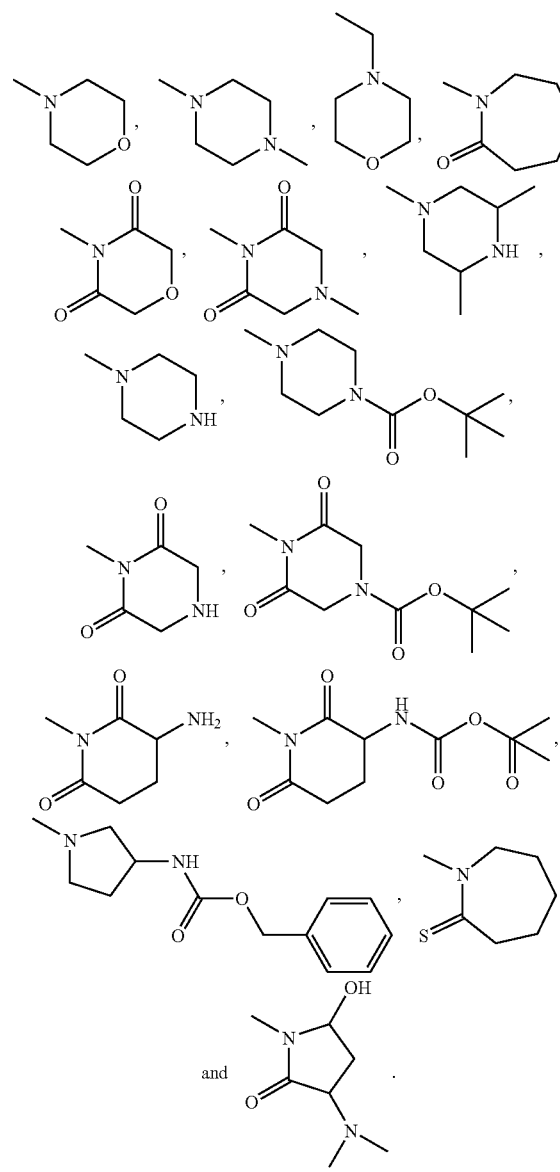

Representative heteroaryl groups include, for example, those shown below. These heteroaryl groups can be further substituted and may be attached at various positions as will be apparent to those having skill in the organic and medicinal chemistry arts in conjunction with the disclosure herein.

Representative cycloimido and heterocycloimido groups include, for example, those shown below. These cycloimido and heterocycloimido can be further substituted and may be attached at various positions as will be apparent to those having skill in the organic and medicinal chemistry arts in conjunction with the disclosure herein.

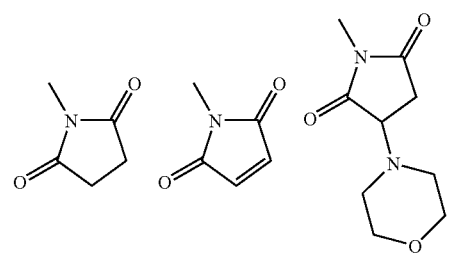

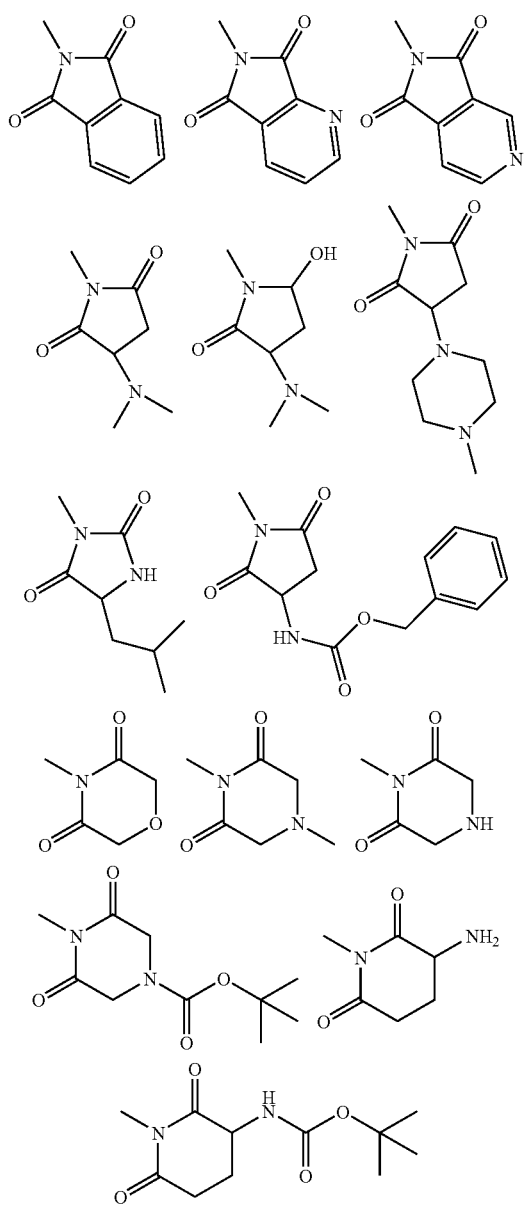

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

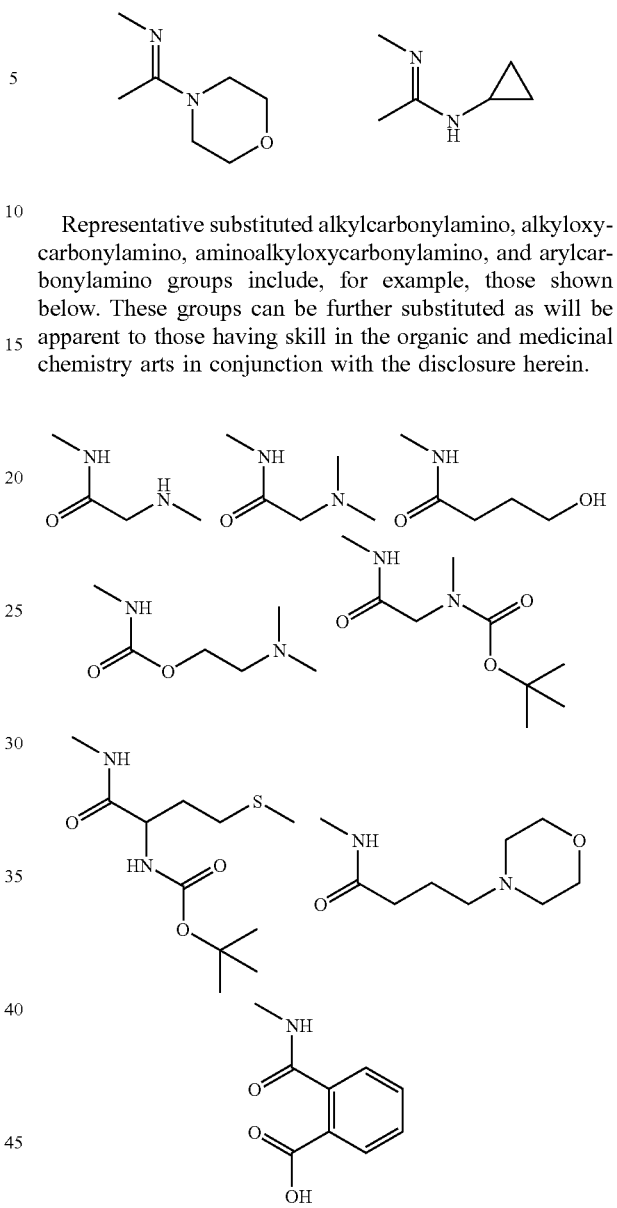

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

Representative substituted aminocarbonyl groups include, for example, those shown below. These can be further substituted by heterocyclo groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropyl-carboxamide, N-(2-hydroxy-isopropyl)carboxamide, methyl 2-carbonylamino-3-hydroxy-propanoate, N-(2-hydroxypropyl)carboxamide, N-(2-hydroxy-isopropyl)carboxamide, N-[2-hydroxy-1-(hydroxymethyl)ethyl]carboxamide, N-(2-carbonylaminoethyl)-acetamide, N-(2-(2-pyridyl)ethyl)carboxamide, N-(2-pyridylmethyl) carboxamide, N-(oxolan-2-ylmethyl)carboxamide, N-(4-hydroxypyrrolidin-2-yl)carboxamide, N-[2-(2-hydroxyethoxy)ethyl]carboxamide, N-(4-hydroxycyclohexyl)carboxamide, N-[2-(2-oxo-4-imidazolinyl)ethyl]carboxamide, N-(carbonylaminomethyl)

acetamide, N-(3-pyrrolidinylpropyl)carboxamide, N-[1-(carbonylaminomethyl)pyrrolidin-3-yl]acetamide, N-(2-morpholin-4-ylethyl)carboxamide, N-[3-(2-oxopyrrolidinyl)propyl]carboxamide, 4-methyl-2-oxopiperazinecarbaldehyde, N-(2-hydroxy-3-pyrrolidinylpropyl)-carboxamide, N-(2-hydroxy-3-morpholin-4-ylpropyl)carboxamide, N-{2-[(5-cyano-2-pyridyl)amino]ethyl}carboxamide, 3-(dimethylamino) pyrrolidinecarbaldehyde, N-[(5-methylpyrazin-2-yl)methyl] carboxamide, 2,2,2-trifluoro-N-(1-formylpyrrolidin-3-yl) acetamide,

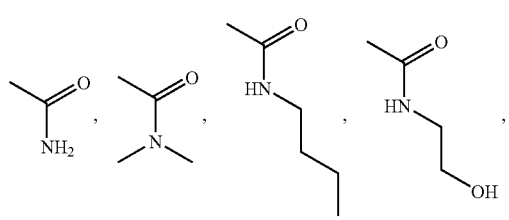

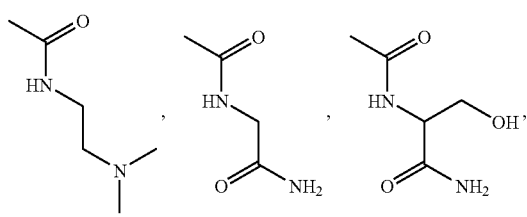

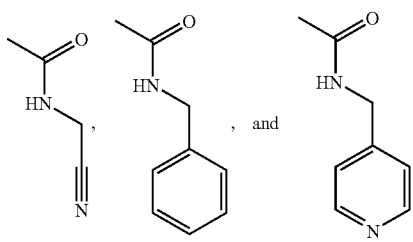

Representative substituted alkoxycarbonyl groups include, for example, those shown below. These alkoxycarbonyl groups can be further substituted as will be apparent to those having skill in the organic and medicinal chemistry arts in conjunction with the disclosure herein.

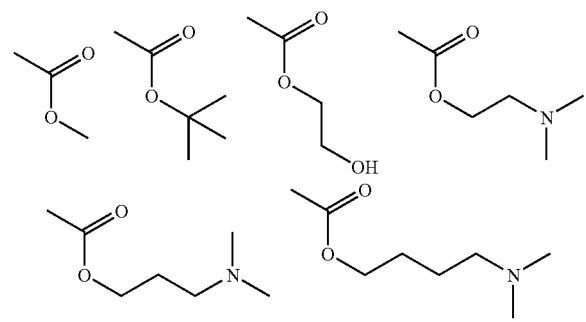

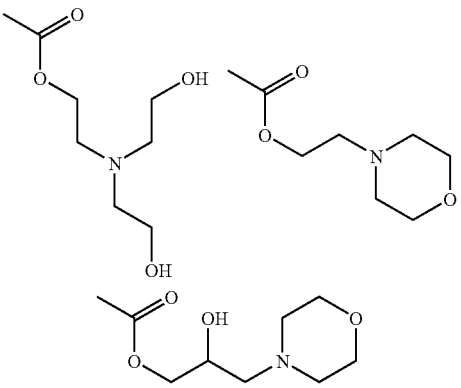

The term "biaryl" refers to a group or substituent to which two aryl groups, which are not condensed to each other, are bound. Exemplary biaryl compounds include, for example, phenylbenzene, diphenyldiazene, 4-methylthio-1-phenyl-benzene, phenoxy-benzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]-acetamide, 1,4-diphenylbenzene, N-[4-(2-phenylethynyl)phenyl]-2-[benzylamino]-acetamide, and 2-amino-N-[4-(2-phenylethynyl)phenyl]propanamide.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl) pyrazine, 2-phenylthiophene, phenylimidazole, 3-(2-piperazinyl-phenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenyl-pyridine, 5-methyl-3-phenylisoxazole, 2-[3-(trifluoromethyl)phenyl] furan, 3-fluoro-5-(2-furyl)-2-methoxy-1-prop-2-enylbenzene, (hydroxyimino)(5-phenyl(2-thienyl))-methane, and 5-[(4-methylpiperazinyl)methyl]-2-phenylthiophene. The term "heteroaryl-heteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))-amine, and dimethyl {2-[2-(5-methylpyrazin-2-yl)ethynyl](4-pyridyl)}amine.

The term "protected" or a "protecting group" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W., John Wiley & Sons, New York, N.Y., (1st Edition, 1981) which can be added or removed using the procedures set forth therein.

Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

In another aspect, the invention provides compositions comprising an amount of a compound of formulas (I), (II) or (III) effective to modulate GSK3 activity in a human or animal subject when administered thereto, together with a pharmaceutically acceptable carrier.

In yet other embodiments, the invention provides methods of inhibiting GSK3 activity in a human or animal subject, comprising administering to the human or animal subject a GSK3 inhibitory amount of a compound of formulas (I), (II) or (III).

The present invention further provides methods of treating human or animal subjects suffering from GSK3-mediated disorder in a human or animal subject, comprising administering to the human or animal subject a therapeutically effective amount of a compound of formulas (I), (II) or (III) above, either alone or in combination with other therapeutically active agents.

In yet other embodiments, the present invention provides compounds of formulas (I), (II) or (III), as described above, for use as a pharmaceutical, as well as methods of use of those compounds in the manufacture of a medicament for the treatment of diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

As used above and elsewhere herein the following terms have the meanings defined below:

"Glycogen synthase kinase 3" and "GSK3" are used interchangeably herein to refer to any protein having more than 60% sequence homology to the amino acids between positions 56 and 340 of the human GSK3 beta amino acid sequence (Genbank Accession No. L33801). To determine the percent homology of two amino acid sequences or of two nucleic acids, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). GSK3 was originally identified by its phosphorylation of glycogen synthase as described in Woodgett et al., *Trends Biochem. Sci.*, 16:177-81 (1991), incorporated herein by reference. By inhibiting GSK3 kinase activity, activities downstream of GSK3 activity may be inhibited, or, alternatively, stimulated. For example, when GSK3 activity is inhibited, glycogen synthase may be activated, resulting in increased glycogen production. GSK3 is also known to act as a kinase in a variety of other contexts, including, for example, phosphorylation of c-jun, β-catenin, and tau protein. It is understood that inhibition of GSK3 kinase activity can lead to a variety of effects in a variety of biological contexts. The invention, however, is not limited by any theories of mechanism as to how the invention works.

"GSK3 inhibitor" is used herein to refer to a compound that exhibits an $IC_{50}$ with respect to GSK3 of no more than about 100 μM and more typically not more than about 50 μM, as measured in the cell-free assay for GSK3 inhibitory activity described generally hereinbelow. "$IC_{50}$" is that concentration of inhibitor which reduces the activity of an enzyme (e.g., GSK3) to half-maximal level. Representative compounds of the present invention have been discovered to exhibit inhibitory activity against GSK3. Compounds of the present invention preferably exhibit an $IC_{50}$ with respect to GSK3 of no more than about 10 μM, more preferably, no more than about 5 μM, even more preferably not more than about 1 μM, and most preferably, not more than about 200 nM, as measured in the cell-free GSK3 kinase assay.

"Optionally substituted" or "substituted or unsubstituted" refers to the replacement of hydrogen with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxy-alkyl, alkylcarbonyl, arylcarbonyl, aralkylcarbonyl, heteroarylcarbonyl, heteroaralkyl-carbonyl, alkylthio, aminoalkyl, cyanoalkyl, and the like.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —$SO_3H$, —$SO_2R$ or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

"Loweralkyl" as used herein refers to branched or straight chain alkyl groups comprising one to ten carbon atoms that are unsubstituted or substituted, e.g., with one or more halogen, hydroxyl or other groups, including, e.g., methyl, ethyl, propyl, isopropyl, n-butyl, t-butyl, neopentyl, trifluoromethyl, pentafluoroethyl and the like.

"Alkylenyl" refers to a divalent straight chain or branched chain saturated aliphatic radical having from 1 to 20 carbon atoms. Typical alkylenyl groups employed in compounds of the present invention are loweralkylenyl groups that have from 1 to about 6 carbon atoms in their backbone. "Alkenyl" refers herein to straight chain, branched, or cyclic radicals having one or more double bonds and from 2 to 20 carbon atoms. "Alkynyl" refers herein to straight chain, branched, or cyclic radicals having one or more triple bonds and from 2 to 20 carbon atoms.

"Loweralkoxy" as used herein refers to RO— wherein R is loweralkyl. Representative examples of loweralkoxy groups include methoxy, ethoxy, t-butoxy, trifluoromethoxy and the like.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Halo" refers herein to a halogen radical, such as fluorine, chlorine, bromine or iodine. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Aryl" refers to monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic" refers herein to fused and non-fused cyclic structures in which at least one cyclic structure is aromatic, such as, for example, benzodioxozolo (which has a heterocyclic structure fused to a phenyl group, i.e.

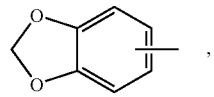

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

"Amino" refers herein to the group —$NH_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "arylcycloalkylamino" refers herein to the group, aryl-cycloalkyl-NH—, where cycloalkyl is a divalent cycloalkyl group. Typically, cycloalkyl has from 3 to 6 backbone atoms, of which, optionally 1 to about 4 are heteroatoms. The term "aminoalkyl" refers to an alkyl group that is terminally substituted with an amino group.

The term "alkoxyalkyl" refers to the group -$alk_1$-O-$alk_2$ where $alk_1$ is alkylenyl or alkenyl, and $alk_2$ is alkyl or alkenyl. The term "loweralkoxyalkyl" refers to an alkoxyalkyl where $alk_1$ is loweralkylenyl or loweralkenyl, and $alk_2$ is loweralkyl or loweralkenyl. The term "aryloxyalkyl" refers to the group -alkylenyl-O-aryl. The term "aralkoxyalkyl" refers to the group -alkylenyl-O-aralkyl, where aralkyl is a loweraralkyl.

The term "alkoxyalkylamino" refers herein to the group —NR-(alkoxylalkyl), where R is typically hydrogen, loweraralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—$NH_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —$S(O)_2$—$NH_2$. "Substituted aminosulfonyl" refers herein to the group —$S(O)_2$—NRR' where R is loweralkyl and R' is hydrogen or a loweralkyl. The term "aralkylaminosulfonlyaryl" refers herein to the group -aryl-$S(O)_2$—NH-aralkyl, where the aralkyl is loweraralkyl.

"Carbonyl" refers to the divalent group —C(O)—.

"Carbonyloxy" refers generally to the group —C(O)—O—R, where R is hydrogen, loweralkyl, cycloalkyl, heterocycloalkyl, amino, aryl, heteroaryl or loweraralkyl. The term "carbonyloxycycloalkyl" refers generally herein to both "carbonyloxycarbocycloalkyl" and "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —$SO_2$—. "Alkylsulfonyl" refers to a substituted sulfonyl of the structure —$SO_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —$SO_2$-aryl. The term "aralkylsulfonyl" refers herein to the group —$SO_2$-aralkyl, in which the aralkyl is loweraralkyl. The term "sulfonamido" refers herein to —$SO_2NH_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl.

As used herein, the term "guanidino" or "guanidyl" refers to moieties derived from guanidine, $(H_2N)$—C(=NH)—$NH_2$. Such moieties include those bonded at the nitrogen atom carrying the formal double bond (the "2"-position of the guanidine, e.g., diaminomethyleneamino, $(H_2N)_2$C=N—) and those bonded at either of the nitrogen atoms carrying a formal single bond (the "1-" and/or "3"-positions of the guandine, e.g., $H_2N$—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=NR)—NR'— (the radical being at the "$N^1$" nitrogen) and R(NR')C=N— (the radical being at the "$N^2$" nitrogen), where R and R' can be hydrogen, loweralkyl, aryl, or loweraralkyl.

Compounds of the present invention can be readily synthesized using the methods described herein, or other methods, which are well known in the art. For example, the synthesis of pyrroles having a wide variety of substituents is comprehensibly reviewed in Blanchette, M. A.; Choy, W.; Davis, J. T.; Essenfeld, A. P.; Masamune, S.; Rousch, W. R.; Sakai, T. *Tet.Let.* 1984,-25, 2183; Have, R.; Leusink, F. R.; van Leusen, A. M. *Synthesis* 1996, 871-876; Mark Trudell, *JOC,* 1997, 62, 2649-2651; and Worrall, D. E. *Org.Synth., Coll. Vol.* 1 .1947, 413-416, which are incorporated herein by reference.

GSK3 inhibitor compounds of the present invention can be purified using known methods, such as, for example, chromatography, crystallization, and the like.

Compounds of the present invention preferably exhibit inhibitory activity that is relatively substantially selective with respect to GSK3, as compared to at least one other type of kinase. As used herein, the term "selective" refers to a relatively greater potency for inhibition against GSK3, as compared to at least one other type of kinase. Preferably, GSK3 inhibitors of the present invention are selective with respect to GSK3, as compared to at least two other types of kinases. Kinase activity assays for kinases other than GSK3 are generally known. See e.g., Havlicek et al., *J. Med. Chem.,* 40:408-12 (1997), incorporated herein by reference. GSK3 selectivity can be quantitated according to the following: GSK3 selectivity=$IC_{50\ (other\ kinase)} \div IC_{50\ (GSK3)}$, where a GSK3 inhibitor is selective for GSK3 when $IC_{50\ (other\ kinase)} > IC_{50\ (GSK3)}$. Thus, an inhibitor that is selective for GSK3 exhibits a GSK3 selectivity of greater than 1-fold with respect to inhibition of a kinase other than GSK3. As used herein, the term "other kinase" refers to a kinase other than GSK3. Such selectivities are generally measured in the cell-free assay described in Example 265.

Typically, GSK3 inhibitors of the present invention exhibit a selectivity of at least about 2-fold (i.e., $IC_{50\ (other\ kinase)} \div IC_{50\ (GSK3)}$) for GSK3, as compared to another kinase and more typically they exhibit a selectivity of at least about 5-fold. Usually, GSK3 inhibitors of the present invention exhibit a selectivity for GSK3, as compared to at least one other kinase, of at least about 10-fold, desirably at least about 100-fold, and more preferably, at least about 1000-fold.

GSK3 inhibitory activity can be readily detected using the assays described herein, as well as assays generally known to those of ordinary skill in the art. Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function by direct interaction with GSK3 itself, or by other mechanisms, including, for example, interference with GSK3 expression or with post-translational processing required to produce mature active GSK3 or alteration of the intracellular localization of GSK3.

In general, a cell-free GSK3 kinase assay can be readily carried out by: (1) incubating GSK3 with a peptide substrate, radiolabeled ATP (such as, for example, $\gamma^{33}P$- or $\gamma^{32}P$-ATP, both available from Amersham, Arlington Heights, Ill.), magnesium ions, and optionally, one or more candidate inhibitors; (2) incubating the mixture for a period of time to allow incorporation of radiolabeled phosphate into the peptide substrate by GSK3 activity; (3) transferring all or a portion of the enzyme reaction mix to a separate vessel, typically a microtiter well that contains a uniform amount of a capture ligand that is capable of binding to an anchor ligand on the peptide substrate; (4) washing to remove unreacted radiolabeled ATP; then (5) quantifying the amount of $^{33}P$ or $^{32}P$ remaining in each well. This amount represents the amount of radiolabeled phosphate incorporated into the peptide substrate. Inhibition is observed as a reduction in the incorporation of radiolabeled phosphate into the peptide substrate.

Suitable peptide substrates for use in the cell free assay may be any peptide, polypeptide or synthetic peptide derivative that can be phosphorylated by GSK3 in the presence of an appropriate amount of ATP. Suitable peptide substrates may be based on portions of the sequences of various natural protein substrates of GSK3, and may also contain N-terminal or C-terminal modifications or extensions including spacer sequences and anchor ligands. Thus, the peptide substrate may reside within a larger polypeptide, or may be an isolated peptide designed for phosphorylation by GSK3.

For example, a peptide substrate can be designed based on a subsequence of the DNA binding protein CREB, such as the SGSG-linked CREB peptide sequence within the CREB DNA binding protein described in Wang et al., *Anal. Biochem.,* 220:397-402 (1994), incorporated herein by reference. In the assay reported by Wang et al., the C-terminal serine in the SXXXS motif of the CREB peptide is enzymatically prephosphorylated by cAMP-dependent protein kinase (PKA), a step which is required to render the N-terminal serine in the motif phosphorylatable by GSK3. As an alternative, a modified CREB peptide substrate can be employed which has the same SXXXS motif and which also contains an N-terminal anchor ligand, but which is synthesized with its C-terminal serine prephosphorylated (such a substrate is available commercially from Chiron Technologies PTY Ltd., Clayton, Australia). Phosphorylation of the second serine in the SXXXS motif during peptide synthesis eliminates the need to enzymatically phosphorylate that residue with PKA as a separate step, and incorporation of an anchor ligand facilitates capture of the peptide substrate after its reaction with GSK3.

Generally, a peptide substrate used for a kinase activity assay may contain one or more sites that are phosphorylatable by GSK3, and one or more other sites that are phosphorylatable by other kinases, but not by GSK3. Thus, these other sites can be prephosphorylated in order to create a motif that is phosphorylatable by GSK3; The term "prephosphorylated" refers herein to the phosphorylation of a substrate peptide with non-radiolabeled phosphate prior to conducting a kinase assay using that substrate peptide. Such prephosphorylation can conveniently be performed during synthesis of the peptide substrate.

The SGSG-linked CREB peptide can be linked to an anchor ligand, such as biotin, where the serine near the C terminus between P and Y is prephosphorylated. As used herein, the term "anchor ligand" refers to a ligand that can be attached to a peptide substrate to facilitate capture of the peptide substrate on a capture ligand, and which functions to hold the peptide substrate in place during wash steps, yet allows removal of unreacted radiolabeled ATP. An exemplary anchor ligand is biotin. The term "capture ligand" refers herein to a molecule which can bind an anchor ligand with high affinity, and which is attached to a solid structure. Examples of bound capture ligands include, for example, avidin- or streptavidin-coated microtiter wells or agarose beads. Beads bearing capture ligands can be further combined with a scintillant to provide a means for detecting captured radiolabeled substrate peptide, or scintillant can be added to the captured peptide in a later step.

The captured radiolabeled peptide substrate can be quantitated in a scintillation counter using known methods. The signal detected in the scintillation counter will be proportional to GSK3 activity if the enzyme reaction has been run under conditions where only a limited portion (e.g., less than 20%) of the peptide substrate is phosphorylated. If an inhibitor is present during the reaction, GSK3 activity will be reduced, and a smaller quantity of radiolabeled phosphate will thus be incorporated into the peptide substrate. Hence, a lower scintillation signal will be detected. Consequently, GSK3 inhibitory activity will be detected as a reduction in scintillation signal, as compared to that observed in a negative control where no inhibitor is present during the reaction. This assay is described in more detail in Example 265 hereinbelow.

A cell-based GSK3 kinase activity assay typically utilizes a cell that can express both GSK3 and a GSK3 substrate, such as, for example, a cell transformed with genes encoding GSK3 and its substrate, including regulatory control sequences for the expression of the genes. In carrying out the cell-based assay, the cell capable of expressing the genes is incubated in the presence of a compound of the present invention. The cell is lysed, and the proportion of the substrate in the phosphorylated form is determined, e.g., by observing its mobility relative to the unphosphorylated form on SDS PAGE or by determining the amount of substrate that is recognized by an antibody specific for the phosphorylated form of the substrate. The amount of phosphorylation of the substrate is an indication of the inhibitory activity of the compound, i.e., inhibition is detected as a decrease in phosphorylation as compared to the assay conducted with no inhibitor present. GSK3 inhibitory activity detected in a cell-based assay may be due, for example, to inhibition of the expression of GSK3 or by inhibition of the kinase activity of GSK3.

Thus, cell-based assays can also be used to specifically assay for activities that are implicated by GSK3 inhibition, such as, for example, inhibition of tau protein phosphorylation, potentiation of insulin signaling, and the like. For example, to assess the capacity of a GSK3 inhibitor to inhibit Alzheimer's-like phosphorylation of microtubule-associated protein tau, cells may be co-transfected with human GSK3β and human tau protein, then incubated with one or more candidate inhibitors. Various mammalian cell lines and expression vectors can be used for this type of assay. For instance, COS cells may be transfected with both a human GSK3β expression plasmid according to the protocol described in Stambolic et al., 1996, *Current Biology* 6:1664-68, which is incorporated herein by reference, and an expression plasmid such as pSG5 that contains human tau protein coding sequence under an early SV40 promoter. See also Goedert et al., *EMBO J.*, 8:393-399 (1989), which is incorporated herein by reference. Alzheimer's-like phosphorylation of tau can be readily detected with a specific antibody such as, for example, AT8, which is available from Polymedco Inc. (Cortlandt Manor, N.Y.) after lysing the cells. This assay is described in greater detail in the examples, hereinbelow.

Likewise, the ability of GSK3 inhibitor compounds to potentiate insulin signaling by activating glycogen synthase can be readily ascertained using a cell-based glycogen synthase activity assay. This assay employs cells that respond to insulin stimulation by increasing glycogen synthase activity, such as the CHO-HIRC cell line, which overexpresses wild-type insulin receptor (~100,000 binding sites/cell). The CHO-HIRC cell line can be generated as described in Moller et al., *J. Biol. Chem.*, 265:14979-14985 (1990) and Moller et al., *Mol. Endocrinol.*, 4:1183-1191 (1990), both of which are incorporated herein by reference. The assay can be carried out by incubating serum-starved CHO-HIRC cells in the presence of various concentrations of compounds of the present invention in the medium, followed by cell lysis at the end of the incubation period. Glycogen synthase activity can be detected in the lysate as described in Thomas et al., *Anal. Biochem.*, 25:486-499 (1968). Glycogen synthase activity is computed for each sample as a percentage of maximal glycogen synthase activity, as described in Thomas et al., *supra*, and is plotted as a function of candidate GSK3 inhibitor concentration. The concentration of candidate GSK3 inhibitor that increased glycogen synthase activity to half of its maximal level (i.e., the $EC_{50}$) can be calculated by fitting a four parameter sigmoidal curve using routine curve fitting methods that are well known to those having ordinary skill in the art. This is described in more detail in Example 266, hereinbelow.

GSK3 inhibitors can be readily screened for in vivo activity such as, for example, using methods that are well known to those having ordinary skill in the art. For example, candidate compounds having potential therapeutic activity in the treatment of type 2 diabetes can be readily identified by detecting a capacity to improve glucose tolerance in animal models of type 2 diabetes. Specifically, the candidate compound can be dosed using any of several routes prior to administration of a glucose bolus in either diabetic mice (e.g. KK, db/db, ob/ob) or diabetic rats (e.g. Zucker Fa/Fa or GK). Following administration of the candidate compound and glucose, blood samples are removed at preselected time intervals and evaluated for serum glucose and insulin levels. Improved disposal of glucose in the absence of elevated secretion levels of endogenous insulin can be considered as insulin sensitization and can be indicative of compound efficacy. A detailed description of this assay is provided in the examples, hereinbelow.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, and the like.

In accordance with other embodiments of the present invention, there is provided a composition comprising GSK3-inhibitor compound of the present invention, together with a pharmaceutically acceptable carrier or excipient.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing GSK-3 inhibitor compounds of the present invention may be in any form suitable for the intended method of administration, including, for example, a solution, a suspension, or an emulsion.

Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

In accordance with yet other embodiments, the present invention provides methods for inhibiting GSK3 activity in a human or animal subject, said method comprising administering to a subject an amount of a GSK3 inhibitor compound having the structure (I), (II) or (III) (or tautomers thereof or compositions comprising such compound) effective to inhibit GSK3 activity in the subject. Other embodiments provided methods for treating a cell or a GSK3-mediated disorder in a human or animal subject, comprising administering to the cell or to the human or animal subject an amount of a compound or composition of the invention effective to inhibit GSK3 activity in the cell or subject. Preferably, the subject will be a human or non-human animal subject. Inhibition of GSK3 activity includes detectable suppression of GSK3 activity either as compared to a control or as compared to expected GSK3 activity.

Effective amounts of the compounds of the invention generally include any amount sufficient to detectably inhibit GSK3 activity by any of the assays described herein, by other GSK3 kinase activity assays known to those having ordinary skill in the art or by detecting an alleviation of symptoms in a subject afflicted with a GSK3-mediated disorder.

GSK3-mediated disorders that may be treated in accordance with the invention include any biological or medical disorder in which GSK3 activity is implicated or in which the inhibition of GSK3 potentiates signaling through a pathway that is characteristically defective in the disease to be treated. The condition or disorder may either be caused or characterized by abnormal GSK3 activity. Representative GSK3-mediated disorders include, for example, type 2 diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency, cancer and the like.

Successful treatment of a subject in accordance with the invention may result in the inducement of a reduction or alleviation of symptoms in a subject afflicted with a medical or biological disorder to, for example, halt the further progression of the disorder, or the prevention of the disorder. Thus, for example, treatment of diabetes can result in a reduction in glucose or HbA1c levels in the patient. Likewise, treatment of Alzheimer's disease can result in a reduction in rate of disease progression, detected, for example, by measuring a reduction in the rate of increase of dementia.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be from about 0.1 mg/kg/day to about 100 mg/kg/day, preferably from about 1 mg/kg/day to about 20 mg/kg/day, and most preferably from about 2 mg/kg/day to about 10 mg/kg/day of a GSK3 inhibitor compound of the present invention, which may be administered in one or multiple doses.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of type 2 diabetes include, for example, insulin, troglitazone, rosiglitazone, pioglitazone, glipizide, metformin, sulfonylurea, acarbose, and the like. Representative agents useful in combination with the compounds of the invention for the treatment of Alzheimer's disease include, for example, donepezil, tacrine and the like. Representative agents useful in combination with the compounds of the invention for the treatment of bipolar disease include, for example, lithium salts, valproate, carbamazepine and the like. A representative agent useful in combination with the compounds of the invention for the treatment of stroke is, for example, tissue plasminogen activator.

When additional active agents are used in combination with the compounds of the present invention, the additional active agents may generally be employed in therapeutic amounts as indicated in the PHYSICIANS' DESK REFERENCE (PDR) 53$^{rd}$ Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The foregoing and other aspects of the invention may be better understood in connection with the following representative examples.

EXAMPLES
Example 1
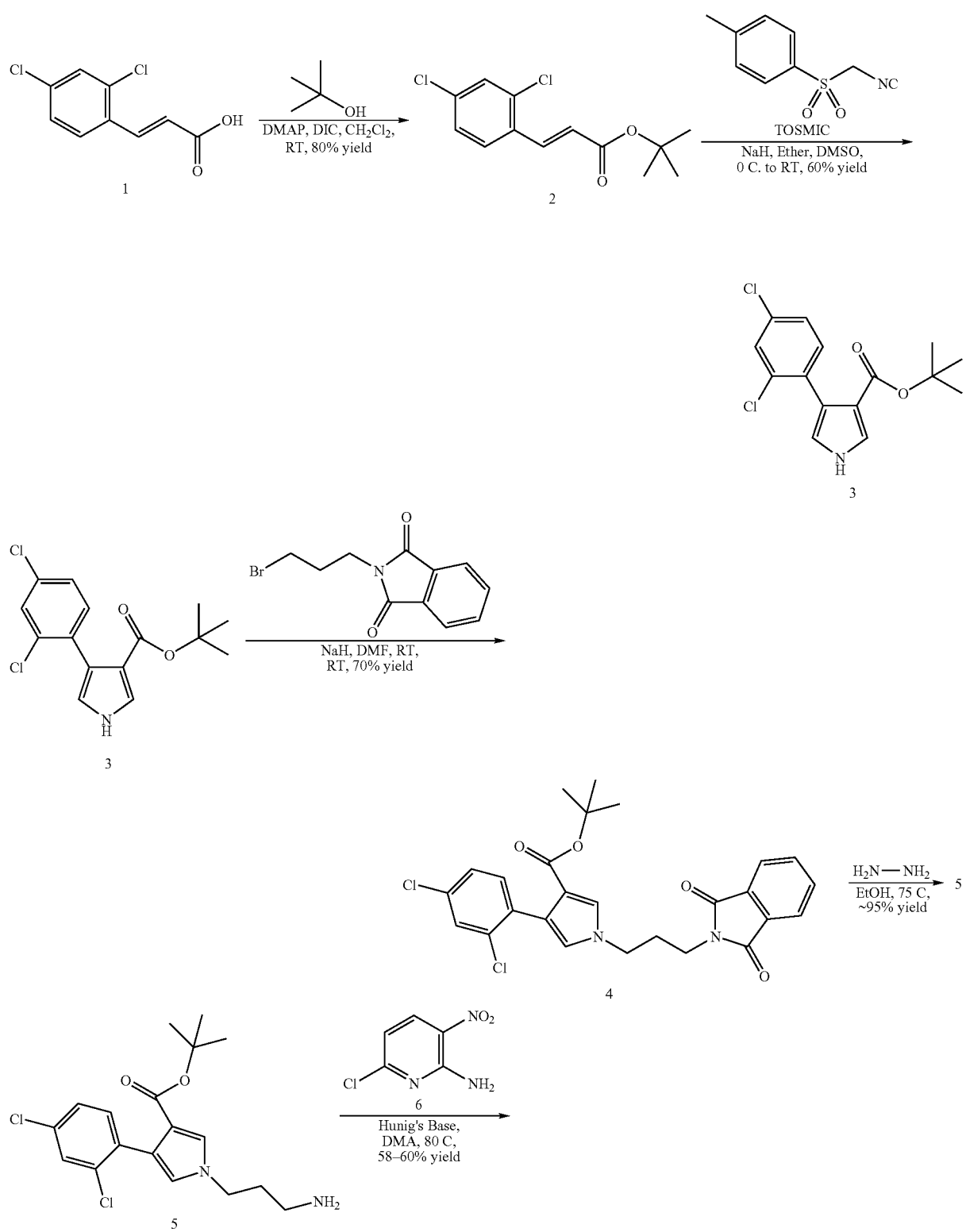
SYNTHESIS OF PYRROLE

-continued

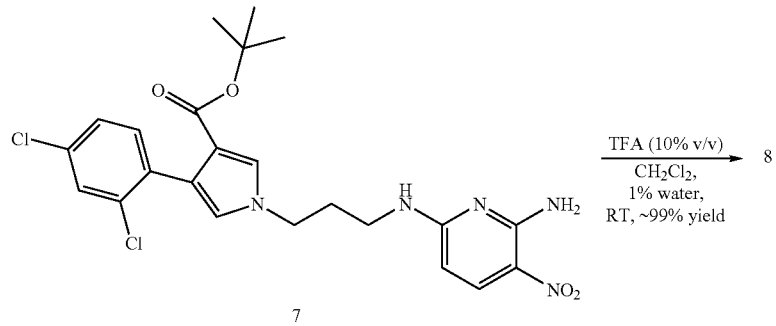

7

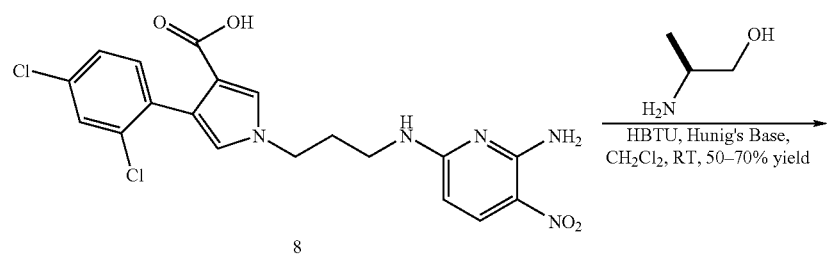

8

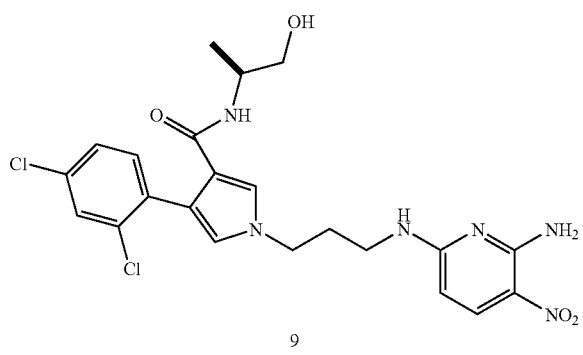

9
Purified by preparative HPLC
CHIR 154703

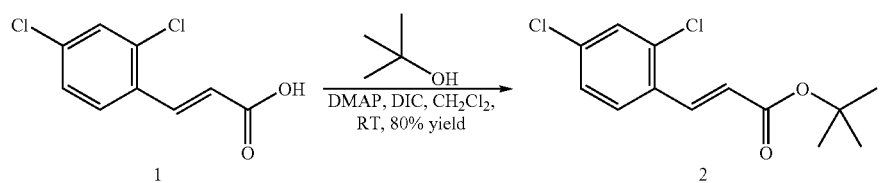

Preparation of tert-butyl (2E)-3-(2,4-dichlorophenyl)prop-2-enoate (2)

Neat DIC (1.4 eq) was added to a well stirred solution of cinnamate (1 eq), t-butyl alcohol (4 eq), DMAP (1.4 eq) and CH$_2$Cl$_2$ under argon at rt. (Note—The cinnamate must be completely in solution which may require gentle warning. Allow the solution to cool to room temperature before adding the DIC. To avoid an exotherm on larger scales, it may be prudent to dilute the DIC with CH$_2$Cl$_2$ before the addition and have an ice bath ready.) After stirring for 8 hours, the reaction develops a white precipitate. The reaction may be monitored by TLC eluting with 25% EtOAc/Hexane (R$_f$ of product was 0.9). The entire reaction was loaded into a separatory funnel (washing with CH$_2$Cl$_2$). The organic mixture was washed with citrate, sat. aq. NaHCO$_3$, water, and brine. The organic layer was dried (Na$_2$SO$_4$), filtered, and concentrated to dryness to give the crude product as an oil. The crude oil was mixed with hexane and stirred for 30 min. The precipitate which forms was filtered over celite and the filtrate was evaporated. The hexane mixture was loaded onto a filter plug of silica and eluted with EtOAc/hexane (97:2 v/v). The first eluted UV active fractions are collected and evaporated to give >99% pure 2 (75-80% yields).

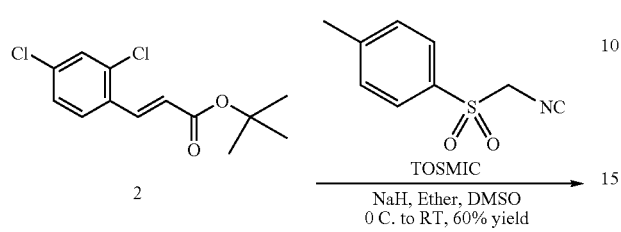

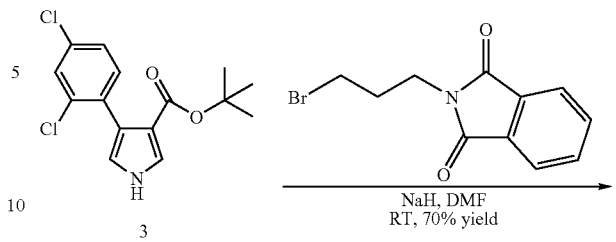

Preparation of tert-butyl 4-(2,4-dichlorophenyl)pyrrole-3-carboxylate (3)

Dry ether was added to NaH (1.5 eq as the oil dispersion) under argon. After decanting off the ether via syringe, the NaH was suspended again with fresh ether under argon. A solution of TOSMIC (1.1 eq) and 2 (1 eq) dissolved in a mixture of ether and DMSO was added dropwise to the stirred suspension of NaH at 0° C. over 20-30 min. The addition was mildly exothermic and evolved gas. After the addition, the reaction was allowed to warm to ambient rt. The progress of the reaction was followed by TLC (25% EtOAc/Hexane, the UV active product was at $R_f$=0.4) and LCMS until done (~2-3 h). Upon completion, the reaction was carefully quenched with sat. aq. NH$_4$Cl (added slowly to avoid strong gas evolution and exotherm) and diluted with ether. The layers were separated and the organic phase was washed with sat. aq. NaHCO$_3$, water, and brine. The crude dark solid can be purified by recrystallization. Best results were achieved either through recrystallization directly from a mixture of hot EtOAc/hexane (1:3 v/v) or by dissolving the crude product in minimal hot EtOAc followed by addition of hexane (~2 volumes of hexane based on the volume of EtOAc). The hot solutions were allowed to cool to room temperature and age over night. The crystals were first filtered and then washed with hexane giving 99% pure product in 60-70% yield.

Preparation f tert-butyl 4-(2,4-dichlorophenyl)-1-[3-(1,3-diox benzo [c]azolin-2-yl)propyl]pyrrole-3-carboxylate (4)

Solid NaH (1.5 eq as the oil dispersion) was added in small portions to a solution of pyrrole 3 (1 eq) and 3-bromopropyl phthalimide (1.2 eq) dissolved in DMF stirred at room temperature and flushed with argon. NOTE—Some gas evolves, but the temperature does not seem to rise above 40-50° C. The reaction was stirred for 1.5 h at room temperature under argon. The reaction was followed by TLC (CH$_2$Cl$_2$/acetonitrile (95:5 v/v), the UV active product was at $R_f$=0.5) and LCMS. Upon completion, the reaction was quenched with sat. aq. NH$_4$Cl (add slowly to avoid strong gas evolution and exotherm). Sat. aq. NaHCO$_3$ was then added to avoid an emulsion, and the basic organic mixture was extracted with ether. The combined ether layers were washed with sat. aq. NaHCO$_3$, water, brine, dried Na$_2$SO$_4$, filtered, and concentrated to dryness to give the crude product. The crude product was purified by eluting through silica with EtOAc/Hexane (1:4 v/v). The purified product contained some residual 3-bromopropyl phthalimide, which did not interfere with subsequent synthetic steps. The material was taken on and used without further purification. Assume a quantitative yield.

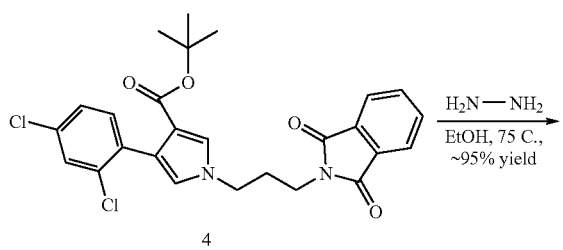

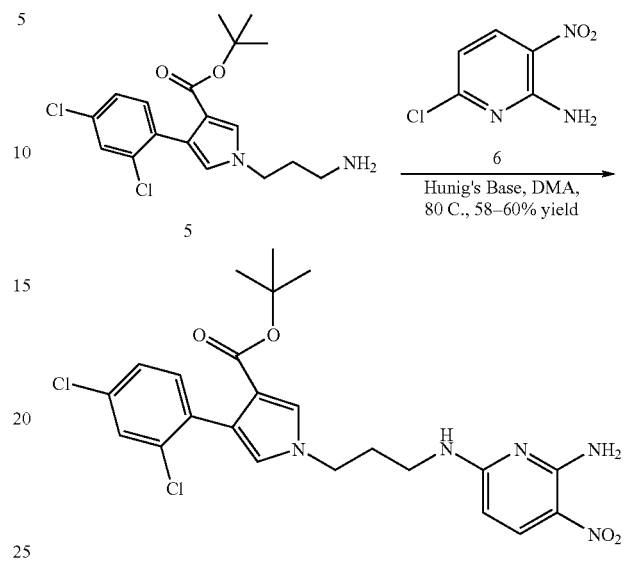

Preparation of tert-butyl 1-(3-aminopropyl)4-(2,4-dichlorophenyl)pyrrole-3-carboxylate (5)

The Pthalimido Pyrrole 4 (1 eq) was dissolved in ethanol and hydrazine (3 eq) at room temperature under nitrogen. Upon heating to reflux, the reaction generated a white precipitate. Stir at reflux until complete (~2 h) by TLC (CH$_2$Cl$_2$/acetonitrile (95:5 v/v), the UV active product was at R$_f$=0.2) and LCMS. Upon reaching completion, the reaction was allowed to cool to room temperature and the precipitate was vacuum-filtered off using a medium to fine cintered-glass filter. The filtrate was concentrated under reduced pressure to a gummy solid. The crude material was taken up in ethanol/EtOAc (1:1 v/v), stirred and the precipitate was filtered off in the same fashion as before. The filtrate was concentrated under reduced pressure and than dried in vacuo for 10-15 min. This process of adding ethanol/EtOAc, filtering and concentrating was done one more time or as needed to remove the majority of the white precipitate and residual hydrazine. The product was then dried in vacuo overnight. The material was used without further purification. Once dried, the reaction yielded the product as a glass (~87% yield over 2 steps).

Preparation of tert-butyl 1-{3-[(6-amino-5-nitro(2-pyridyl))amino]propyl}4-(2,4-dichlorophenyl)pyrrole-3-carboxylate (7)

To the premixed dry reagents, pyrrole 5 (1 eq) and powdered 6-chloro-3-nitro-2-pyridylamine (6) (1.1 eq), was added the DMA followed by Hünig's base (2 eq) sequentially with stirring at rt. The reaction was then heated to 80° C. overnight. The reaction was followed by TLC (EtOAc/hexane (1:1 v/v), the UV active yellow product was at R$_f$=0.25), HPLC and LCMS. Upon completion as judged by HPLC, the reaction was allowed to cool to 70° C. Ethylene diamine (anhydrous) was then added to the reaction to destroy any remaining unreacted chloropyridine 6. After 15 min stirring at 70° C., the reaction was cooled and quenched with the addition of sat. aq. NaHCO$_3$. The aqueous mixture was extracted with EtOAc, and the combined organic layers were washed with sat. aq. NaHCO$_3$, water, brine, dried, filtered, and concentrated to dryness to give the crude product as a brown-yellow solid. The crude product was purified by flash chromatography eluted with EtOAc/hexane (4:6 v/v). The purified SnAr adduct 7 was isolated in 58% yield as a yellow solid.

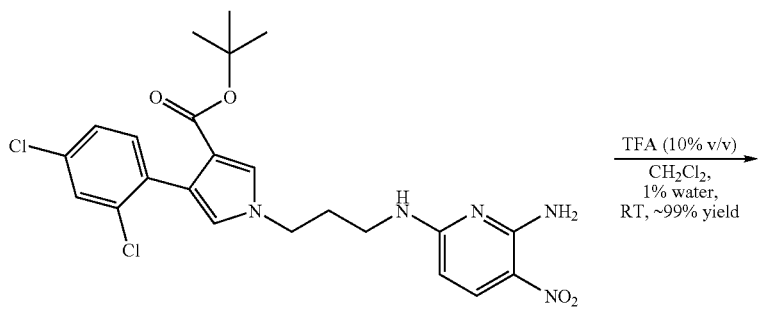

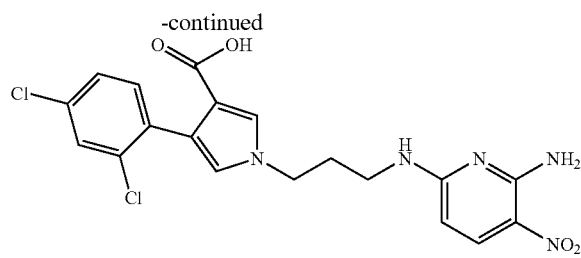

8

Preparation f 1-{3-[(6-amino-5-nitro(2-pyridyl))amino]pr pyl}-4-(2,4-dichlorophenyl)pyrrole-3-carboxylic acid (8)

In a vial, TFA (catalytic amount) was added to a stirred mixture of tert-butyl ester pyrrole 7 (1 eq), water (0.1%), and CH₂Cl₂ at rt. The vial stirred at room temperature until done (~12 h). The reaction was then concentrated under reduced pressure at room temperature and dried in vacuo. The crude residue was dissolved again in CH₂Cl₂ and concentrated under reduced pressure at rt. The material was used in the final coupling step without further purification as the TFA salt.

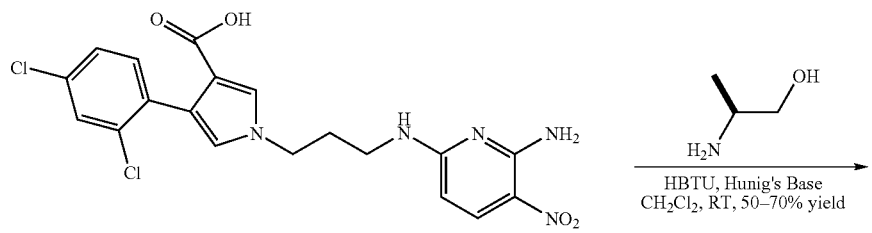

8

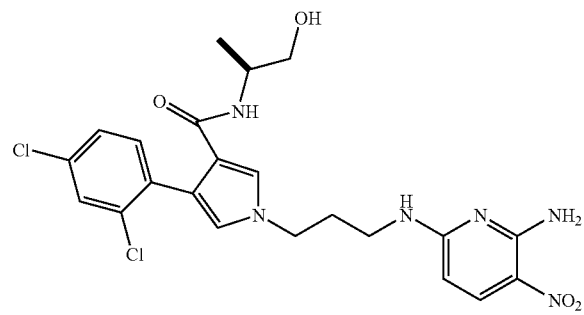

CHIR 154703

9

Preparation of N-((1S)-2-hydroxy-isopropyl)(1-{3-[(6-amino-5-nitro(2-pyridyl))amino]propyl}4-(2,4-dichlorophenyl)pyrrol-3-yl)carboxamide (9, CHIR 154703)

(2S)-(+)-2-Aminopropan-1-ol (1.5 eq) was added to a stirred mixture of acid (8) (1 eq), HBTU (1.5 eq), Hünig's base (2 eq) and DMF (premixed sequentially in this order in a vial) at room temperature under argon. The reaction was stirred for 3-4 h until complete as shown by LCMS and HPLC. The reaction mixture was subsequently diluted with EtOAc, washed with NaHCO₃, and concentrated to afford a powder in a 70% yield.

Alternate Production of Cinnamic Esters

Preparation of tert-butyl (2E)-3-(4-ethylphenyl)prop-2-enoate

4-Ethylbenzaldehyde (1 eq) was added to a stirred suspension of tert-butyl 2-(diethoxycarbonyl)acetate (1.2 eq), Hünig's base (6 eq), LiCl (3 eq) and CH$_3$CN. The reaction mixture was heated to reflux to completely dissolve the aldehyde. After heating at 50-60° C. for 12 hours, the reaction was judged to be complete by TLC. The reaction, which contains a fine suspension of LiCl was partitioned between CH$_2$Cl$_2$ and water. The organic layer was washed with 1M aq. citric acid, sat. aq. NaHCO$_3$, water, and brine. The organic layer was dried (Na$_2$SO$_4$), filtered, and concentrated to dryness to give the crude product as a solid. The crude solid was dissolved in a minimal amount of hot CH$_2$Cl$_2$ followed by addition of approximately 6 times the volume of hexane. The slightly cloudy mixture was left overnight to crystallize. Tert-butyl (2E)-3-(4-ethylphenyl) prop-2-enoate was attained as an oil, which was further purified by column chromatography using 5-10% EtOAc in hexane as eluent. LC/MS m/z 233.3 MH+ (80% yield).

Examples 2-362

Synthesis of Pyrrole Compounds

Examples 2-362 were synthesized following the synthetic schemes described above in Method 1 and in Schemes 1-4 directly following the table. The precursors are readily recognizable by one skilled in the art and are commercially available from Aldrich (Milwaukee, Wis.) or Acros Organics (Pittsburgh, Pa.).

| EXAMPLE | NAME | MH+ |
|---|---|---|
| 2 | 1-{3-[(6-amino-5-nitropyridin-2-yl)amino]propyl}-N-(2-cyano-ethyl)-4-[4-(1H-imidazol-1-yl)phenyl]-1H-pyrrole-3-carboxamide | 500.5 |
| 3 | 1-{3-[(6-amino-5-nitropyridin-2-yl)amino]propyl}-N-(2-hydroxy-ethyl)-4-[4-(1H-imidazol-1-yl)phenyl]-1H-pyrrole-3-carboxamide | 491.5 |
| 4 | 1-{3-[(6-amino-5-nitropyridin-2-yl)amino]propyl}-4-[4-(1H-imidazol-1-yl)phenyl]-N-(3-methoxypropyl)-1H-pyrrole-3-carboxamide | 519.6 |
| 5 | N-((1S)-1-carbamoyl-2-hydroxyethyl)(1-{3-[(6-amino-5-nitro(2-pyridyl))amino]propyl}-4-(4-imidazolylphenyl)pyrrol-3-yl)carboxamide | 534.5 |
| 6 | 1-{3-[(6-amino-5-nitropyridin-2-yl)amino]propyl}-N-cyclopropyl-4-[4-(1H-imidazol-1-yl)phenyl]-1H-pyrrole-3-carboxamide | 487.5 |
| 7 | 1-{3-[(6-amino-5-nitropyridin-2-yl)amino]propyl}-4-(2,4-di-chlorophenyl)-N-[(1S)-2-hydroxy-1-methylethyl]-1H-pyrrole-3-carboxamide | 508.4 |
| 8 | methyl N-({1-{3-[(6-amino-5-nitropyridin-2-yl)amino]propyl}-4-[4-(1H-imidazol-1-yl)phenyl]-1H-pyrrol-3-yl}carbonyl)serinate | 549.6 |
| 9 | 1-{3-[(6-amino-5-nitropyridin-2-yl)amino]propyl}-4-[4-(1H-imidazol-1-yl)phenyl]-N-[3-(2-oxopyrrolidin-1-yl)propyl]-1H-pyrrole-3-carboxamide | 572.6 |
| 10 | 1-{3-[(6-amino-5-nitropyridin-2-yl)amino]propyl}-N-[(2S)-2-hydroxypropyl]-4-[4-(1H-imidazol-1-yl)phenyl]-1H-pyrrole-3-carboxamide | 505.5 |
| 11 | 1-{3-[(6-amino-5-nitropyridin-2-yl)amino]propyl}-N-[(1S)-2-hydroxy-1-methylethyl]-4-[4-(1H-imidazol-1-yl)phenyl]-1H-pyrrole-3-carboxamide | 505.5 |
| 12 | 1-{3-[(5-cyanopyridin-2-yl)amino]propyl}-4-(2,4-dichloro-phenyl)-N-[(2R)-2-hydroxypropyl]-1H-pyrrole-3-carboxamide | 473.4 |
| 13 | 1-{3-[(6-amino-5-nitropyridin-2-yl)amino]propyl}-4-(2,4-dichlorophenyl)-N-[2-hydroxy-1-(hydroxymethyl)ethyl]-1H-pyrrole-3-carboxamide | 524.4 |
| 14 | N-[2-(acetylamino)ethyl]-1-{3-[(6-amino-5-nitropyridin-2-yl)-amino]propyl}-4-[4-(1H-imidazol-1-yl)phenyl]-1H-pyrrole-3-carboxamide | 532.6 |
| 15 | 1-{3-[(6-amino-5-nitropyridin-2-yl)amino]propyl}-4-(2,4-dichlorophenyl)-N-[(2S)-2-hydroxypropyl]-1H-pyrrole-3-carboxamide | 508.4 |
| 16 | 1-{3-[(5-cyanopyridin-2-yl)amino]propyl}-4-(2,4-dichloro-phenyl)-N-[(1S)-2-hydroxy-1-methylethyl]-1H-pyrrole-3-carboxamide | 505.5 |
| 17 | 1-{3-[(6-amino-5-nitropyridin-2-yl)amino]propyl}-4-(2,4-dichlorophenyl)-N-[(1R)-2-hydroxy-1-methylethyl]-1H-pyrrole-3-carboxamide | 508.4 |
| 18 | 1-{3-[(6-amino-5-nitropyridin-2-yl)amino]propyl}-4-(2,4-dichlorophenyl)-N-(2-hydroxyethyl)-1H-pyrrole-3-carboxamide | 494.3 |
| 19 | 1-{3-[(5-cyanopyridin-2-yl)amino]propyl}-4-(2,4-dichloro-phenyl)-N-[(2S)-2-hydroxypropyl]-1H-pyrrole-3-carboxamide | 473.4 |
| 20 | 1-{3-[(6-amino-5-nitropyridin-2-yl)amino]propyl}-4-[4-(1H-imidazol-1-yl)phenyl]-N-(2-pyridin-2-ylethyl)-1H-pyrrole-3-carboxamide | 552.6 |
| 21 | 4-(2,4-dichlorophenyl)-N-[(1S)-2-hydroxy-1-methylethyl]-1-{3-[(5-nitropyridin-2-yl)amino]propyl}-1H-pyrrole-3-carboxamide | 493.4 |
| 22 | 1-{3-[(5-cyanopyridin-2-yl)amino]propyl}-4-(2,4-dichloro-phenyl)-N-[(1S)-2-hydroxy-1-methylethyl]-1H-pyrrole-3-carboxamide | 473.4 |

-continued

| EXAMPLE | NAME | MH+ |
|---|---|---|
| 23 | 1-{3-[(6-amino-5-nitropyridin-2-yl)amino]propyl}-4-[4-(1H-imidazol-1-yl)phenyl]-N-(pyridin-3-ylmethyl)-1H-pyrrole-3-carboxamide | 538.6 |
| 24 | 1-{3-[(6-amino-5-nitropyridin-2-yl)amino]propyl}-N-[(1R)-2-hydroxy-1-methylethyl]-4-[4-(1H-imidazol-1-yl)phenyl]-1H-pyrrole-3-carboxamide | 505.5 |
| 25 | 1-{3-[(5-cyanopyridin-2-yl)amino]propyl}-4-(2,4-dichlorophenyl)-N-[(1R)-2-hydroxy-1-methylethyl]-1H-pyrrole-3-carboxamide | 473.4 |
| 26 | 4-(2,4-dichlorophenyl)-N-[(2S)-2-hydroxypropyl]-1-{3-[(5-nitropyridin-2-yl)amino]propyl}-1H-pyrrole-3-carboxamide | 493.4 |
| 27 | N-1-[1-{3-[(6-amino-5-nitropyridin-2-yl)amino]propyl}-4-(2,4-dichlorophenyl)-1H-pyrrol-3-yl]serinamide | 509.4 |
| 28 | 1-{3-[(6-amino-5-nitropyridin-2-yl)amino]propyl}-4-(2-chloro-4-fluorophenyl)-N-[(1S)-2-hydroxy-1-methylethyl]-1H-pyrrole-3-carboxamide | 491.9 |
| 29 | 4-(2,4-dichlorophenyl)-N-[(1R)-2-hydroxy-1-methylethyl]-1-{3-[(5-nitropyridin-2-yl)amino]propyl}-1H-pyrrole-3-carboxamide | 493.4 |
| 30 | 1-{3-[(6-amino-5-nitropyridin-2-yl)amino]propyl}-4-(2,4-dichlorophenyl)-N-(tetrahydrofuran-2-ylmethyl)-1H-pyrrole-3-carboxamide | 534.4 |
| 31 | N-[1-{3-[(6-amino-5-nitropyridin-2-yl)amino]propyl}-4-(2,4-dichlorophenyl)-1H-pyrrol-3-yl]-4-hydroxyprolinamide | 535.4 |
| 32 | 1-{3-[(6-amino-5-nitropyridin-2-yl)amino]propyl}-4-(2,4-dichlorophenyl)-N-[2-(2-hydroxyethoxy)ethyl]-1H-pyrrole-3-carboxamide | 538.4 |
| 33 | 1-{3-[(6-amino-5-nitropyridin-2-yl)amino]propyl}-4-(2-chloro-4-fluorophenyl)-N-[(2S)-2-hydroxypropyl]-1H-pyrrole-3-carboxamide | 491.9 |
| 34 | methyl (4R)-1-({1-{3-[(6-amino-5-nitropyridin-2-yl)amino]-propyl}-4-[4-(1H-imidazol-1-yl)phenyl]-1H-pyrrol-3-yl}-carbonyl)-4-hydroxy-L-prolinate | 575.6 |
| 35 | 4-(2,4-dichlorophenyl)-N-[(2R)-2-hydroxypropyl]-1-{3-[(5-nitro-pyridin-2-yl)amino]propyl}-1H-pyrrole-3-carboxamide | 493.4 |
| 36 | 1-{3-[(6-amino-5-nitropyridin-2-yl)amino]propyl}-4-(2,4-dichlorophenyl)-N-(4-hydroxycyclohexyl)-1H-pyrrole-3-carboxamide | 548.4 |
| 37 | 1-{3-[(6-amino-5-nitropyridin-2-yl)amino]propyl}-4-(2-chloro-4-fluorophenyl)-N-[(2R)-2-hydroxypropyl]-1H-pyrrole-3-carboxamide | 491.9 |
| 38 | 1-{3-[(6-amino-5-nitropyridin-2-yl)amino]propyl}-4-(2,4-dichlorophenyl)-N-[(2R)-2-hydroxypropyl]-1H-pyrrole-3-carboxamide | 508.4 |
| 39 | 1-{3-[(6-amino-5-nitropyridin-2-yl)amino]propyl}-4-(2,4-dichlorophenyl)-N-[2-(2-oxo-2,3-dihydro-1H-imidazol-1-yl)ethyl]-1H-pyrrole-3-carboxamide | 560.4 |
| 40 | 1-{3-[(6-amino-5-nitropyridin-2-yl)amino]propyl}-4-(2,4-dichlorophenyl)-N-(2-hydroxyethyl)-N-methyl-1H-pyrrole-3-carboxamide | 508.4 |
| 41 | 1-{3-[(6-amino-5-nitropyridin-2-yl)amino]propyl}-4-(2-chloro-4-fluorophenyl)-N-[(1R)-2-hydroxy-1-methylethyl]-1H-pyrrole-3-carboxamide | 491.9 |
| 42 | 1-{3-[(6-amino-5-nitropyridin-2-yl)amino]propyl}-4-(2,4-dichlorophenyl)-N-(4-methylpiperazin-1-yl)-1H-pyrrole-3-carboxamide | 548.4 |
| 43 | 1-{3-[(6-amino-5-nitropyridin-2-yl)amino]propyl}-4-[4-(1H-imidazol-1-yl)phenyl]-N-(4-morpholin-4-ylphenyl)-1H-pyrrole-3-carboxamide | 608.7 |
| 44 | N-2-[2-(acetylamino)ethyl]-N-1-[1-{3-[(6-amino-5-nitropyridin-2-yl)amino]propyl}-4-(2,4-dichlorophenyl)-1H-pyrrol-3-yl]glycinamide | 564.4 |
| 45 | 1-{3-[(6-amino-5-nitropyridin-2-yl)amino]propyl}-4-[4-(1H-imidazol-1-yl)phenyl]-1H-pyrrole-3-carboxylic acid | 448.5 |
| 46 | 1-{3-[(6-amino-5-nitropyridin-2-yl)amino]propyl}-4-(2-chlorophenyl)-N-[(1R)-2-hydroxy-1-methylethyl]-1H-pyrrole-3-carboxamide | 473.9 |
| 47 | 1-{3-[(6-amino-5-nitropyridin-2-yl)amino]propyl}-4-(2,4-dichlorophenyl)-N-(3-pyrrolidin-1-ylpropyl)-1H-pyrrole-3-carboxamide | 561.5 |
| 48 | 2-[(3S)-3-(acetylamino)pyrrolidin-1-yl]-N-[1-{3-[(6-amino-5-nitropyridin-2-yl)amino]propyl}-4-(4-ethylphenyl)-1H-pyrrol-3-yl]acetamide | 549.6 |
| 49 | 1-{3-[(6-amino-5-nitropyridin-2-yl)amino]propyl}-4-(2-chlorophenyl)-N-[(1S)-2-hydroxy-1-methylethyl]-1H-pyrrole-3-carboxamide | 473.9 |

-continued

| EXAMPLE | NAME | MH+ |
|---|---|---|
| 50 | 1-{3-[(6-amino-5-nitropyridin-2-yl)amino]propyl}-N-[2-(dimethylamino)ethyl]-4-[4-(1H-imidazol-1-yl)phenyl]-1H-pyrrole-3-carboxamide | 518.6 |
| 51 | 1-{3-[(6-amino-5-nitropyridin-2-yl)amino]propyl}-4-(2,4-dichlorophenyl)-N-[2-(2-methyl-4-nitro-2,3-dihydro-1H-imidazol-1-yl)ethyl]-1H-pyrrole-3-carboxamide | 605.5 |
| 52 | 1-{3-[(6-amino-5-nitropyridin-2-yl)amino]propyl}-4-(2,4-dichlorophenyl)-N-(2-hydroxy-1,1-dimethylethyl)-1H-pyrrole-3-carboxamide | 522.4 |
| 53 | 2-[(3S)-3-(acetylamino)pyrrolidin-1-yl]-N-[1-{3-[(6-amino-5-nitropyridin-2-yl)amino]propyl}-4-(2,4-dichlorophenyl)-1H-pyrrol-3-yl]acetamide | 590.5 |
| 54 | 1-{3-[(6-amino-5-nitropyridin-2-yl)amino]propyl}-4-(2,4-dichlorophenyl)-N-(2-morpholin-4-ylethyl)-1H-pyrrole-3-carboxamide | 563.5 |
| 55 | 1-{3-[(6-amino-5-nitropyridin-2-yl)amino]propyl}-4-(2,4-dichlorophenyl)-N-[3-(2-oxopyrrolidin-1-yl)propyl]-1H-pyrrole-3-carboxamide | 575.5 |
| 56 | N-1-[1-{3-[(6-amino-5-nitropyridin-2-yl)amino]propyl}-4-(2,4-dichlorophenyl)-1H-pyrrol-3-yl]-N-2-(2-cyanoethyl)glycinamide | 532.4 |
| 57 | 1-{3-[(6-amino-5-nitropyridin-2-yl)amino]propyl}-4-(2,4-dichlorophenyl)-N-(3-hydroxypropyl)-1H-pyrrole-3-carboxamide | 508.4 |
| 58 | 1-{3-[(6-amino-5-nitropyridin-2-yl)amino]propyl}-4-(2,4-dichlorophenyl)-N-(2-pyrrolidin-1-ylethyl)-1H-pyrrole-3-carboxamide | 547.5 |
| 59 | 1-[1-{3-[(6-amino-5-nitropyridin-2-yl)amino]propyl}-4-(2,4-dichlorophenyl)-1H-pyrrol-3-yl]-4-methylpiperazin-2-one | 519.4 |
| 60 | 1-{3-[(6-amino-5-nitropyridin-2-yl)amino]propyl}-4-(2-chloro-phenyl)-N-[(2R)-2-hydroxypropyl]-1H-pyrrole-3-carboxamide | 473.9 |
| 61 | 1-{3-[(6-amino-5-nitropyridin-2-yl)amino]propyl}-4-(2,4-dichlorophenyl)-N-(2-hydroxy-3-morpholin-4-ylpropyl)-1H-pyrrole-3-carboxamide | 593.5 |
| 62 | 1-{3-[(6-amino-5-nitropyridin-2-yl)amino]propyl}-4-(2,4-dichlorophenyl)-N-(2-hydroxy-3-pyrrolidin-1-ylpropyl)-1H-pyrrole-3-carboxamide | 577.5 |
| 63 | 1-{3-[(6-amino-5-nitropyridin-2-yl)amino]propyl}-4-(4-ethyl-phenyl)-N-[(1R)-2-hydroxy-1-methylethyl]-1H-pyrrole-3-carboxamide | 467.5 |
| 64 | N-1-[1-{3-[(6-amino-5-nitropyridin-2-yl)amino]propyl}-4-(2,4-dichlorophenyl)-1H-pyrrol-3-yl]-N-2-(2-hydroxyethyl)-glycinamide | 523.4 |
| 65 | 1-{3[(6-amino-5-nitropyridin-2-yl)amino]Propyl}-4-(2,4-dichlorophenyl)-N-(2-pyridin-3-ylethyl)-1H-pyrrole-3-carboxamide | 555.4 |
| 66 | 1-{3-[(6-amino-5-nitropyridin-2-yl)amino]propyl}-4-(2,4-dichlorophenyl)-N-[(2S)-tetrahydrofuran-2-ylmethyl]-1H-pyrrole-3-carboxamide | 534.4 |
| 67 | 2-[(3R)-3-(acetylamino)pyrrolidin-1-yl]-N-[1-{3-[(6-amino-5-nitropyridin-2-yl)amino]propyl}-4-(2,4-dichlorophenyl)-1H-pyrrol-3-yl]acetamide | 590.5 |
| 68 | tert-butyl 1-({[1-{3-[(6-amino-5-nitropyridin-2-yl)amino]propyl}-4-(2,4-dichlorophenyl)-1H-pyrrol-3-yl]amino}carbonyl)-3-(methylsulfinyl)propylcarbamate | 669.6 |
| 69 | 1-{3-[(6-amino-5-nitropyridin-2-yl)amino]propyl}-4-(2-chloro-phenyl)-N-[(2S)-2-hydroxypropyl]-1H-pyrrole-3-carboxamide | 473.9 |
| 70 | 1-{3-[(6-amino-5-nitropyridin-2-yl)amino]propyl}-4-(2,4-dichlorophenyl)-N-(3-morpholin-4-ylpropyl)-1H-pyrrole-3-carboxamide | 577.5 |
| 71 | N-(3-aminocyclohexyl)-1-{3-[(6-amino-5-nitropyridin-2-yl)-amino]propyl}-4-[4-(1H-imidazol-1-yl)phenyl]-1H-pyrrole-3-carboxamide | 544.6 |
| 72 | 1-{3-[(6-amino-5-nitropyridin-2-yl)amino]propyl}-4-(2,4-dichlorophenyl)-N-[3-(dimethylamino)-2,2-dimethylpropyl]-1H-pyrrole-3-carboxamide | 563.5 |
| 73 | N-(2-aminoethyl)-1-{3-[(6-amino-5-nitropyridin-2-yl)amino]-propyl}-4-(2,4-dichlorophenyl)-1H-pyrrole-3-carboxamide | 493.4 |
| 74 | 1-{3-[(6-amino-5-nitropyridin-2-yl)amino]propyl}-N-{2-[(5-cyanopyridin-2-yl)amino]ethyl}-4-[4-(1H-imidazol-1-yl)phenyl]-1H-pyrrole-3-carboxamide | 592.6 |
| 75 | 1-{3-[(6-amino-5-nitropyridin-2-yl)amino]propyl}-4-(2,4-dichlorophenyl)-N-(pyridin-2-ylmethyl)-1H-pyrrole-3-carboxamide | 541.4 |
| 76 | 1-{3-[(6-amino-5-nitropyridin-2-yl)amino]propyl}-4-(2,4-dichlorophenyl)-N-(2-pyridin-2-ylethyl)-1H-pyrrole-3-carboxamide | 555.4 |
| 77 | tert-butyl 4-(2,4-dichlorophenyl)-1-{3-[(5-nitropyridin-2-yl)-amino]propyl}-1H-pyrrole-3-carboxylate | 492.4 |

-continued

| EXAMPLE | NAME | MH+ |
|---|---|---|
| 78 | 1-{3-[(6-amino-5-nitropyridin-2-yl)amino]propyl}-4-(2,4-dichlorophenyl)-N-(2-pyridin-4-ylethyl)-1H-pyrrole-3-carboxamide | 555.4 |
| 79 | tert-butyl 1-{3-[(6-amino-5-nitropyridin-2-yl)amino]propyl}-4-(2-chloro-4-fluorophenyl)-1H-pyrrole-3-carboxylate | 490.9 |
| 80 | 1-{3-[(6-amino-5-nitropyridin-2-yl)amino]propyl}-4-(2,4-dichlorophenyl)-N-[(2R)-tetrahydrofuran-2-ylmethyl]-1H-pyrrole-3-carboxamide | 534.4 |
| 81 | N-1-[1-{3-[(6-amino-5-nitropyridin-2-yl)amino]propyl}-4-(2,4-dichlorophenyl)-1H-pyrrol-3-yl]-N-2-(pyridin-3-ylmethyl)-glycinamide | 570.5 |
| 82 | tert-butyl 5-[N-(1-{3-[(6-amino-5-nitro(2-pyridyl))amino]propyl}-4-(2,4-dichlorophenyl)pyrrol-3-yl)carbamoyl]-3-hydroxy-pyrrolidinecarboxylate | 635.5 |
| 83 | N-1-[1-{3-[(6-amino-5-nitropyridin-2-yl)amino]propyl}-4-(2,4-dichlorophenyl)-1H-pyrrol-3-yl]-N-2-(3-methoxypropyl)-glycinamide | 551.4 |
| 84 | 1-{3-[(6-amino-5-nitropyridin-2-yl)amino]propyl}-4-(2,4-dichlorophenyl)-N-[3-(4-methylpiperazin-1-yl)propyl]-1H-pyrrole-3-carboxamide | 590.5 |
| 85 | N-1-[1-{3-[(6-amino-5-nitropyridin-2-yl)amino]propyl}-4-(2,4-dichlorophenyl)-1H-pyrrol-3-yl]-N-2-[3-(2-oxopyrrolidin-1-yl)propyl]glycinamide | 604.5 |
| 86 | N-[1-{3-[(6-amino-5-nitropyridin-2-yl)amino]propyl}-4-(2,4-dichlorophenyl)-1H-pyrrol-3-yl]morpholine-4-carboxamide | 535.4 |
| 87 | tert-butyl 1-{3-[(5-cyanopyridin-2-yl)amino]propyl}-4-(2,4-dichlorophenyl)-1H-pyrrole-3-carboxylate | 472.4 |
| 88 | tert-butyl N-{[1-{3-[(6-amino-5-nitropyridin-2-yl)amino]propyl}-4-(2,4-dichlorophenyl)-1H-pyrrol-3-yl]carbonyl}-O-(tert-butyl)-D-serinate | 650.6 |
| 89 | N-[1-{3-[(6-amino-5-nitropyridin-2-yl)amino]propyl}-4-(2,4-dichlorophenyl)-1H-pyrrol-3-yl]-N'-(2-cyanoethyl)urea | 518.4 |
| 90 | tert-butyl 1-{3-[(6-amino-5-nitropyridin-2-yl)amino]propyl}-4-[4-(1H-imidazol-1-yl)phenyl]-1H-pyrrole-3-carboxylate | 504.6 |
| 91 | 2-amino-N-[1-{3-[(6-amino-5-nitropyridin-2-yl)amino]propyl}-4-(2,4-dichlorophenyl)-1H-pyrrol-3-yl]-4-(methylsulfinyl)-butanamide | 569.5 |
| 92 | N-6-{3-[3-[4-(1H-imidazol-1-yl)phenyl]-4-(pyrrolidin-1-yl-carbonyl)-1H-pyrrol-1-yl]propyl}-3-nitropyridine-2,6-diamine | 501.6 |
| 93 | N-6-[3-(3-(2,4-dichlorophenyl)-4-{[(2S)-2-(pyrrolidin-1-yl-methyl)pyrrolidin-1-yl]carbonyl}-1H-pyrrol-1-yl)propyl]-3-nitro-pyridine-2,6-diamine | 587.5 |
| 94 | 1-{3-[(6-amino-5-nitropyridin-2-yl)amino]propyl}-4-(2-chloro-4-fluorophenyl)-1H-pyrrole-3-carboxylic acid | 434.8 |
| 95 | 1-{3-[(6-amino-5-nitropyridin-2-yl)amino]propyl}-4-(2,4-dichlorophenyl)-N-[1-(hydroxymethyl)cyclopentyl]-1H-pyrrole-3-carboxamide | 548.4 |
| 96 | 1-{3-[(6-amino-5-nitropyridin-2-yl)amino]propyl}-4-(2,4-dichlorophenyl)-N-[2-(1-methylpyrrolidin-2-yl)ethyl]-1H-pyrrole-3-carboxamide | 561.5 |
| 97 | 1-{3-[(6-amino-5-nitropyridin-2-yl)amino]propyl}-N-[(3R)-1-azabicyclo[2.2.2]oct-3-yl]-4-[4-(1H-imidazol-1-yl)phenyl]-1H-pyrrole-3-carboxamide | 556.6 |
| 98 | 1-{3-[(6-amino-5-nitropyridin-2-yl)amino]propyl}-4-(2,4-dichlorophenyl)-N-(2-piperidin-1-ylethyl)-1H-pyrrole-3-carboxamide | 561.5 |
| 99 | tert-butyl 1-{3-[(6-amino-5-nitropyridin-2-yl)amino]propyl}-4-(2-chlorophenyl)-1H-pyrrole-3-carboxylate | 472.9 |
| 100 | N-6-(3-{3-{[(3S)-3-(dimethylamino)pyrrolidin-1-yl]carbonyl}-4-[4-(1H-imidazol-1-yl)phenyl]-1H-pyrrol-1-yl}propyl)-3-nitro-pyridine-2,6-diamine | 544.6 |
| 101 | 1-{3-[(6-amino-5-nitropyridin-2-yl)amino]propyl}-4-(4-ethyl-phenyl)-N-[(2S)-2-hydroxypropyl]-1H-pyrrole-3-carboxamide | 467.5 |
| 102 | tert-butyl 1-({[1-{3-[(6-amino-5-nitropyridin-2-yl)amino]propyl}-4-(4-ethylphenyl)-1H-pyrrol-3-yl]amino}carbonyl)-3-(methyl-sulfinyl)propylcarbamate | 628.8 |
| 103 | 1-{3-[(6-amino-5-nitropyridin-2-yl)amino]propyl}-4-(2,4-dichlorophenyl)-N-[2-(dimethylamino)ethyl]-1H-pyrrole-3-carboxamide | 521.4 |
| 104 | 1-{3-[(6-amino-5-nitropyridin-2-yl)amino]propyl}-4-(2,4-dichlorophenyl)-N-(pyridin-3-ylmethyl)-1H-pyrrole-3-carboxamide | 541.4 |
| 105 | 2-amino-2-methylpropyl 1-{3-[(6-amino-5-nitropyridin-2-yl)-amino]propyl}-4-(2,4-dichlorophenyl)-1H-pyrrole-3-carboxylate | 522.4 |
| 106 | 1-{3-[(6-amino-5-nitropyridin-2-yl)amino]propyl}-4-(2,4-dichlorophenyl)-N-[3-(1H-imidazol-1-yl)propyl]-1H-pyrrole-3-carboxamide | 558.4 |

-continued

| EXAMPLE | NAME | MH+ |
|---|---|---|
| 107 | 1-{3-[(6-amino-5-nitropyridin-2-yl)amino]propyl}-4-(2,4-dichlorophenyl)-N-[(5-methylpyrazin-2-yl)methyl]-1H-pyrrole-3-carboxamide | 556.4 |
| 108 | tert-butyl 1-{3-[(6-amino-5-nitropyridin-2-yl)amino]propyl}-4-(2,4-dichlorophenyl)-1H-pyrrole-3-carboxylate | 507.4 |
| 109 | N-[1-{3-[(6-amino-5-nitropyridin-2-yl)amino]propyl}-4-(2,4-dichlorophenyl)-1H-pyrrol-3-yl]acetamide | 464.3 |
| 110 | N-[(3S)-1-({1-{3-[(6-amino-5-nitropyridin-2-yl)amino]propyl}-4-[4-(1H-imidazol-1-yl)phenyl]-1H-pyrrol-3-yl}carbonyl)pyrrolidin-3-yl]acetamide | 558.6 |
| 111 | N-1-[1-{3-[(6-amino-5-nitropyridin-2-yl)amino]propyl}-4-(2,4-dichlorophenyl)-1H-pyrrol-3-yl]-N-2-[2-(dimethylamino)ethyl]-glycinamide | 550.5 |
| 112 | N-{[1-{3-[(6-amino-5-nitropyridin-2-yl)amino]propyl}-4-(2,4-dichlorophenyl)-1H-pyrrol-3-yl]carbonyl}serine | 538.4 |
| 113 | 1-{3-[(6-amino-5-nitropyridin-2-yl)amino]propyl}-N-[(3S)-1-azabicyclo[2.2.2]oct-3-yl]-4-[4-(1H-imidazol-1-yl)phenyl]-1H-pyrrole-3-carboxamide | 556.6 |
| 114 | 1-{3-[(6-amino-5-nitropyridin-2-yl)amino]propyl}-4-(4-cyano-phenyl)-N-[(1R)-2-hydroxy-1-methylethyl]-1H-pyrrole-3-carboxamide | 464.5 |
| 115 | 1-{3-[(6-amino-5-nitropyridin-2-yl)amino]propyl}-4-(2,4-dichlorophenyl)-N-[3-(2-methylpiperidin-1-yl)propyl]-1H-pyrrole-3-carboxamide | 589.5 |
| 116 | 1-(2-{[1-{3-[(6-amino-5-nitropyridin-2-yl)amino]propyl}-4-(2,4-dichlorophenyl)-1H-pyrrol-3-yl]amino}-2-oxoethyl)piperidine-4-carboxylic acid | 591.5 |
| 117 | 1-{3-[(6-amino-5-nitropyridin-2-yl)amino]propyl}-4-(2,4-dichlorophenyl)-N-(2-furylmethyl)-1H-pyrrole-3-carboxamide | 530.4 |
| 118 | 1-{3-[(6-amino-5-nitropyridin-2-yl)amino]propyl}-4-(4-chloro-2-fluorophenyl)-N-[(1R)-2-hydroxy-1-methylethyl]-1H-pyrrole-3-carboxamide | 491.9 |
| 119 | 1-({1-{3-[(6-amino-5-nitropyridin-2-yl)amino]propyl}-4-[4-(1H-imidazol-1-yl)phenyl]-1H-pyrrol-3-yl}carbonyl)piperidin-3-ol | 531.6 |
| 120 | N-[1-({1-{3-[(6-amino-5-nitropyridin-2-yl)amino]propyl}-4-(1H-imidazol-1-yl)phenyl]-1H-pyrrol-3-yl}carbonyl)pyrrolidin-3-yl[-2,2,2-trifluoroacetamide | 612.6 |
| 121 | 1-{3-[(6-amino-5-nitropyridin-2-yl)amino]propyl}-4-(2,4-dichlorophenyl)-N-{2-[(5-nitropyridin-2-yl)amino]ethyl}-1H-pyrrole-3-carboxamide | 615.4 |
| 122 | 1-{3-[(6-amino-5-nitropyridin-2-yl)amino]propyl}-4-(4-bromo-2-fluorophenyl)-N-[(1R)-2-hydroxy-1-methylethyl]-1H-pyrrole-3-carboxamide | 536.4 |
| 123 | 1-{3-[(6-amino-5-nitropyridin-2-yl)amino]propyl}-4-(4-ethyl-phenyl)-N-[(2R)-2-hydroxypropyl]-1H-pyrrole-3-carboxamide | 467.5 |
| 124 | N-1-[1-{3-[(6-amino-5-nitropyridin-2-yl)amino]propyl}-4-(2,4-dichlorophenyl)-1H-pyrrol-3-yl]ornithinamide | 536.4 |
| 125 | 1-(2-{[1-{3-[(6-amino-5-nitropyridin-2-yl)amino]propyl}-4-(2,4-dichlorophenyl)-1H-pyrrol-3-yl]amino}-2-oxoethyl)piperidine-4-carboxamide | 590.5 |
| 126 | 1-{3-[(6-amino-5-nitropyridin-2-yl)amino]propyl}-4-(2,4-dichlorophenyl)-N-(pyridin-4-ylmethyl)-1H-pyrrole-3-carboxamide | 541.4 |
| 127 | 1-{3-[(6-amino-5-nitropyridin-2-yl)amino]propyl}-4-(4-chloro-2-methoxyphenyl)-N-(2-{[(2-cyanophenyl)sulfonyl]amino}ethyl)-1H-pyrrole-3-carboxamide | 654.1 |
| 128 | 1-{3-[(6-amino-5-nitropyridin-2-yl)amino]propyl}-4-(4-ethyl-phenyl)-N-[(1S)-2-hydroxy-1-methylethyl]-1H-pyrrole-3-carboxamide | 467.5 |
| 129 | N-[1-{3-[(6-amino-5-nitropyridin-2-yl)amino]propyl}-4-(4-ethyl-phenyl)-1H-pyrrol-3-yl]-4-hydroxyprolinamide | 494.6 |
| 130 | 1-{3-[(6-amino-5-nitropyridin-2-yl)amino]propyl}-4-(2,4-dichlorophenyl)-N-ethyl-N-(pyridin-4-ylmethyl)-1H-pyrrole-3-carboxamide | 569.5 |
| 131 | N-[1-{3-[(6-amino-5-nitropyridin-2-yl)amino]propyl}-4-(2,4-dichlorophenyl)-1H-pyrrol-3-yl]-2-morpholin-4-ylacetamide | 549.4 |
| 132 | 1-{3-[(6-amino-5-nitropyridin-2-yl)amino]propyl}-4-(2,4-difluorophenyl)-N-[(2R)-2-hydroxypropyl]-1H-pyrrole-3-carboxamide | 475.5 |
| 133 | 1-{3-[(6-amino-5-nitropyridin-2-yl)amino]propyl}-4-(2,4-dichlorophenyl)-N-(2-methoxyethyl)-1H-pyrrole-3-carboxamide | 508.4 |
| 134 | ethyl 4-({[1-{3-[(6-amino-5-nitropyridin-2-yl)amino]propyl}-4-(2,4-dichlorophenyl)-1H-pyrrol-3-yl]carbonyl}amino)piperidine-1-carboxylate | 605.5 |
| 135 | N-2-[2-(acetylamino)ethyl]-N-1-[1-{3-[(6-amino-5-nitropyridin-2-yl)amino]propyl}-4-(4-ethylphenyl)-1H-pyrrol-3-yl]glycinamide | 523.6 |

-continued

| EXAMPLE | NAME | MH+ |
|---|---|---|
| 136 | (1-aminocyclopentyl)methyl 1-{3-[(6-amino-5-nitropyridin-2-yl)-amino]propyl}-4-(2,4-dichlorophenyl)-1H-pyrrole-3-carboxylate | 548.4 |
| 137 | 1-{3-[(6-amino-5-nitropyridin-2-yl)amino]propyl}-N-[(3R,4R)-1-azabicyclo[2.2.1]hept-3-yl]-4-(2,4-dichlorophenyl)-1H-pyrrole-3-carboxamide | 545.4 |
| 138 | 2-[(3R)-3-(acetylamino)pyrrolidin-1-yl]-N-[1-{3-[(6-amino-5-nitropyridin-2-yl)amino]propyl}-4-(4-ethylphenyl)-1H-pyrrol-3-yl]acetamide | 549.6 |
| 139 | N-2-(3-aminocyclohexyl)-N-1-[1-{3-[(6-amino-5-nitropyridin-2-yl)amino]propyl}-4-(2,4-dichlorophenyl)-1H-pyrrol-3-yl]-glycinamide | 576.5 |
| 140 | 4-(2,4-dichlorophenyl)-N-[(1R)-2-hydroxy-1-methylethyl]-1-(3-{[5-(trifluoromethyl)pyridin-2-yl]amino}propyl)-1H-pyrrole-3-carboxamide | 516.4 |
| 141 | N-1-[1-{3-[(6-amino-5-nitropyridin-2-yl)amino]propyl}-4-(4-ethylphenyl)-1H-pyrrol-3-yl]serinamide | 468.5 |
| 142 | N-[(3R)-1-({1-{3-[(6-amino-5-nitropyridin-2-yl)amino]propyl}-4-[4-(1H-imidazol-1-yl)phenyl]-1H-pyrrol-3-yl}carbonyl)pyrrolidin-3-yl]acetamide | 558.6 |
| 143 | 1-{3-[(6-amino-5-nitropyridin-2-yl)amino]propyl}-4-(2,4-difluorophenyl)-N-[(1R)-2-hydroxy-1-methylethyl]-1H-pyrrole-3-carboxamide | 515.6 |
| 144 | N-[1-{3-[(6-amino-5-nitropyridin-2-yl)amino]propyl}-4-(2,4-dichlorophenyl)-1H-pyrrol-3-yl]-2-(1H-imidazol-1-yl)acetamide | 530.4 |
| 145 | N-[1-{3-[(6-amino-5-nitropyridin-2-yl)amino]propyl}-4-(2,4-dichlorophenyl)-1H-pyrrol-3-yl]-N'-[2-(dimethylamino)ethyl]urea | 536.4 |
| 146 | N-6-{3-[3-[4-(1H-imidazol-1-yl)phenyl]-4-(morpholin-4-ylcarbonyl)-1H-pyrrol-1-yl]propyl}-3-nitropyridine-2,6-diamine | 517.6 |
| 147 | N-1-[1-{3-[(6-amino-5-nitropyridin-2-yl)amino]propyl}-4-(4-ethylphenyl)-1H-pyrrol-3-yl]-N-2-[3-(2-oxopyrrolidin-1-yl)-propyl]glycinamide | 563.7 |
| 148 | 1-{3-[(6-amino-5-nitropyridin-2-yl)amino]propyl}-4-(2,4-difluorophenyl)-N-[(1R)-2-hydroxy-1-methylethyl]-1H-pyrrole-3-carboxamide | 475.5 |
| 149 | 1-{3-[(6-amino-5-nitropyridin-2-yl)amino]propyl}-4-(2-chloro-phenyl)-1H-pyrrole-3-carboxylic acid | 416.8 |
| 150 | N-[1-{3-[(6-amino-5-nitropyridin-2-yl)amino]propyl}-4-(2,4-dichlorophenyl)-1H-pyrrol-3-yl]-2-[(3S)-3-(dimethylamino)-pyrrolidin-1-yl]acetamide | 576.5 |
| 151 | 1-{3-[(6-amino-5-nitropyridin-2-yl)amino]propyl}-4-(2,4-dichlorophenyl)-1H-pyrrole-3-carboxylic acid | 451.3 |
| 152 | 1-{3-[(6-amino-5-nitropyridin-2-yl)amino]propyl}-4-(2,4-dichlorophenyl)-N-(piperidin-4-ylmethyl)-1H-pyrrole-3-carboxamide | 547.5 |
| 153 | N-[1-{3-[(6-amino-5-nitropyridin-2-yl)amino]propyl}-4-(2,4-dichlorophenyl)-1H-pyrrol-3-yl]-2-[(3R)-3-(dimethylamino)-pyrrolidin-1-yl]acetamide | 576.5 |
| 154 | N-6-(3-{3-(azepan-1-ylcarbonyl)-4-[4-(1H-imidazol-1-yl)phenyl]-1H-pyrrol-1-yl}propyl)-3-nitropyridine-2,6-diamine | 529.6 |
| 155 | 1-{3-[(6-amino-5-nitropyridin-2-yl)amino]propyl}-4-(2,4-difluorophenyl)-N-[(1S)-2-hydroxy-1-methylethyl]-1H-pyrrole-3-carboxamide | 475.5 |
| 156 | 1-{3-[(6-amino-5-nitropyridin-2-yl)amino]propyl}-4-(4-chloro-2-fluorophenyl)-N-[(1S)-2-hydroxy-1-methylethyl]-1H-pyrrole-3-carboxamide | 491.9 |
| 157 | 4-(2,4-dichlorophenyl)-1-{3-[(5-nitropyridin-2-yl)amino]propyl}-1H-pyrrole-3-carboxylic acid | 436.3 |
| 158 | 1-{3-[(6-amino-5-nitropyridin-2-yl)amino]propyl}-N-[(1R)-2-hydroxy-1-methylethyl]-4-(4-methylphenyl)-1H-pyrrole-3-carboxamide | 453.5 |
| 159 | N-1-[1-{3-[(6-amino-5-nitropyridin-2-yl)amino]propyl}-4-(4-ethylphenyl)-1H-pyrrol-3-yl]-N-2-(2-cyanoethyl)glycinamide | 491.6 |
| 160 | 1-(2-{[1-{3-[(6-amino-5-nitropyridin-2-yl)amino]propyl}-4-(4-ethylphenyl)-1H-pyrrol-3-yl]amino}-2-oxoethyl)piperidine-4-carboxamide | 549.6 |
| 161 | 4-(2,4-dichlorophenyl)-N-[(1S)-2-hydroxy-1-methylethyl]-1-(3-{[5-(trifluoromethyl)pyridin-2-yl]amino}propyl)-1H-pyrrole-3-carboxamide | 516.4 |
| 162 | 1-{3-[(6-amino-5-nitropyridin-2-yl)amino]propyl}-4-(4-cyano-phenyl)-N-[(2R)-2-hydroxypropyl]-1H-pyrrole-3-carboxamide | 464.5 |
| 163 | 1-{3-[(6-amino-5-nitropyridin-2-yl)amino]propyl}-4-(4-cyano-phenyl)-N-[(1S)-2-hydroxy-1-methylethyl]-1H-pyrrole-3-carboxamide | 464.5 |
| 164 | tert-butyl 2-({[1-{3-[(6-amino-5-nitropyridin-2-yl)amino]propyl}-4-(2,4-dichlorophenyl)-1H-pyrrol-3-yl]carbonyl}amino)ethyl-carbamate | 593.5 |

| EXAMPLE | NAME | MH+ |
|---|---|---|
| 165 | 1-{3-[(6-amino-5-nitropyridin-2-yl)amino]propyl}-N-[(1R)-2-hydroxy-1-methylethyl]-4-[4-(trifluoromethoxy)phenyl]-1H-pyrrole-3-carboxamide | 523.5 |
| 166 | 4-(2,4-dichlorophenyl)-N-[(2R)-2-hydroxypropyl]-1-(3-{[5-(trifluoromethyl)pyridin-2-yl]amino}propyl)-1H-pyrrole-3-carboxamide | 516.4 |
| 167 | N-[1-{3-[(6-amino-5-nitropyridin-2-yl)amino]propyl}-4-(2,4-dichlorophenyl)-1H-pyrrol-3-yl]-2-pyrrolidin-1-ylacetamide | 533.4 |
| 168 | 1-{3-[(6-amino-5-nitropyridin-2-yl)amino]propyl}-4-(4-chloro-2-fluorophenyl)-N-[(2S)-2-hydroxypropyl]-1H-pyrrole-3-carboxamide | 491.9 |
| 169 | N-1-[1-{3-[(6-amino-5-nitropyridin-2-yl)amino]propyl}-4-(4-ethylphenyl)-1H-pyrrol-3-yl]-N-2-(pyridin-3-ylmethyl)-glycinamide | 529.6 |
| 170 | N-{[1-{3-[(6-amino-5-nitropyridin-2-yl)amino]propyl}-4-(2,4-dichlorophenyl)-1H-pyrrol-3-yl]carbonyl}-O-(tert-butyl)-L-serine | 594.5 |
| 171 | 4-(2,4-dichlorophenyl)-N-[(2S)-2-hydroxypropyl]-1-(3-{[5-(trifluoromethyl)pyridin-2-yl]amino}propyl)-1H-pyrrole-3-carboxamide | 516.4 |
| 172 | 1-{3-[(6-amino-5-nitropyridin-2-yl)amino]propyl}-N-(1H-benzimidazol-2-ylmethyl)-4-(2,4-dichlorophenyl)-1H-pyrrole-3-carboxamide | 580.4 |
| 173 | 1-{3-[(6-amino-5-nitropyridin-2-yl)amino]propyl}-4-(4-bromo-2-fluorophenyl)-N-[(2R)-2-hydroxypropyl]-1H-pyrrole-3-carboxamide | 536.4 |
| 174 | 1-{3-[(6-amino-5-nitropyridin-2-yl)amino]propyl}-4-(2,4-difluorophenyl)-N-[(2S)-2-hydroxypropyl]-1H-pyrrole-3-carboxamide | 475.5 |
| 175 | 1-{3-[(5-cyanopyridin-2-yl)amino]propyl}-4-(2,4-dichloro-phenyl)-1H-pyrrole-3-carboxylic acid | 416.3 |
| 176 | 1-{3-[(6-amino-5-nitropyridin-2-yl)amino]propyl}-4-(4-cyano-phenyl)-N-[(2S)-2-hydroxypropyl]-1H-pyrrole-3-carboxamide | 464.5 |
| 177 | 1-{3-[(6-amino-5-nitropyridin-2-yl)amino]propyl}-4-(4-bromo-2-fluorophenyl)-N-[(2S)-2-hydroxypropyl]-1H-pyrrole-3-carboxamide | 536.4 |
| 178 | 1-{3-[(6-amino-5-nitropyridin-2-yl)amino]propyl}-N-[(3S,4S)-1-azabicyclo[2.2.1]hept-3-yl]-4-(2,4-dichlorophenyl)-1H-pyrrole-3-carboxamide | 545.4 |
| 179 | 1-{3-[(6-amino-5-nitropyridin-2-yl)amino]propyl}-4-(4-bromo-2-fluorophenyl)-N-[(1S)-2-hydroxy-1-methylethyl]-1H-pyrrole-3-carboxamide | 536.4 |
| 180 | 1-({1-{3-[(6-amino-5-nitropyridin-2-yl)amino]propyl}-4-[4-(1H-imidazol-1-yl)phenyl]-1H-pyrrol-3-yl}carbonyl)piperidine-4-carboxamide | 558.6 |
| 181 | N-1-[1-{3-[(6-amino-5-nitropyridin-2-yl)amino]propyl}-4-(4-ethylphenyl)-1H-pyrrol-3-yl]-N-2-(2-hydroxyethyl)glycinamide | 482.6 |
| 182 | tert-butyl 1-{3-[(6-amino-5-nitropyridin-2-yl)amino]propyl}-4-(4-ethylphenyl)-1H-pyrrole-3-carboxylate | 466.6 |
| 183 | 1-{3-[(6-amino-5-nitropyridin-2-yl)amino]propyl}-N-[(2S)-2-hydroxypropyl]-4-[4-(trifluoromethoxy)phenyl]-1H-pyrrole-3-carboxamide | 523.5 |
| 184 | 1-{3-[(6-amino-5-nitropyridin-2-yl)amino]propyl}-4-(4-chloro-2-fluorophenyl)-N-[(2R)-2-hydroxypropyl]-1H-pyrrole-3-carboxamide | 491.9 |
| 185 | N-[1-{3-[(6-amino-5-nitropyridin-2-yl)amino]propyl}-4-(4-ethyl-phenyl)-1H-pyrrol-3-yl]-2-methoxyacetamide | 453.5 |
| 186 | N-6-{3-[3-(2,4-dichlorophenyl)-4-(morpholin-4-ylcarbonyl)-1H-pyrrol-1-yl]propyl}-3-nitropyridine-2,6-diamine | 520.4 |
| 187 | 1-(2-{[1-{3-[(6-amino-5-nitropyridin-2-yl)amino]propyl}-4-(4-ethylphenyl)-1H-pyrrol-3-yl]amino}-2-oxoethyl)piperidine-4-carboxylic acid | 550.6 |
| 188 | N-6-(3-{3-{[(3R)-3-(dimethylamino)pyrrolidin-1-yl]carbonyl}-4-[4-(1H-imidazol-1-yl)phenyl]-1H-pyrrol-1-yl}propyl)-3-nitropyridine-2,6-diamine | 544.6 |
| 189 | 1-{3-[(6-amino-5-nitropyridin-2-yl)amino]propyl}-4-(4-bromo-phenyl)-N-[(1R)-2-hydroxy-1-methylethyl]-1H-pyrrole-3-carboxamide | 518.4 |
| 190 | tert-butyl 5-[N-(1-{3-[(6-amino-5-nitro(2-pyridyl))amino]propyl}-4-(4-ethylphenyl)pyrrol-3-yl)carbamoyl]-3-hydroxypyrrolidine-carboxylate | 594.7 |
| 191 | 1-{3-[(6-amino-5-nitropyridin-2-yl)amino]propyl}-4-(4-chloro-phenyl)-N-[(1R)-2-hydroxy-1-methylethyl]-1H-pyrrole-3-carboxamide | 473.9 |
| 192 | 1-{3-[(6-amino-5-nitropyridin-2-yl)amino]propyl}-3-(2,4-dichlorophenyl)-N-(2-pyridin-4-ylethyl)-1H-pyrrole-2-carboxamide | 555.4 |

| EXAMPLE | NAME | MH+ |
|---|---|---|
| 193 | 1-{3-[(6-amino-5-nitropyridin-2-yl)amino]propyl}-4-(4-chloro-phenyl)-N-[(2S)-2-hydroxypropyl]-1H-pyrrole-3-carboxamide | 473.9 |
| 194 | 1-{3-[(6-amino-5-nitropyridin-2-yl)amino]propyl}-N-[(1R)-2-hydroxy-1-methylethyl]-4-(4-methoxyphenyl)-1H-pyrrole-3-carboxamide | 469.5 |
| 195 | 1-{3-[(6-amino-5-nitropyridin-2-yl)amino]propyl}-4-(4-fluoro-phenyl)-N-[(1R)-2-hydroxy-1-methylethyl]-1H-pyrrole-3-carboxamide | 457.5 |
| 196 | 1-{3-[(6-amino-5-nitropyridin-2-yl)amino]propyl}-N-[(2R)-2-hydroxypropyl]-4-[4-(trifluoromethoxy)phenyl]-1H-pyrrole-3-carboxamide | 523.5 |
| 197 | tert-butyl 1-{3-[(6-amino-5-nitropyridin-2-yl)amino]propyl}-4-(4-cyanophenyl)-1H-pyrrole-3-carboxylate | 463.5 |
| 198 | N-1-[1-{3-[(6-amino-5-nitropyridin-2-yl)amino]propyl}-4-(4-ethylphenyl)-1H-pyrrol-3-yl]-N-2-(3-methoxypropyl)glycinamide | 510.6 |
| 199 | 1-{3-[(6-amino-5-nitropyridin-2-yl)amino]propyl}-4-(2,4-dichlorophenyl)-N-[(2-phenyl-1H-imidazol-4-yl)methyl]-1H-pyrrole-3-carboxamide | 606.5 |
| 200 | 1-{3-[(6-amino-5-nitropyridin-2-yl)amino]propyl}-4-(2,4-dichlorophenyl)-N-(quinolin-2-ylmethyl)-1H-pyrrole-3-carboxamide | 591.5 |
| 201 | N-[1-{3-[(6-amino-5-nitropyridin-2-yl)amino]propyl}-4-(4-ethyl-phenyl)-1H-pyrrol-3-yl]-2-morpholin-4-ylacetamide | 508.6 |
| 202 | 1-{3-[(6-amino-5-nitropyridin-2-yl)amino]propyl}-4-(4-fluoro-phenyl)-N-[(2R)-2-hydroxypropyl]-1H-pyrrole-3-carboxamide | 457.5 |
| 203 | 1-{3-[(6-amino-5-nitropyridin-2-yl)amino]propyl}-4-(4-cyano-phenyl)-1H-pyrrole-3-carboxylic acid | 407.4 |
| 204 | N-6-{3-[3-amino-4-(2,4-dichlorophenyl)-1H-pyrrol-1-yl]propyl}-3-nitropyridine-2,6-diamine | 422.3 |
| 205 | 1-{3-[(6-amino-5-nitropyridin-2-yl)amino]propyl}-4-(4-fluoro-phenyl)-N-[(2S)-2-hydroxypropyl]-1H-pyrrole-3-carboxamide | 457.5 |
| 206 | 1-{3-[(6-amino-5-nitropyridin-2-yl)amino]propyl}-N-benzyl-4-(2,4-dichlorophenyl)-1H-pyrrole-3-carboxamide | 540.4 |
| 207 | 1-{3-[(6-amino-5-nitropyridin-2-yl)amino]propyl}-4-(2,4-dichlorophenyl)-N-[(5-methylpyrazin-2-yl)methyl]-1H-pyrrole-2-carboxamide | 556.4 |
| 208 | 1-{3-[(6-amino-5-nitropyridin-2-yl)amino]propyl}-N-[(2S)-2-hydroxypropyl]-4-(4-methylphenyl)-1H-pyrrole-3-carboxamide | 453.5 |
| 209 | 2-(3-acetyl-1H-pyrrol-1-yl)-N-[1-{3-[(6-amino-5-nitropyridin-2-yl)amino]propyl}-4-(2,4-dichlorophenyl)-1H-pyrrol-3-yl]-acetamide | 571.4 |
| 210 | 1-{3-[(6-amino-5-nitropyridin-2-yl)amino]propyl}-4-(2,4-dichlorophenyl)-N-(3-morpholin-4-ylpropyl)-1H-pyrrole-2-carboxamide | 577.5 |
| 211 | N-2-(3-aminocyclohexyl)-N-1-[1-{3-[(6-amino-5-nitropyridin-2-yl)amino]propyl}-4-(4-ethylphenyl)-1H-pyrrol-3-yl]glycinamide | 535.7 |
| 212 | 1-{3-[(6-amino-5-nitropyridin-2-yl)amino]propyl}-N-[(1S)-2-hydroxy-1-methylethyl]-4-[4-(trifluoromethoxy)phenyl]-1H-pyrrole-3-carboxamide | 523.5 |
| 213 | N-[1-{3-[(6-amino-5-nitropyridin-2-yl)amino]propyl}-4-(2,4-dichlorophenyl)-1H-pyrrol-3-yl]-2-(1,4'-bipiperidin-1'-yl)-acetamide | 630.6 |
| 214 | 1-{3-[(6-amino-5-nitropyridin-2-yl)amino]propyl}-4-(4-fluoro-phenyl)-N-[(1S)-2-hydroxy-1-methylethyl]-1H-pyrrole-3-carboxamide | 457.5 |
| 215 | 1-{3-[(6-amino-5-nitropyridin-2-yl)amino]propyl}-4-(2,4-dichlorophenyl)-N-[2-(1H-indol-3-yl)ethyl]-1H-pyrrole-3-carboxamide | 593.5 |
| 216 | 1-{3-[(6-amino-5-nitropyridin-2-yl)amino]propyl}-N-[(2S)-2-hydroxypropyl]-4-(4-methoxyphenyl)-1H-pyrrole-3-carboxamide | 469.5 |
| 217 | N-[1-{3-[(6-amino-5-nitropyridin-2-yl)amino]propyl}-4-(4-ethylphenyl)-1H-pyrrol-3-yl]-2-(1H-imidazol-1-yl)acetamide | 489.5 |
| 218 | 1-{3-[(6-amino-5-nitropyridin-2-yl)amino]propyl}-4-(2,4-dichlorophenyl)-N-(pyridin-2-ylmethyl)-1H-pyrrole-2-carboxamide | 541.4 |
| 219 | N-1-[1-{3-[(6-amino-5-nitropyridin-2-yl)amino]propyl}-4-(4-ethylphenyl)-1H-pyrrol-3-yl]ornithinamide | 495.6 |
| 220 | N-1-[1-{3-[(6-amino-5-nitropyridin-2-yl)amino]propyl}-4-(4-ethylphenyl)-1H-pyrrol-3-yl]-N-2-,N-2-dimethylglycinamide | 466.6 |
| 221 | 1-{3-[(6-amino-5-nitropyridin-2-yl)amino]propyl}-4-(3-chloro-phenyl)-N-[(1R)-2-hydroxy-1-methylethyl]-1H-pyrrole-3-carboxamide | 473.9 |
| 222 | N-[1-{3-[(6-amino-5-nitropyridin-2-yl)amino]propyl}-4-(4-ethyl-phenyl)-1H-pyrrol-3-yl]methanesulfonamide | 459.5 |
| 223 | 1-{3-[(6-amino-5-nitropyridin-2-yl)amino]propyl}-N-[(1S)-2-hydroxy-1-methylethyl]-4-(4-methylphenyl)-1H-pyrrole-3-carboxamide | 453.5 |

-continued

| EXAMPLE | NAME | MH+ |
|---|---|---|
| 224 | 1-{3-[(6-amino-5-nitropyridin-2-yl)amino]propyl}-4-(2,4-dichlorophenyl)-N-[2-(1-methylpyrrolidin-2-yl)ethyl]-1H-pyrrole-2-carboxamide | 561.5 |
| 225 | 1-{3-[(6-amino-5-nitropyridin-2-yl)amino]propyl}-N-[(2R)-2-hydroxypropyl]-4-(4-methoxyphenyl)-1H-pyrrole-3-carboxamide | 469.5 |
| 226 | 2-amino-N-[1-{3-[(6-amino-5-nitropyridin-2-yl)amino]propyl}-4-(4-ethylphenyl)-1H-pyrrol-3-yl]-4-(methylsulfinyl)butanamide | 528.6 |
| 227 | N-[1-{3-[(6-amino-5-nitropyridin-2-yl)amino]propyl}-4-(4-ethylphenyl)-1H-pyrrol-3-yl]-2-pyrrolidin-1-ylacetamide | 492.6 |
| 228 | N-6-(3-{3-[4-(1H-imidazol-1-yl)phenyl]-4-[(4-methylpiperazin-1-yl)carbonyl]-1H-pyrrol-1-yl}propyl)-3-nitropyridine-2,6-diamine | 530.6 |
| 229 | N-6-{3-[4-(2,4-dichlorophenyl)-2-(morpholin-4-ylcarbonyl)-1H-pyrrol-1-yl]propyl}-3-nitropyridine-2,6-diamine | 520.4 |
| 230 | 1-{3-[(6-amino-5-nitropyridin-2-yl)amino]propyl}-N-[(2R)-2-hydroxypropyl]-4-(4-methylphenyl)-1H-pyrrole-3-carboxamide | 453.5 |
| 231 | tert-butyl 1-{3-[(6-amino-5-nitropyridin-2-yl)amino]propyl}-4-(4-chloro-2-fluorophenyl)-1H-pyrrole-3-carboxylate | 490.9 |
| 232 | N-[1-{3-[(6-amino-5-nitropyridin-2-yl)amino]propyl}-4-(4-ethylphenyl)-1H-pyrrol-3-yl]-2-[(3S)-3-(dimethylamino)pyrrolidin-1-yl]acetamide | 535.7 |
| 233 | tert-butyl 1-{3-[(6-amino-5-nitropyridin-2-yl)amino]propyl}-4-(4-bromo-2-fluorophenyl)-1H-pyrrole-3-carboxylate | 535.4 |
| 234 | N-[1-{3-[(6-amino-5-nitropyridin-2-yl)amino]propyl}-4-(4-ethylphenyl)-1H-pyrrol-3-yl]benzamide | 485.6 |
| 235 | 1-{3-[(6-amino-5-nitropyridin-2-yl)amino]propyl}-N-(1-benzylpiperidin-4-yl)-4-(2,4-dichlorophenyl)-1H-pyrrole-3-carboxamide | 623.6 |
| 236 | 1-{3-[(6-amino-5-nitropyridin-2-yl)amino]propyl}-N-[(1S)-2-hydroxy-1-methylethyl]-4-(4-methoxyphenyl)-1H-pyrrole-3-carboxamide | 469.5 |
| 237 | N-[1-{3-[(6-amino-5-nitropyridin-2-yl)amino]propyl}-4-(2,4-dichlorophenyl)-1H-pyrrol-3-yl]-N'-(pyridin-3-ylmethyl)urea | 556.4 |
| 238 | 1-{3-[(6-amino-5-nitropyridin-2-yl)amino]propyl}-N-[(1S)-1-benzyl-2-hydroxyethyl]-4-(2,4-dichlorophenyl)-1H-pyrrole-3-carboxamide | 584.5 |
| 239 | 2-(3-acetyl-1H-pyrrol-1-yl)-N-[1-{3-[(6-amino-5-nitropyridin-2-yl)amino]propyl}-4-(4-ethylphenyl)-1H-pyrrol-3-yl]acetamide | 530.6 |
| 240 | tert-butyl 1-{3-[(6-amino-5-nitropyridin-2-yl)amino]propyl}-4-(2,4-difluorophenyl)-1H-pyrrole-3-carboxylate | 474.5 |
| 241 | 1-{3-[(6-amino-5-nitropyridin-2-yl)amino]propyl}-4-(2,4-dichlorophenyl)-N-[(5-methyl-3-phenylisoxazol-4-yl)methyl]-1H-pyrrole-3-carboxamide | 621.5 |
| 242 | N-(1-{3-[(6-amino-5-nitro(2-pyridyl))amino]propyl}-4-(2,4-dichlorophenyl)pyrrol-3-yl)-2,5-bis[(tert-butoxy)carbonylamino]-pentanamide | 736.7 |
| 243 | 1-{3-[(6-amino-5-nitropyridin-2-yl)amino]propyl}-3-(2,4-dichlorophenyl)-N-(2-morpholin-4-ylethyl)-1H-pyrrole-2-carboxamide | 563.5 |
| 244 | 1-{3-[(6-amino-5-nitropyridin-2-yl)amino]propyl}-4-(4-bromophenyl)-N-[(2R)-2-hydroxypropyl]-1H-pyrrole-3-carboxamide | 518.4 |
| 245 | 1-{3-[(6-amino-5-nitropyridin-2-yl)amino]propyl}-4-(4-bromophenyl)-N-[(2S)-2-hydroxypropyl]-1H-pyrrole-3-carboxamide | 518.4 |
| 246 | 1-{3-[(6-amino-5-nitropyridin-2-yl)amino]propyl}-N-[(1R)-2-hydroxy-1-methylethyl]-4-[4-(trifluoromethyl)phenyl]-1H-pyrrole-3-carboxamide | 507.5 |
| 247 | 1-{3-[(6-amino-5-nitropyridin-2-yl)amino]propyl}-4-(4-chlorophenyl)-N-[(2R)-2-hydroxypropyl]-1H-pyrrole-3-carboxamide | 473.9 |
| 248 | N-[1-{3-[(6-amino-5-nitropyridin-2-yl)amino]propyl}-4-(4-ethylphenyl)-1H-pyrrol-3-yl]-2-(1,4'-bipiperidin-1'-yl)acetamide | 589.8 |
| 249 | tert-butyl 4-(2,4-dichlorophenyl)-1-(3-{[5-(trifluoromethyl)-pyridin-2-yl]amino}propyl)-1H-pyrrole-3-carboxylate | 515.4 |
| 250 | 1-{3-[(6-amino-5-nitropyridin-2-yl)amino]propyl}-4-(4-chlorophenyl)-N-[(1S)-2-hydroxy-1-methylethyl]-1H-pyrrole-3-carboxamide | 473.9 |
| 251 | N-[1-{3-[(6-amino-5-nitropyridin-2-yl)amino]propyl}-4-(4-ethylphenyl)-1H-pyrrol-3-yl]-2-[(3R)-3-(dimethylamino)-pyrrolidin-1-yl]acetamide | 535.7 |
| 252 | tert-butyl 1-{3-[(6-amino-5-nitropyridin-2-yl)amino]propyl}-4-(4-methylphenyl)-1H-pyrrole-3-carboxylate | 452.5 |
| 253 | 1-{3-[(6-amino-5-nitropyridin-2-yl)amino]propyl}-4-(4-bromophenyl)-N-[(1S)-2-hydroxy-1-methylethyl]-1H-pyrrole-3-carboxamide | 518.4 |
| 254 | 1-{3-[(6-amino-5-nitropyridin-2-yl)amino]propyl}-4-(3-chlorophenyl)-N-[(2S)-2-hydroxypropyl]-1H-pyrrole-3-carboxamide | 473.9 |
| 255 | 1-{3-[(6-amino-5-nitropyridin-2-yl)amino]propyl}-4-(2,4-dichlorophenyl)-N-[4-(dimethylamino)benzyl]-1H-pyrrole-2-carboxamide | 583.5 |

-continued

| EXAMPLE | NAME | MH+ |
|---|---|---|
| 256 | 1-{3-[(6-amino-5-nitropyridin-2-yl)amino]propyl}-4-(2,4-dichlorophenyl)-N-(2-methoxyethyl)-1H-pyrrole-2-carboxamide | 508.4 |
| 257 | N-(1-{3-[(6-amino-5-nitro(2-pyridyl))amino]propyl}-4-(2,4-dichlorophenyl)pyrrol-3-yl)-3-(tert-butoxy)-2-[(tert-butoxy)carbonylamino]propanamide | 665.6 |
| 258 | tert-butyl 1-{3-[(6-amino-5-nitropyridin-2-yl)amino]propyl}-4-(4-methoxyphenyl)-1H-pyrrole-3-carboxylate | 468.5 |
| 259 | 1-{3-[(6-amino-5-nitropyridin-2-yl)amino]propyl}-N-[(2R)-2-hydroxypropyl]-4-[4-(trifluoromethyl)phenyl]-1H-pyrrole-3-carboxamide | 507.5 |
| 260 | 1-{3-[(6-amino-5-nitropyridin-2-yl)amino]propyl}-4-(2,4-dichlorophenyl)-N-(2-pyrrolidin-1-ylethyl)-1H-pyrrole-2-carboxamide | 547.5 |
| 261 | 1-{3-[(6-amino-5-nitropyridin-2-yl)amino]propyl}-4-(3-chlorophenyl)-N-[(2R)-2-hydroxypropyl]-1H-pyrrole-3-carboxamide | 473.9 |
| 262 | N-1-[1-{3-[(6-amino-5-nitropyridin-2-yl)amino]propyl}-4-(4-ethylphenyl)-1H-pyrrol-3-yl]-N-2-[2-(dimethylamino)ethyl]-glycinamide | 509.6 |
| 263 | 1-{3-[(6-amino-5-nitropyridin-2-yl)amino]propyl}-4-(2,4-dichlorophenyl)-N-(2-morpholin-4-ylethyl)-1H-pyrrole-2-carboxamide | 563.5 |
| 264 | N-6-{3-[3-amino-4-(4-ethylphenyl)-1H-pyrrol-1-yl]propyl}-3-nitropyridine-2,6-diamine | 381.4 |
| 265 | 1-{3-[(6-amino-5-nitropyridin-2-yl)amino]propyl}-3-(2,4-dichlorophenyl)-N-[3-(1H-imidazol-1-yl)propyl]-1H-pyrrole-2-carboxamide | 558.4 |
| 266 | N-[1-{3-[(6-amino-5-nitropyridin-2-yl)amino]propyl}-4-(2,4-dichlorophenyl)-1H-pyrrol-3-yl]-2-azepan-1-ylacetamide | 561.5 |
| 267 | 1-{3-[(6-amino-5-nitropyridin-2-yl)amino]propyl}-3-(2,4-dichlorophenyl)-N-(2-pyridin-3-ylethyl)-1H-pyrrole-2-carboxamide | 555.4 |
| 268 | 1-{3-[(6-amino-5-nitropyridin-2-yl)amino]propyl}-4-(3-chlorophenyl)-N-[(1S)-2-hydroxy-1-methylethyl]-1H-pyrrole-3-carboxamide | 473.9 |
| 269 | N-[1-{3-[(6-amino-5-nitropyridin-2-yl)amino]propyl}-4-(4-ethylphenyl)-1H-pyrrol-3-yl]acetamide | 561.5 |
| 270 | 1-{3-[(6-amino-5-nitropyridin-2-yl)amino]propyl}-N-[(2S)-2-hydroxypropyl]-4-[4-(trifluoromethyl)phenyl]-1H-pyrrole-3-carboxamide | 507.5 |
| 271 | 1-{3-[(6-amino-5-nitropyridin-2-yl)amino]propyl}-4-(2,4-difluorophenyl)-1H-pyrrole-3-carboxylic acid | 418.4 |
| 272 | N-[1-{3-[(6-amino-5-nitropyridin-2-yl)amino]propyl}-4-(4-ethylphenyl)-1H-pyrrol-3-yl]acetamide | 423.5 |
| 273 | 1-{3-[(6-amino-5-nitropyridin-2-yl)amino]propyl}-4-(4-fluorophenyl)-1H-pyrrole-3-carboxylic acid | 400.4 |
| 274 | 1-{3-[(6-amino-5-nitropyridin-2-yl)amino]propyl}-4-(4-ethylphenyl)-1H-pyrrole-3-carboxylic acid | 410.4 |
| 275 | 1-{3-[(6-amino-5-nitropyridin-2-yl)amino]propyl}-3-(2,4-dichlorophenyl)-N-(2-pyridin-2-ylethyl)-1H-pyrrole-2-carboxamide | 555.4 |
| 276 | N-[1-{3-[(6-amino-5-nitropyridin-2-yl)amino]propyl}-4-(4-ethylphenyl)-1H-pyrrol-3-yl]-2-azepan-1-ylacetamide | 520.6 |
| 277 | 1-{3-[(6-amino-5-nitropyridin-2-yl)amino]propyl}-4-(4-chloro-2-methoxyphenyl)-N-(2-hydroxyethyl)-1H-pyrrole-3-carboxamide | 489.9 |
| 278 | 1-{3-[(6-amino-5-nitropyridin-2-yl)amino]propyl}-4-(2,4-dichlorophenyl)-N-(2-pyridin-4-ylethyl)-1H-pyrrole-2-carboxamide | 555.4 |
| 279 | 1-{3-[(6-amino-5-nitropyridin-2-yl)amino]propyl}-4-(4-methoxyphenyl)-1H-pyrrole-3-carboxylic acid | 412.4 |
| 280 | 1-{3-[(6-amino-5-nitropyridin-2-yl)amino]propyl}-N-[(1S)-2-hydroxy-1-methylethyl]-4-[4-(trifluoromethyl)phenyl]-1H-pyrrole-3-carboxamide | 507.5 |
| 281 | N-[1-{3-[(6-amino-5-nitropyridin-2-yl)amino]propyl}-4-(4-ethylphenyl)-1H-pyrrol-3-yl]tetrahydrofuran-3-carboxamide | 479.6 |
| 282 | 1-{3-[(6-amino-5-nitropyridin-2-yl)amino]propyl}-4-[2-fluoro-4-(trifluoromethyl)phenyl]-N-[(1R)-2-hydroxy-1-methylethyl]-1H-pyrrole-3-carboxamide | 525.5 |
| 283 | 1-{3-[-(6-amino-5-nitropyridin-2-yl)amino]propyl}-4-(2,4-dichlorophenyl)-N-[4-(dimethylamino)benzyl]-1H-pyrrole-3-carboxamide | 583.5 |
| 284 | 1-{3-[(6-amino-5-nitropyridin-2-yl)amino]propyl}-4-(2,4-dichlorophenyl)-N-(2-furylmethyl)-1H-pyrrole-2-carboxamide | 530.4 |
| 285 | 2-pyridin-3-ylethyl 1-{3-[(6-amino-5-nitropyridin-2-yl)amino]-propyl}-4-(2,4-diclorophenyl)-1H-pyrrole-2-carboxamide | 556.4 |
| 286 | 1-{3-[(6-amino-5-nitropyridin-2-yl)amino]propyl}-3-(2,4-dichlorophenyl)-N-(2-methoxyethyl)-1H-pyrrole-2-carboxamide | 508.4 |

-continued

| EXAMPLE | NAME | MH+ |
|---|---|---|
| 287 | tert-butyl 1-{3-[(6-amino-5-nitropyridin-2-yl)amino]propyl}-4-[4-(trifluoromethoxy)phenyl]-1H-pyrrole-3-carboxylate | 522.5 |
| 288 | N-6-{3-[3-(2,4-dichlorophenyl)-4-nitro-1H-pyrrol-1-yl]propyl}-3-nitropyridine-2,6-diamine | 452.3 |
| 289 | N-(1-{3-[(6-amino-5-nitro(2-pyridyl))amino]propyl}-4-(4-ethylphenyl)pyrrol-3-yl)-3-(tert-butoxy)-2-[(tert-butoxy)carbonylamino]propanamide | 624.8 |
| 290 | 1-{3-[(6-amino-5-nitropyridin-2-yl)amino]propyl}-4-(2,4-dichlorophenyl)-N-[3-(1H-imidazol-1-yl)propyl]-1H-pyrrole-2-carboxamide | 558.4 |
| 291 | 1-{3-[(6-amino-5-nitropyridin-2-yl)amino]propyl}-3-(2,4-dichlorophenyl)-N-(3-pyrrolidin-1-ylpropyl)-1H-pyrrole-2-carboxamide | 561.5 |
| 292 | tert-butyl 1-{3-[(6-amino-5-nitropyridin-2-yl)amino]propyl}-4-(4-bromophenyl)-1H-pyrrole-3-carboxylate | 517.4 |
| 293 | N-(1-{3-[(6-amino-5-nitro(2-pyridyl))amino]propyl}-4-(4-ethylphenyl)pyrrol-3-yl)-2,5-bis[(tert-butoxy)carbonylamino]-pentanamide | 695.8 |
| 294 | 1-{3-[(6-amino-5-nitropyridin-2-yl)amino]propyl}-4-(4-chloro-2-fluorophenyl)-1H-pyrrole-3-carboxylic acid | 434.8 |
| 295 | tert-butyl 1-{3-[(6-amino-5-nitropyridin-2-yl)amino]propyl}-4-(4-chlorophenyl)-1H-pyrrole-3-carboxylate | 472.9 |
| 296 | 1-{3-[(6-amino-5-nitropyridin-2-yl)amino]propyl}-4-[4-(trifluoromethoxy)phenyl]-1H-pyrrole-3-carboxylic acid | 466.4 |
| 297 | ethyl N-{[1-{3-[(6-amino-5-nitropyridin-2-yl)amino]propyl}-4-(2,4-dichlorophenyl)-1H-pyrrol-2-yl]carbonyl}glycinate | 536.4 |
| 298 | 1-{3-[(6-amino-5-nitropyridin-2-yl)amino]propyl}-4-(2,4-dichlorophenyl)-N-(pyridin-3-ylmethyl)-1H-pyrrole-2-carboxamide | 541.4 |
| 299 | 1-{3-[(6-amino-5-nitropyridin-2-yl)amino]propyl}-4-(4-methylphenyl)-1H-pyrrole-3-carboxylic acid | 396.4 |
| 300 | 1-{3-[(6-amino-5-nitropyridin-2-yl)amino]propyl}-4-(4-chlorophenyl)-1H-pyrrole-3-carboxylic acid | 416.8 |
| 301 | 1-{3-[(6-amino-5-nitropyridin-2-yl)amino]propyl}-N-benzyl-4-(2,4-dichlorophenyl)-1H-pyrrole-2-carboxamide | 540.4 |
| 302 | 1-{3-[(6-amino-5-nitropyridin-2-yl)amino]propyl}-4-[2-fluoro-4-(trifluoromethyl)phenyl]-N-[(2S)-2-hydroxypropyl]-1H-pyrrole-3-carboxamide | 525.5 |
| 303 | 1-{3-[(6-amino-5-nitropyridin-2-yl)amino]propyl}-4-(2,4-dichlorophenyl)-N-(2-pyridin-2-ylethyl)-1H-pyrrole-2-carboxamide | 555.4 |
| 304 | 1-{3-[(6-amino-5-nitropyridin-2-yl)amino]propyl}-3-(2,4-dichlorophenyl)-N-[(5-methylpyrazin-2-yl)methyl]-1H-pyrrole-2-carboxamide | 556.4 |
| 305 | 1-{3-[(6-amino-5-nitropyridin-2-yl)amino]propyl}-4-[2-fluoro-4-(trifluoromethyl)phenyl]-N-[(2R)-2-hydroxypropyl]-1H-pyrrole-3-carboxamide | 525.5 |
| 306 | 1-{3-[(6-amino-5-nitropyridin-2-yl)amino]propyl}-3-(2,4-dichlorophenyl)-N-(pyridin-4-ylmethyl)-1H-pyrrole-2-carboxamide | 541.4 |
| 307 | N-6-[3-(4-(2,4-dichlorophenyl)-2-{[(2S)-2-(pyrrolidin-1-ylmethyl)pyrrolidin-1-yl]carbonyl}-1H-pyrrol-1-yl)propyl]-3-nitropyridine-2,6-diamine | 587.5 |
| 308 | tert-butyl 1-{3-[(6-amino-5-nitropyridin-2-yl)amino]propyl}-4-(4-fluorophenyl)-1H-pyrrole-3-carboxylate | 456.5 |
| 309 | 4-(2,4-dichlorophenyl)-1-(3-{[5-(trifluoromethyl)pyridin-2-yl]amino}propyl)-1H-pyrrole-3-carboxylic acid | 459.3 |
| 310 | 1-{3-[(6-amino-5-nitropyridin-2-yl)amino]propyl}-N-(1H-benzimidazol-2-ylmethyl)-4-(2,4-dichlorophenyl)-1H-pyrrole-2-carboxamide | 580.4 |
| 311 | 1-{3-[(6-amino-5-nitropyridin-2-yl)amino]propyl}-3-(2,4-dichlorophenyl)-N-(pyridin-3-ylmethyl)-1H-pyrrole-2-carboxamide | 541.4 |
| 312 | N-6-(3-{3-(1,4'-bipiperidin-1'-ylcarbonyl)-4-[4-(1H-imidazol-1-yl)phenyl]-1H-pyrrol-1-yl}propyl)-3-nitropyridine-2,6-diamine | 598.7 |
| 313 | 1-{3-[(6-amino-5-nitropyridin-2-yl)amino]propyl}-4-(4-bromophenyl)-1H-pyrrole-3-carboxylic acid | 461.3 |
| 314 | 1-{3-[(6-amino-5-nitropyridin-2-yl)amino]propyl}-4-[2-fluoro-4-(trifluoromethyl)phenyl]-N-[(1S)-2-hydroxy-1-methylethyl]-1H-pyrrole-3-carboxamide | 525.5 |
| 315 | 1-{3-[(6-amino-5-nitropyridin-2-yl)amino]propyl}-4-(2,4-dichlorophenyl)-N-(3-pyrrolidin-1-ylpropyl)-1H-pyrrole-2-carboxamide | 561.5 |
| 316 | 1-{3-[(6-amino-5-nitropyridin-2-yl)amino]propyl}-3-(2,4-dichlorophenyl)-N-ethyl-N-(pyridin-4-ylmethyl)-1H-pyrrole-2-carboxamide | 569.5 |

-continued

| EXAMPLE | NAME | MH+ |
|---|---|---|
| 317 | 1-{3-[(6-amino-5-nitropyridin-2-yl)amino]propyl}-3-(2,4-dichlorophenyl)-N-(2-hydroxyethyl)-1H-pyrrole-2-carboxamide | 494.3 |
| 318 | 1-{3-[(6-amino-5-nitropyridin-2-yl)amino]propyl}-4-(2,4-dichlorophenyl)-N-(pyridin-4-ylmethyl)-1H-pyrrole-2-carboxamide | 541.4 |
| 319 | 1-{3-[(6-amino-5-nitropyridin-2-yl)amino]propyl}-4-(4-bromo-2-fluorophenyl)-1H-pyrrole-3-carboxylic acid | 479.3 |
| 320 | tert-butyl 1-{3-[(6-amino-5-nitropyridin-2-yl)amino]propyl}-4-(4-ethylphenyl)-1H-pyrrol-3-ylcarbamate | 481.6 |
| 321 | N-6-{2-[3-(2,4-dichlorophenyl)-4-nitro-1H-pyrrol-1-yl]ethyl}-3-nitropyridine-2,6-diamine | 438.2 |
| 322 | 1-{3-[(6-amino-5-nitropyridin-2-yl)amino]propyl}-3-(2,4-dichlorophenyl)-1H-pyrrole-2-carboxylic acid | 451.3 |
| 323 | 1-{3-[(6-amino-5-nitropyridin-2-yl)amino]propyl}-3-(2,4-dichlorophenyl)-N-(pyridin-2-ylmethyl)-1H-pyrrole-2-carboxamide | 541.4 |
| 324 | 1-{3-[(6-amino-5-nitropyridin-2-yl)amino]propyl}-N-benzyl-3-(2,4-dichlorophenyl)-1H-pyrrole-2-carboxamide | 540.4 |
| 325 | N-6-[3-(3-(2,4-dichlorophenyl)-2-{[(2S)-2-(pyrrolidin-1-ylmethyl)pyrrolidin-1-yl]carbonyl}-1H-pyrrol-1-yl)propyl]-3-nitropyridine-2,6-diamine | 587.5 |
| 326 | 1-{3-[(6-amino-5-nitropyridin-2-yl)amino]propyl}-3-(2,4-dichlorophenyl)-N-(2-furylmethyl)-1H-pyrrole-2-carboxamide | 530.4 |
| 327 | N-6-{3-[3-(2,4-dichlorophenyl)-2-(morpholin-4-ylcarbonyl)-1H-pyrrol-1-yl]propyl}-3-nitropyridine-2,6-diamine | 520.4 |
| 328 | 1-{3-[(6-amino-5-nitropyridin-2-yl)amino]propyl}-3-(2,4-dichlorophenyl)-N-[4-(dimethylamino)benzyl]-1H-pyrrole-2-carboxamide | 583.5 |
| 329 | 1-{3-[(6-amino-5-nitropyridin-2-yl)amino]propyl}-N-(1H-benzimidazol-2-ylmethyl)-3-(2,4-dichlorophenyl)-1H-pyrrole-2-carboxamide | 580.4 |
| 330 | 1-{3-[(6-amino-5-nitropyridin-2-yl)amino]propyl}-4-(2,4-dichlorophenyl)-1H-pyrrole-2-carboxylic acid | 451.3 |
| 331 | 1-{3-[(6-amino-5-nitropyridin-2-yl)amino]propyl}-3-(2,4-dichlorophenyl)-N-(2-pyrrolidin-1-ylethyl)-1H-pyrrole-2-carboxamide | 547.5 |
| 332 | 1-{3-[(6-amino-5-nitropyridin-2-yl)amino]propyl}-3-(2,4-dichlorophenyl)-N-[2-(1-methylpyrrolidin-2-yl)ethyl]-1H-pyrrole-2-carboxamide | 561.5 |
| 333 | 1-{3-[(6-amino-5-nitropyridin-2-yl)amino]propyl}-4-(2,4-dichlorophenyl)-N-methyl-N-(pyridin-4-ylmethyl)-1H-pyrrole-2-carboxamide | 555.4 |
| 334 | N-6-(3-{3-(2,4-dichlorophenyl)-2-[(2-phenylthiomorpholin-4-yl)carbonyl]-1H-pyrrol-1-yl}propyl)-3-nitropyridine-2,6-diamine | 612.6 |
| 335 | ethyl N-{[1-{3-[(6-amino-5-nitropyridin-2-yl)amino]propyl}-3-(2,4-dichlorophenyl)-1H-pyrrol-2-yl]carbonyl}glycinate | 536.4 |
| 336 | benzyl 4-(2,4-dichlorophenyl)-1-[3-(1,3-dioxo-1,3-dihydro-2H-isoindol-2-yl)propyl]-1H-pyrrole-2-carboxylate | 534.4 |
| 337 | benzyl 1-{3-[(6-amino-5-nitropyridin-2-yl)amino]propyl}-4-(2,4-dichlorophenyl)-1H-pyrrole-2-carboxylate | 541.4 |
| 338 | tert-butyl 1-{3-[(6-amino-5-nitropyridin-2-yl)amino]propyl}-4-(4-chloro-2-methoxyphenyl)-1H-pyrrole-3-carboxylate | 503.0 |
| 339 | 1-{3-[(6-amino-5-nitropyridin-2-yl)amino]propyl}-4-(4-chloro-2-methoxyphenyl)-1H-pyrrole-3-carboxylic acid | 446.9 |
| 340 | tert-butyl 2-({[1-{3-[(6-amino-5-nitropyridin-2-yl)amino]propyl}-4-(4-chloro-2-methoxyphenyl)-1H-pyrrol-3-yl]carbonyl}amino)ethylcarbamate | 589.1 |
| 341 | N-(2-aminoethyl)-1-{3-[(6-amino-5-nitropyridin-2-yl)amino]propyl}-4-(4-chloro-2-methoxyphenyl)-1H-pyrrole-3-carboxamide | 488.9 |
| 342 | 1-{3-[(6-amino-5-nitropyridin-2-yl)amino]propyl}-4-(4-chloro-2-methoxyphenyl)-N-(2-{[(4-cyanophenyl)sulfonyl]amino}ethyl)-1H-pyrrole-3-carboxamide | 654.1 |
| 343 | tert-butyl 1-{3-[(6-amino-5-nitropyridin-2-yl)amino]propyl}-4-[2-fluoro-4-(trifluoromethyl)phenyl]-1H-pyrrole-3-carboxylate | 524.5 |
| 344 | tert-butyl 1-{3-[(6-amino-5-nitropyridin-2-yl)amino]propyl}-4-(3-chlorophenyl)-1H-pyrrole-3-carboxylate | 472.9 |
| 345 | tert-butyl 1-{3-[(6-amino-5-nitropyridin-2-yl)amino]propyl}-4-[4-(trifluoromethyl)phenyl]-1H-pyrrole-3-carboxylate | 506.5 |
| 346 | 1-{3-[(6-amino-5-nitropyridin-2-yl)amino]propyl}-4-[2-fluoro-4-(trifluoromethyl)phenyl]-1H-pyrrole-3-carboxylic acid | 468.4 |
| 347 | 1-{3-[(6-amino-5-nitropyridin-2-yl)amino]propyl}-4-(3-chlorophenyl)-1H-pyrrole-3-carboxylic acid | 416.8 |
| 348 | 1-{3-[(6-amino-5-nitropyridin-2-yl)amino]propyl}-4-[4-(trifluoromethyl)phenyl]-1H-pyrrole-3-carboxylic acid | 450.4 |
| 349 | 1-{4-[(6-amino-5-nitropyridin-2-yl)amino]butyl}-4-(2,4-dichlorophenyl)-N-[(2S)-2-hydroxypropyl]-1H-pyrrole-3-carboxamide | 522.4 |

| EXAMPLE | NAME | MH+ |
|---|---|---|
| 350 | 1-{4-[(6-amino-5-nitropyridin-2-yl)amino]butyl}-4-(2,4-dichlorophenyl)-N-[(1S)-2-hydroxy-1-methylethyl]-1H-pyrrole-3-carboxamide | 522.4 |
| 351 | 1-{4-[(6-amino-5-nitropyridin-2-yl)amino]butyl}-4-(2,4-dichlorophenyl)-N-[(2R)-2-hydroxypropyl]-1H-pyrrole-3-carboxamide | 522.4 |
| 352 | 1-{4-[(6-amino-5-nitropyridin-2-yl)amino]butyl}-4-(2,4-dichlorophenyl)-N-[(1R)-2-hydroxy-1-methylethyl]-1H-pyrrole-3-carboxamide | 522.4 |
| 353 | tert-butyl 1-{4-[(6-amino-5-nitropyridin-2-yl)amino]butyl}-4-(2,4-dichlorophenyl)-1H-pyrrole-3-carboxylate | 521.4 |
| 354 | 1-{4-[(6-amino-5-nitropyridin-2-yl)amino]butyl}-4-(2,4-dichlorophenyl)-1H-pyrrole-3-carboxylic acid | 465.3 |
| 355 | 1-{3-[(6-amino-5-nitropyridin-2-yl)amino]propyl}-4-(2,4-dichlorophenyl)-N-(2-hydroxyethyl)-1H-pyrrole-2-carboxamide | 494.3 |
| 356 | 1-{3-[(6-amino-5-nitropyridin-2-yl)amino]propyl}-3-(2,4-dichlorophenyl)-N-(3-morpholin-4-ylpropyl)-1H-pyrrole-2-carboxamide | 577.5 |
| 357 | 6-({3-[3-(2,4-dichlorophenyl)-4-nitro-1H-pyrrol-1-yl]propyl}amino)nicotinonitrile | 417.3 |
| 358 | 1-{3-[(6-amino-5-nitropyridin-2-yl)amino]propyl}-4-(4-chloro-2-methoxyphenyl)-N-{2-[(phenylsulfonyl)amino]ethyl}-1H-pyrrole-3-carboxamide | 629.1 |
| 359 | 1-{3-[(6-amino-5-nitropyridin-2-yl)amino]propyl}-3-(2,4-dichlorophenyl)-N-(2-piperidin-1-ylethyl)-1H-pyrrole-2-carboxamide | 561.5 |
| 360 | 1-{3-[(6-amino-5-nitropyridin-2-yl)amino]propyl}-4-(4-chloro-2-methoxyphenyl)-N-(2-{[(3-cyanophenyl)sulfonyl]amino}ethyl)-1H-pyrrole-3-carboxamide | 654.1 |
| 361 | 1-{3-[(6-amino-5-nitropyridin-2-yl)amino]propyl}-4-(4-chloro-2-methoxyphenyl)-N-{2-[(methylsulfonyl)amino]ethyl}-1H-pyrrole-3-carboxamide | 567.0 |
| 362 | 1-{3-[(6-amino-5-nitropyridin-2-yl)amino]propyl}-4-(4-chloro-2-methoxyphenyl)-N-[(1S)-2-hydroxy-1-methylethyl]-1H-pyrrole-3-carboxamide | 504.0 |

SCHEME 1: SYNTHESIS OF NITRO PYRROLE

Synthesis of 1-[1-{3-[(6-amino-5-nitropyridin-2-yl)amino]propyl}-4-(2,4-dichlorophenyl)-1H-pyrrol-3-yl]-4-methylpiperazin-2-one (Example 59)

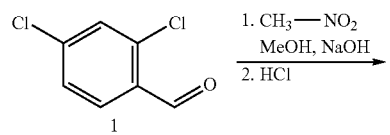

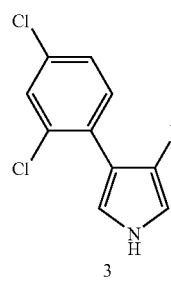

-continued

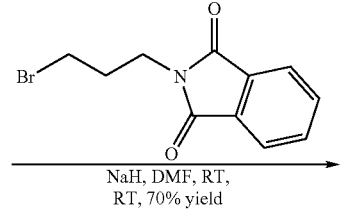

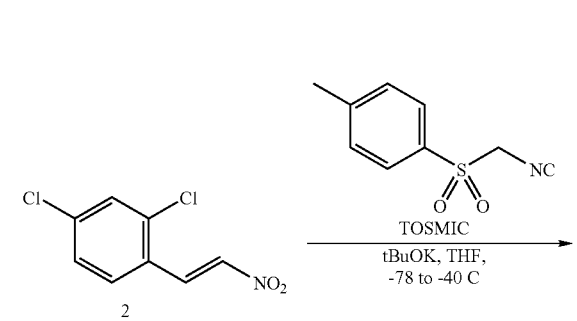

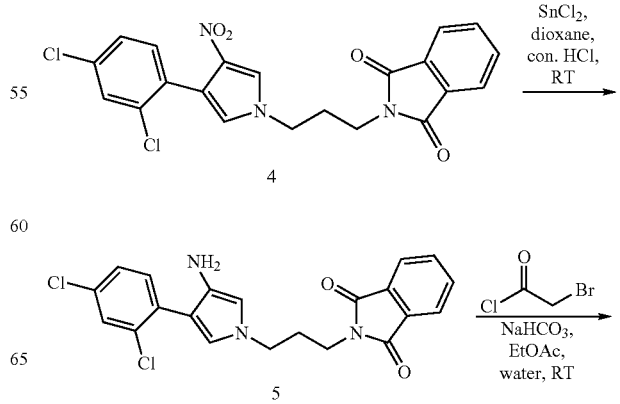

-continued

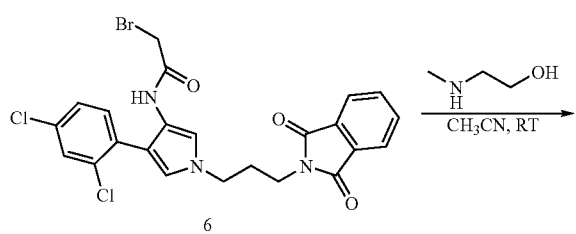

6

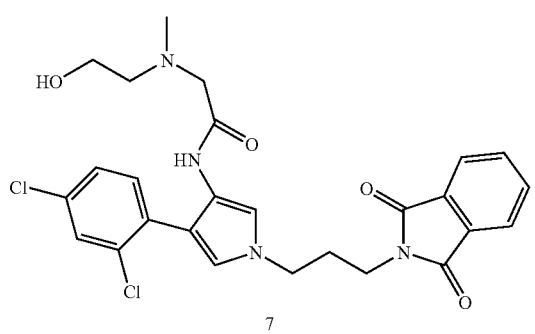

7

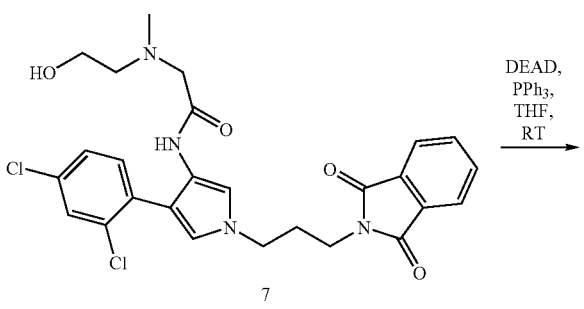

7

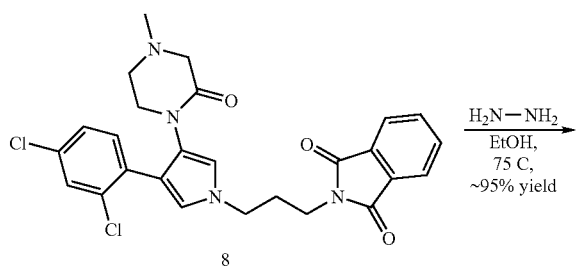

8

-continued

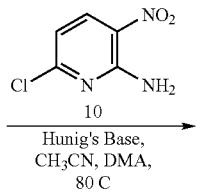

9

10

11

Preparation of 4-ethyl trans-beta-nitrostyrene (2)

An aq. 6M NaOH solution (1.05 eq) was added to a methonolic solution of 4-ethylbenzaldehyde (1 eq) and nitromethane (1 eq) stirred at 0° C. During the slow addition of base, maintain the temperature between 10-15° C. The reaction generates a thick white precipitate. To allow smooth stirring, an additional amount of MeOH was added. After stirring for an additional 15 min., the ice bath was removed. Upon reaching RT, water was added to the reaction, which subsequently turned clear. The clear solution was added to a flask containing a stirred 6M aq. HCl solution. A yellow crystalline precipitate formed. After 10 min., the crystalline product was filtered, washed thoroughly with water, suction dried and recrystallized from abs. EtOH. 4-ethyl trans-beta-nitrostyrene (2) was afforded as a yellow crystalline product in 52% yield and >99% purity (LC/MS m/z 178.2 MH.

Preparation of 4-(2,4-dichlorophenyl)-3-nitropyrrole (3)

A solution of TOSMIC (1 eq) in THF was added dropwise to a stirred solution of potassium tert-butoxide (2.4 eq) at −78° C. under argon. After 10 min., trans-beta-nitrostyrene (2) (1.05 eq) dissolved in THF was added dropwise. After stirring for 15 min. at −78° C., the reaction was allowed to warm to −40° C. The progress of the reaction was followed by TLC (25% EtOAc/Hexane, the UV active product was at $R_f$=0.8). The reaction was then quenched with water, and the product was extracted with ether. The ether layer was subsequently washed with brine and dried over $MgSO_4$, filtered, and concentrated to dryness to give a dark gum. The crude product was dissolved in refluxing EtOAc and left to cool. After 12 hours, the product had completely crystallized out of solution. The pure product was collected by Büchner filtration. A second crop of crystals could be obtained by reducing the volume of the filtrate. After cooling and standing for 6 hours, the second crop of product was collected.

The crystals were washed with minimal ether and dried in vacuo to give (32% yield) of 4-(2,4-dichlorophenyl)-3-nitropyrrole (3) as light orange crystals in >99% purity (LC/MS m/z 258.1 MH+). Product that remained in the supernatant was purified by flash chromatography, eluting with $CH_2Cl_2$.

Preparation of 2-{3-[4-(2,4-dichlorophenyl)-3-nitropyrrolyl]propyl}benzo[c]azoline-1,3-dione (4)

The NaH (1.2 eq) was added to a dry flask under argon. To NaH suspended in DMF, was added a solution of 4-(2,4-dichlorophenyl)-3-nitropyrrole (1 eq) in DMF with stirring at RT. After the evolution of gas bubbles had stopped, the reaction stirred for an additional 15 min at which time a solution of 3-bromopropyl phthalimide (1.1 eq) in DMF was added to the yellow-brown solution. After 2 hours, the clear brown reaction was complete (determination by TLC: $CH_2Cl_2$/acetonitrile (95:5 v/v), the UV active product was at $R_f$=0.5). Upon completion, the reaction was quenched with half sat. aq. $NH_4Cl$ (added slowly to avoid strong gas evolution and exotherm). EtOAc was added, and after shaking the ivory colored precipitate which formed during the quench was collected by filtration. The organic layer was washed with water, brine, dried ($Na_2SO_4$), filtered, and concentrated to give the desired product as an ivory solid. Both portions of product were combined to afford (~94% yield) 95% pure 2-{3-[4-(2,4-dichlorophenyl)-3-nitropyrrolyl]propyl}benzo[c]azoline-1,3-dione (4), which was used without further purification (LC/MS m/z 445.3 MH+).

Preparation of 2-{3-[3-amino4-(2,4-dichlorophenyl) pyrrolyl]propyl}benzo[c]azo-line-1,3-dione (5)

To a round bottom flask containing a stirred solution of 2-{3-[4-(2,4-dichlorophenyl)-3-nitropyrrolyl]propyl}benzo[c]azoline-1,3-dione (4) (1 eq) and con. HCl (7 eq) in dioxane was added solid $SnCl_2.2H_2O$ (10 eq) in portions. The clear yellow reaction was stirred for 12 hours at which time the reaction was found to be complete by LC/MS. The reaction was neutralized to pH 7 by addition of 6M aq. NaOH, followed by extraction with EtOAc. The organic layers were filtered and concentrated to give a solution of 2-{3-[3-amino-4-(2,4-dichlorophenyl)pyrrolyl]propyl}benzo[c]azoline-1,3-dione (5), which was unstable and used directly in the next step (LC/MS m/z 415.3 MH+). Assumed quantitative yields.

Preparation of N-{4-(2,4-dichlorophenyl)-1-[3-(1,3-dioxobenzo[c]azolin-2-yl)propyl]-pyrrol-3-yl}-2-bromoacetamide (6)

Aqueous $NaHCO_3$ (8 eq) was added to the stirred solution of 2-{3-[3-amino-4-(2,4-dichlorophenyl)pyrrolyl] propyl}benzo[c]azoline-1,3-dione (5) (1 eq) in EtOAc at RT. 2-bromoacetyl chloride (1.5 eq) in minimal EtOAc was added slowly to the vigorously stirred reaction solution. The reaction was monitored by LC/MS and determined to be complete within 30 min. The organic layer was separated and washed with water, brine, dried ($Na_2SO_4$), filtered, and concentrated to dryness to give the crude N-{4-(2,4-dichlorophenyl)-1-[3-(1,3-dioxobenzo[c]azolin-2-yl)propyl]pyrrol-3-yl}-2-bromoacetamide (6) as a dark yellow glass in 76% yield (~90% pure, LC/MS m/z 536.2 MH+). The product (6) was stored at −4° C. to avoid decomposition.

Preparation of N-{4-(2,4-dichlorophenyl)-1-[3-(1,3-dioxobenzo[c]azolin-2-yl)propyl]-pyrrol-3-yl}-2-[(2-hydroxyethyl)methylamino]acetamide (7)

N-Methyl ethanolamine (2 eq) was added to a stirred solution of N-{4-(2,4-dichlorophenyl)-1-[3-(1,3-dioxobenzo[c]azolin-2-yl)propyl]pyrrol-3-yl}-2-bromcacetamide (6) (8.65 eq) in $CH_3CN$ at RT. The reaction was monitored by LC/MS and was determined to be complete after 12 hours. The reaction was concentrated and purified by silica column chromatography eluting with MeOH in $CH_2Cl_2$ (5:95, v/v). After collecting the purified fractions and concentrating, N-{4-(2,4-dichlorophenyl)-1-[3-(1,3-dioxobenzo[c]azolin-2-yl)propyl]pyrrol-3-yl}-2-[(2-hydroxyethyl)methylamino]acetamide (7) was obtained as a light yellow glass (21% yield, LC/MS m/z 530.4 MH+) in 95% purity.

Preparation of 2-{3-[4-(2,4-dichlorophenyl)-3-(4-methyl-2-oxopiperazinyl)pyrrolyl]-propyl}benzo[c]azoline-1,3-dione (8)

DEAD (2.5 eq) and $PPh_3$ (2 eq) were added to N-{4-(2, 4-dichlorophenyl)-1-[3-(1,3-dioxobenzo[c]azolin-2-yl)propyl]pyrrol-3-yl}-2-[(2-hydroxyethyl)methylamino]acetamide (7) (1 eq) dissolved in THF at RT. The reaction was heated to 55° C. for 1 hour until completion was determined by LC/MS. The reaction was concentrated and purified by silica column chromatography, eluting with MeOH in $CH_2Cl_2$ (5:95, v/v). After collecting the purified fractions and concentrating, 2-{3-[4-(2,4-dichlorophenyl)-3-(4-methyl-2-oxopiperazinyl)pyrrolyl]propyl}benzo[c]azoline-1,3-dione (8) was attained as a light yellow glass (LC/MS m/z 512.4 MH+) in quantitative yields.

Preparation of 1-(1-{3-[(6-amino-5-nitro(2-pyridyl)) amino]propyl}-4-(2,4-dichloro-phenyl)pyrrol-3-yl)-4-methylpiperazin-2-one (11)

Hydrazine (1.3 eq) was added to a solution of 2-{3-[4-(2,4-dichlorophenyl)-3-(4-methyl-2-oxopiperazinyl)pyrrolyl]propyl}benzo[c]azoline-1,3-dione (8) in abs. EtOH and stirred at 75° C. for 2 hours. The reaction developed a white precipitate, which was filtered. The EtOH was concentrated under reduced pressure. The residue was taken up in $CH_2Cl_2$ and the precipitate was filtered again. The organic solution was evaporated to a foam. Assuming a quantitative yield, the residue was taken up in $CH_3CN$ and DMA (4:1). Hünig's Base (1.3 eq) was added to the mixture followed by 6-chloro-3-nitro-2-pyridylamine (10) (1.2 eq). The reaction was heated to 80° C. for 2 hours until completion was determined by LC/MS. The reaction was subsequently concentrated. The residue was dissolved in EtOAc, washed with water, brine, dried ($Na_2SO_4$), filtered, and concentrated to dryness to give 1-(1-{3-[(6-amino-5-nitro(2-pyridyl)) amino]propyl}-4-(2,4-dichlorophenyl)pyrrol-3-yl)-4-methylpiperazin-2-one (11). The product (11) was purified by silica column chromatography, eluting with MeOH in $CH_2Cl_2$ (5:95, v/v). After collecting the purified fractions and concentrating, light yellow foam (LC/MS m/z 519.4 MH+, 42% yield) was attained in 95% purity.

SCHEME 2: SYNTHESIS OF AMINO PYRROLES
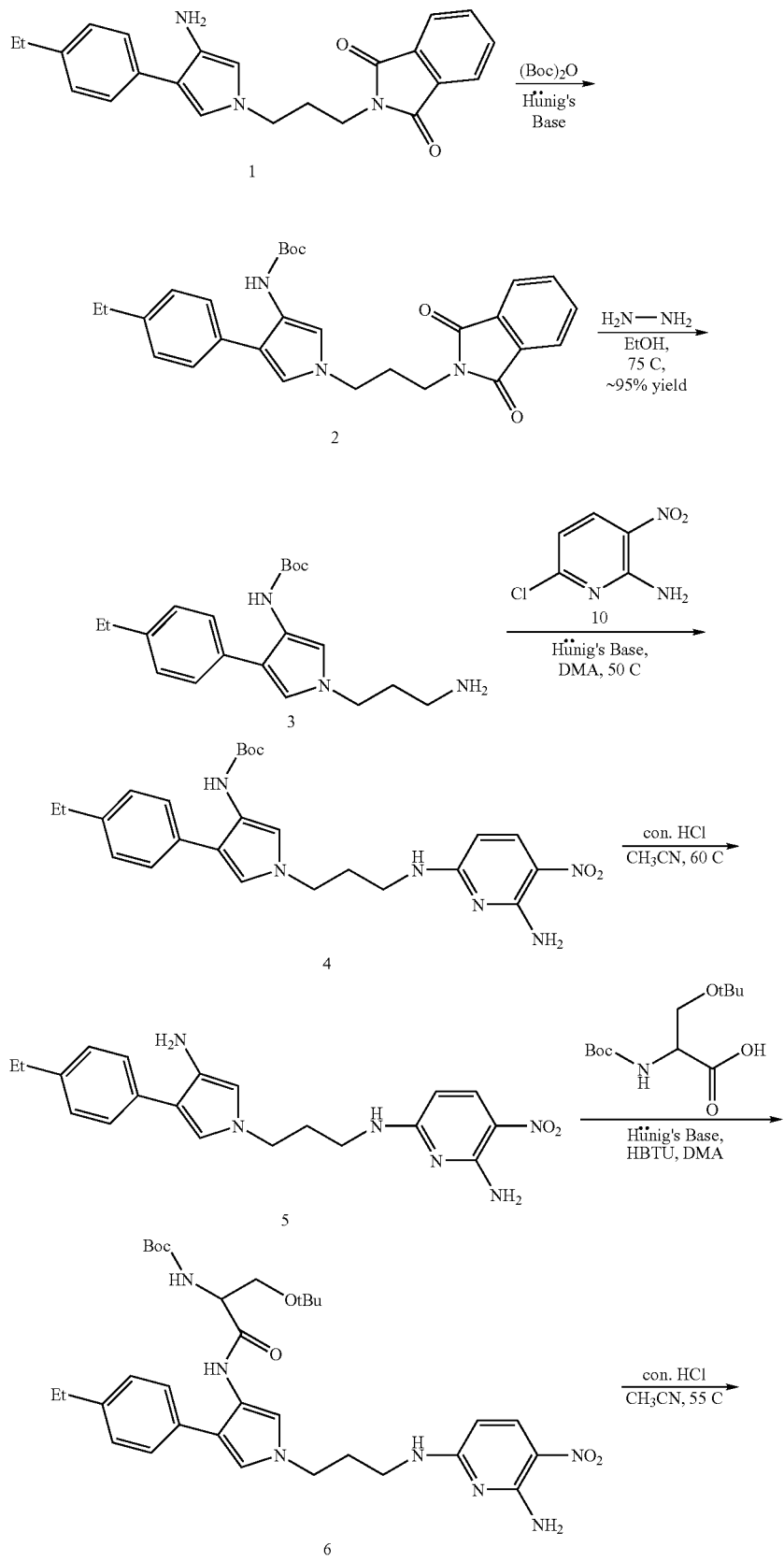

-continued

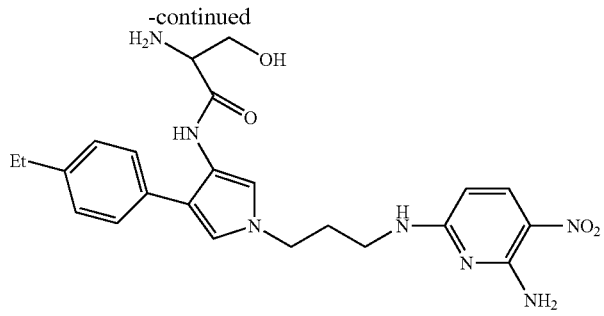

7

Preparation of (tert-butoxy)-N-{1-[3-(1,3-diox-obenzo[c]azolin-2-yl)propyl]4-(4-ethylphenyl)pyrrol-3-yl}carboxamide (2)

2-{3-[3-amino-4-(4-ethylphenyl)pyrrolyl]propyl}benzo[c]azoline-1,3-dione (1 eq) is mixed with (Boc)₂O (1.5 eq) and dioxane to form a clear brown solution. Hünig's base (1.3 eq) is added to the stirred mixture under argon at rt. After 12 hours, an additional equivalent of (Boc)₂O is added to the reaction which converts the last of the starting material to the desired product. The reaction can be monitored by LCMS and TLC eluting with EtOAc/Hexane (3:2, v/v) ($R_f$=0.6). The reaction is diluted with EtOAc and washed with 1N citric acid. The organic layer was separated and washed with 1N citric acid, aq. sat. NaHCO₃, brine, dried (Na₂SO₄), filtered, and concentrated to dryness to give the crude product as a dark brown oil. The product is purified by column chromatography eluting with EtOAc/Hexane (3:7, v/v) affording the product as a yellow powder in 63% yield (95% pure).

Preparation of N-[1-(3-aminopropyl)4-(4-ethylphenyl)pyrrol-3-yl](tert-butoxy)-carboxamide (3)

Hydrazine (5 eq) was added to a solution of (tert-butoxy)-N-{1-[3-(1,3-dioxobenzo[c]azolin-2-yl)propyl]-4-(4-ethylphenyl)pyrrol-3-yl}carboxamide (1 eq) in abs. EtOH at 50° C. for 2 hours. The reaction developed a white precipitate which was filtered off. The EtOH was concentrated under reduced pressure. The residue was taken up in CH₂Cl₂ and the precipitate was filtered again. The organic solution was evaporated to a yellow solid containing product and solvent. Assumed a quantitative yield.

Preparation of N-(1-{3-[(6-amino-5-nitro(2-pyridyl))amino]propyl}-4-(4-ethyl-phenyl)pyrrol-3-yl)(tert-butoxy)carboxamide (4)

N-[1-(3-aminopropyl)-4-(4-ethylphenyl)pyrrol-3-yl](tert-butoxy)carboxamide (1 eq) and 6-chloro-3-nitro-2-pyridylamine (1.2 eq) were dissolved in DMA with stirring under argon at rt. Hünig's Base (1.5 eq) was added to the clear dark brown solution which was heated to 60° C. for 12 hours until completion was determined by LC/MS and TLC, eluting with EtOAc/Hexane (3:2, v/v) ($R_f$=0.3). EtOAc was added to the reaction mixture which was then washed with water, brine, dried (Na₂SO₄), filtered, and concentrated to dryness to give the crude brown product. The brown residue was purified by silica column chromatography eluting with EtOAc/Hexane (24:26, v/v). After collecting the purified fractions and concentrating, the product was isolated as a light yellow solid (75% yield).

Preparation of {3-[3-amin-4-(4-ethylphenyl)pyrrolyl]propyl}(6-amino-5-nitro(2-pyridyl))amine (5)

N-(1-{3-[(6-amino-5-nitro(2-pyridyl))amino]propyl}-4-(4-ethylphenyl)pyrrol-3-yl)(tert-butoxy)carboxamide (1 eq) was dissolved in CH₃CN and 1N aq. HCl (45% v/v). The clear brown solution was heated to 60° C. for 12 hours until complete by LC/MS. The reaction was cooled to room temperature and diluted with a solution of CH₃CN and water. The mixture was frozen and lyophilized to dryness giving a pure dark yellow powder, in quantitative yields as the double HCl salt. {3-[3-amino-4-(4-ethylphenyl)pyrrolyl]propyl}(6-amino-5-nitro(2-pyridyl))amine was used without further purification.

Preparation of N-(1-{3-[(6-amino-5-nitro(2-pyridyl))amino]propyl}-4-(4-ethyl-phenyl)pyrrol-3-yl)-3-(tert-butoxy)-2-[(tert-butoxy)carbonylamino]propanamide (6)

Hünig's Base (1.5 eq) was added to a solution of Boc-serine (1.5 eq) and HBTU in DMA. The mixture was shaken for 30 min at rt. {3-[3-amino-4-(4-ethylphenyl)pyrrolyl]propyl}(6-amino-5-nitro(2-pyridyl))amine.2HCl (1 eq) was added to the activated amino acid. After shaking for 16 h, the entire reaction solution was injected onto a preparative HPLC column (C18 reverse phase system) eluting with a gradient of CH₃CN/water with 0.1% TFA. After collecting the purified product fractions and lyophilizing, a yellow powder was obtained as the mono-TFA salt.

Preparation of 2-amino-N-(1-{3-[(6-amino-5-nitro(2-pyridyl))amino]propyl}4-(4-ethylphenyl)pyrrol-3-yl)-3-hydroxypropanamide (7)

N-(1-{3-[(6-amino-5-nitro(2-pyridyl))amino]propyl}-4-(4-ethylphenyl)pyrrol-3-yl)-3-(tert-butoxy)-2-[(tert-butoxy)carbonylamino]propanamide (1 eq) was dissolved in a mixture of aq. 1N HCl (75% v/v) and CH₃CN to form a clear yellow solution which was heated at 55° C. for 12 hours. LC/MS showed that the reaction was greater than 90% pure product. The reaction was diluted with a CH₃CN/water solution (1:1 v/v) and lyophilized to dryness giving a yellow powder as the HCl salt hydrate.

Preparation f N-(1-{3-[(6-amino-5-nitro(2-pyridyl))amino]propyl}-4-(4-ethyl-phenyl)pyrrol-3-yl)-2-bromoacetamide A solution of 2-bromoacetyl chloride (2 eq) in THF was added to a suspension of {3-[3-amino-4-(4-ethylphenyl)

pyrrolyl]propyl}(6-amino-5-nitro(2-pyridyl))amine (1 eq) in THF at RT followed by addition of 2,6-lutidine (4 eq). The clear yellow solution is stirred for 30 min and was judged complete by LC/MS. The reaction was diluted with $CH_2Cl_2$, and the organic layer was washed with 1N aq. citric acid, water, sat. aq. $NaHCO_3$, brine, dried ($Na_2SO_4$), filtered, and concentrated to dryness to give the crude product as a yellow glass in 76% yield (>90% pure). This product was stored in a freezer as the glass and used quickly without further purification.

Preparation of N-(1-{3-[(6-amino-5-nitro(2-pyridyl))amino]propyl}-4-(4-ethyl-phenyl)pyrrol-3-yl)-2-[(3-methoxypropyl)amino]acetamide N-Methyl ethanolamine (10 eq) was added to a solution of N-(1-{3-[(6-amino-5-nitro(2-pyridyl))amino]propyl}-4-(4-ethylphenyl)pyrrol-3-yl)-2-bromoacetamide (1 eq) in DMA at RT. The reaction was shaken for 16 h and checked by LC/MS. The reaction did not reach completion (>80% product) and was heated to 55° C. for 16 h. Once complete, the entire reaction solution was injected onto a preparative HPLC column (C18 reverse phase system) eluting with a gradient of $CH_3CN$/water with 0.1% TFA. After collecting the purified product fractions and lyophilizing, a yellow powder was obtained as the mono-TFA salt (40% yield).

Preparation of N-(1-{3-[(6-amino-5-nitro(2-pyridyl))amino]propyl}-4-(4-ethyl-phenyl)pyrrol-3-yl) acetamide A solution of {3-[3-amino-4-(4-ethylphenyl)pyrrolyl]propyl}(6-amino-5-nitro-(2-pyridyl))amine (5) (1 eq), acetic anhydride (2 eq) and Hünig's base (4 eq) in THF was stirred at RT for 45 min. The reaction was followed by LC/MS. The yellow solution was concentrated to a glass and then dissolved in DMSO. Once complete, the entire reaction solution was injected onto a preparative HPLC column (C18 reverse phase system) eluting with a gradient of $CH_3CN$/water with 0.1% TFA. After collecting the purified product fractions and lyophilizing, a yellow powder was obtained as the mono-TFA salt.

SCHEME 3: SYNTHESIS OF 2,4-AMIDE PYRROLES

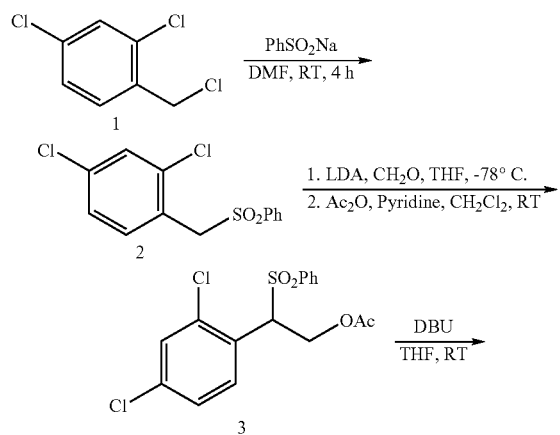

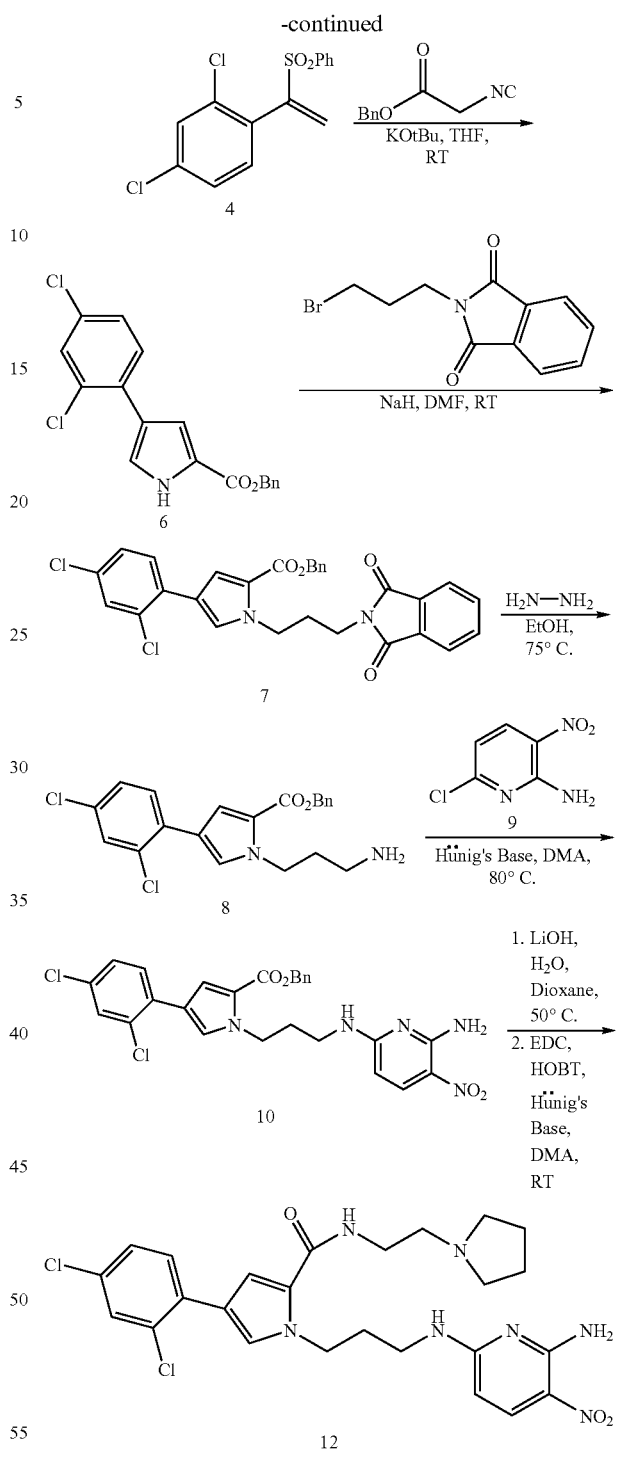

Preparation of {[(2,4-dichlorophenyl)methyl]sulfonyl}benzene (2)

Sodium benzenesulfonate (2 eq) was added to a stirred solution of 2,4-dichlorobenzyl chloride (1) (1 eq) in DMF under argon at rt. After 4 h, the reaction was poured into a stirred beaker of water. The aqueous phase was extracted with ether, dried ($MgSO_4$), filtered, and concentrated to a

Preparation of 2-(2,4-dichlorophenyl)-2-(phenylsulfonyl)ethyl acetate (3)

The crude sulfone (2) (1 eq) in THF was added dropwise via addition funnel to a freshly prepared solution of diisopropylamine (1.3 eq), n-BuLi 2.5 M in hexanes (1.1 eq) and THF under $N_2$ at −78° C. with stirring. After 30 min., the paraformaldehyde was added (2.1 eq). The reaction was stirred for an additional 30 min. at which time the reaction was allowed to warm to room temperature over 4.5 h. The reaction was then quenched with sat. aq. $NH_4Cl$. The aqueous layer was extracted with EtOAc, dried ($Na_2SO_4$), filtered and concentrated under reduced pressure to yield the crude sulfonyl hydrin which was used without further purification. The crude sulfonyl hydrin was dissolved in $CH_2Cl_2$ (excess) and pyridine (1.2 eq) followed by the addition of $Ac_2O$ (1.1 eq). After stirring at room temperature for 14.5 h, the reaction was quenched with sat. aq. $NH_4Cl$. The layers were separated, and the aqueous layer was extracted with $Et_2O$. The combined organic layers were dried ($Na_2SO_4$), filtered, and concentrated to give the 2-(2,4-dichlorophenyl)-2-(phenylsulfonyl)ethyl acetate (3) (94% yield) in high purity.

Preparation of {[1-(2,4-dichlorophenyl)vinyl]sulfonyl}benzene (4)

DBU (1.5 eq) in THF was added to a solution of 2-(2,4-dichlorophenyl)-2-(phenylsulfonyl)ethyl acetate (3) (1 eq) in THF at rt. After stirring for 40 min., the reaction was quenched with sat. aq. $NH_4Cl$. The layers were separated, and the aqueous layer was extracted with EtOAc. The combined organic layers were washed with brine, dried ($Na_2SO_4$), filtered, and concentrated under reduced pressure to give the {[1-(2,4-dichlorophenyl)vinyl]sulfonyl}benzene (4) (97% yield).

Preparation of phenylmethyl 4-(2,4-dichlorophenyl)pyrrole-2-carboxylate (6)

A solution of {[1-(2,4-dichlorophenyl)vinyl]sulfonyl}benzene (4) (1 eq) and benzyl 2-isocyanoacetate (5) (prepared by the method of—Lash, T. D.; Bellettini, J. R.; Bastian, J. A.; Couch, K. B. *Synthesis* 1994, 170-172. (2 eq)) in THF were added to a suspension of potassium tert-butoxide (2 eq) was suspended in THF under $N_2$ with stirring at rt. After 14 h, the reaction was quenched with sat. aq. $NH_4Cl$. The layers were separated, and the aqueous layer was extracted with EtOAc. The combined organic layers were dried ($Na_2SO_4$), filtered, and concentrated. The residue was recrystallized twice from minimal hot solvent (THF/hexanes, 1:1 v/v) to give 4-(2,4-dichlorophenyl)pyrrole-2-carboxylate (6) as a pure, yellow crystalline-solid (34% yield).

Synthesis of phenylmethyl 1-{3-[(6-amino-5-nitro(2-pyridyl))amino]propyl}-4-(2,4-dichlorophenyl)pyrrole-2-carboxylate (10) was performed as previously described for the 3,4-ester of the nitro pyrrole (Scheme 2).

Preparation of 1-{3-[(6-amino-5-nitro(2-pyridyl))amino]propyl}-4-(2,4-dichlorophenyl)pyrrole-2-carboxylic acid (11)

Solid lithium hydroxide (20 eq) was added to a stirred solution of 1-{3-[(6-amino-5-nitro(2-pyridyl))amino]propyl}-4-(2,4-dichlorophenyl)pyrrole-2-carboxylate (10) (1 eq) in THF and water at rt. The mixture was heated to 50° C. for 12 h until complete by LC/MS. The reaction was allowed to cool to room temperature and acidified with 1 M HCl (aq.). The acidic solution was extracted with EtOAc. The combined organic layers were dried ($Na_2SO_4$), filtered, and concentrated to pure 1-{3-[(6-amino-5-nitro(2-pyridyl))amino]propyl}-4-(2,4-dichlorophenyl)pyrrole-2-carboxylic acid (11) as a sticky yellow solid (99% yield).

Preparation of (1-{3-[(6-amino-5-nitro(2-pyridyl))amino]propyl}-4-(2,4-dichloro-phenyl)pyrrol-2-yl)-N-(2-pyrrolidinylethyl)carboxamide (12)

Hünig's Base (2.5 eq), HOBT (1.2 eq), EDC (1.2 eq) and 1-(2-aminoethyl)pyrrolidine (1.5 eq) were added sequentially to a solution of 1-{3-[(6-amino-5-nitro(2-pyridyl))amino]propyl}-4-(2,4-dichlorophenyl)pyrrole-2-carboxylic acid (11) (1 eq) in DMF (2M) at room temperature with stirring. After 12 hours, the DMF was removed under high vacuum via a centrifugal evaporator. The residue is dissolved in EtOAc and washed with sat. aq. $NaHCO_3$, dried ($Na_2SO_4$), filtered, and concentrated. The crude product was purified using a plug of silica eluting with 4% MeOH in $CH_2Cl_2$ to give (1-{3-[(6-amino-5-nitro(2-pyridyl))amino]propyl}-4-(2,4-dichlorophenyl)pyrrol-2-yl)-N-(2-pyrrolidinylethyl)carboxamide (12) as a yellow solid (13% yield, 96% pure).

SCHEME 4: SYNTHESIS OF 2,3-AMIDE PYRROLES

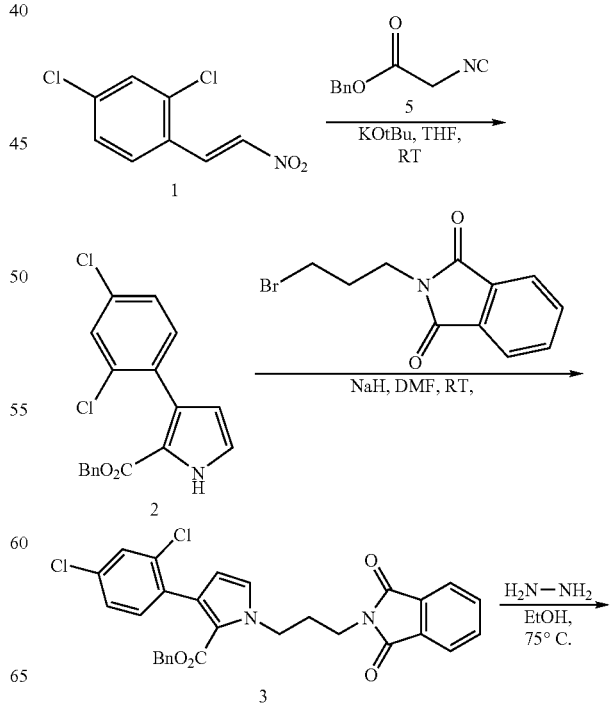

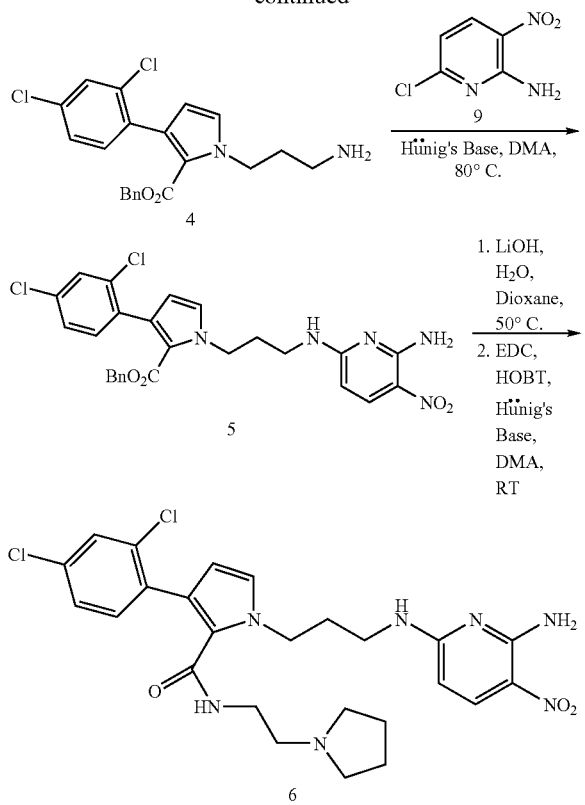

Preparation of phenylmethyl
3-(2,4-dichlorophenyl)pyrrole-2-carboxylate (2)

DBU (1 eq) was added to a stirred solution of 2,4-Dichloronitrostyrene (1) (1 eq) and benzyl 2-isocyanoacetate (0.9 eq) in THF at −78° C. under $N_2$. The reaction was allowed to warm to room temperature over 2 h. The reaction could be followed by TLC eluting with $CHCl_3$ ($R_f$=0.3). After stirring for an additional 12 h, the reaction was diluted with $CH_2Cl_2$ and EtOAc. The organic mixture was washed with 0.1 N HCl, water, sat. aq. $NaHCO_3$, brine, dried ($Na_2SO_4$), filtered and concentrated under reduced pressure to an oil. The crude product was purified using silica column chromatography eluting with $CHCl_3$ to obtain pure phenylmethyl 3-(2,4-dichlorophenyl)pyrrole-2-carboxylate (2) (15% yield).

The steps for preparation of 1-{3-[(6-amino-5-nitro(2-pyridyl))amino]propyl}-3-(2,4-dichlorophenyl)pyrrole-2-carboxylate (5) and the transformation of pyrrole phenylmethyl to benzyl ester 10 use the same procedures as previously described for the 3,4-ester and nitro pyrrole series.

Example 363

Screening for GSK3 Inhibitory Activity Using a Cell-Based Glycogen Synthase Assay CHO-HIRC cells are maintained in 10 cm tissue culture plates in Ham's F12 medium/10% dialyzed fetal bovine serum. Cells from a confluent 10 cm plate are harvested and divided into the 6 wells of a 6-well tissue culture plate to a final volume of 2 ml of medium. The cells are left to grow at 37° C. for 24 hours. The cells are then washed three times in Ham's F12 medium containing no fetal bovine serum, and finally the cells are left for a further 24 hours at 37° C. in 2 ml of the serum-free medium.

At the end of this time, 20 μl of compound dissolved in DMSO is added to each well and incubated at 37° C. After 20 minutes the medium is removed and the cells are washed once in PBS at room temperature and then rapidly frozen in the plates in liquid nitrogen. Cells are then thawed on ice in the presence of 140 μl of lysis buffer (50 mM Tris pH 7.8; 1 mM EDTA, 100 mM NaF, 25 μg/ml leupeptin, 1 mM DTT, 1 mM PMSF) per well. Cells are scraped from the plates and frozen in Eppendorf tubes on dry ice. Lysates are then thawed and refrozen on dry ice.

After rethawing, lysates are spun at 14,000 g for 15 minutes. The supernatants are then removed and stored on ice. Each supernatant (45 μl) is added to 45 μl of reaction buffer (65 mM Tris pH 7.8; 26 mM EDTA, 32.5 mM KF, 9.3 mM UDP-glucose; 11 mg/ml glycogen; 500 nCi/ml $^{14}$C-UDP-glucose) and a further 45 μl is added to 45 μl reaction buffer/20 mM glucose-6-phosphate. Reactions are incubated at 30° C. for 30 minutes and then spotted onto a 2 cm square 31ET chromatograph paper (Whatman). Filter papers are washed twice for 20 minutes in 66% ethanol, rinsed briefly in acetone and dried for 1 hour at room temperature.

Filters are added to 5 ml of liquid scintillant and counted in a liquid scintillation counter. The percentage of the total glycogen synthase that is active in any lysate is expressed as 100× (cpm minus glucose-6-phosphate)/(cpm plus glucose-6-phosphate). Such values are determined in duplicate for 5 different concentrations of compound and for DMSO alone, and the values are then plotted against the logarithm of the concentration. The concentration of compound which stimulates glycogen synthase activity to 50% of the maximal level is determined by fitting a sigmoidal curve to the plotted data. The maximal level is defined as that level to which glycogen synthase activity tends asymtotically as the concentration of test compound increases substantially beyond the $EC_{50}$. Representative compounds of the invention were shown to have activity of concentrations less that 10 μM.

Example 364

Screening for Inhibition of Tau Protein Phosphorylation

A. Transient Transfection of COS Cells with GSK3 Expression Plasmid and Tau Expression Plasmid Construction COS cells are maintained in T25 tissue culture flasks in high glucose MEM medium/5% fetal bovine serum. Cells from a confluent T25 flask are harvested and 80,000 cells/well are seeded into Corning 6-well tissue culture plates in a final volume of 2 ml/well of medium. The cells are left to grow at 37° C. for 48 hours. The cells are then washed twice in Opti-MEM containing no fetal bovine serum, and finally the cells are left in 1 ml of Opti-MEM.

Polynucleotide encoding tau protein is subcloned into plasmid pSG5 under an early SV40 promoter to generate a tau expression plasmid. The cloning of cDNA encoding tau protein is generally described in Goedert et al., *EMBO Journal*, 8(2):393-399 (1989), which is incorporated herein by reference. A GSK3 expression plasmid is prepared by subcloning polynucleotide encoding GSK3β into pCG, which is an ApEVRF derivative described in Giese et al.,

*Genes & Development,* 9:995-1008 (1995) and Matthias et al., *Nucleic Acid Research,* 17:6418 (1989), both of which are incorporated herein by reference.

The following solutions are prepared in 1.5 ml Eppendorf tubes: Solution A: for each transfection, 2 µg of DNA (tau expression plasmid) and 0.7 µg of DNA (GSK3 expression plasmid) are diluted into 100 µl of Opti-MEM (Gibco BRL); Solution B: for each transfection, 8 µl of Lipofectamine reagent is diluted into 100 µl of Opti-MEM. The two solutions are combined, mixed gently, and incubated at room temperature for 45 minutes to allow DNA-liposome complexes to form. For each transfection, 0.8 ml of Opti-MEM is added to the tube containing the complexes. The diluted solution is mixed gently and overlaid onto the rinsed cells. The cells are incubated with the complexed DNA/Lipofectamine for 6 hours at 37° C. in a $CO_2$ incubator. Following incubation, 1 ml of growth medium (high glucose MEM) with 20% FBS is added to each well and incubated at 37° C. overnight. The medium is replaced with fresh, complete medium at 18 hours following the start of transfection, and the cells are left to grow at 37° C. for another 48 hours.

B. Tau Phosphorylation Inhibition Assay

Two hours before harvesting, 2 µl of test compound (GSK3 inhibitor) dissolved in DMSO is added to each well and incubated at 37° C. After 2 hours the medium is removed and the cells are rapidly frozen on the plates on dry ice and stored at −70° C. Cells are thawed on ice in the presence of 200 µl of lysing buffer (1% Triton® X-100, 20 mM Tris pH 7.5, 137 mM NaCl, 15% glycerol, 25 µg/ml leupeptin, 1 µg ml pepstatin-A, 1 µM PMSF, 21 µg/ml aprotinin, 50 mM NaF, 50 mM β-glycerophosphate, 15 mM sodium pyrophosphate, 1 mM sodium orthovanadate). The contents of each well are centrifuged at 14,000 g, 4° C. for 5 minutes and the supernatants transferred to clean tubes. At this point the lysates may be stored at −20° C.

C. ELISA to Detect Phosphorylated Tau in Cell Lysates

Immulon 4 strips (Dynatech) are coated with monoclonal anti-phosphorylated tau (AT8, Polymedco, Inc.) at 5 µg/ml in PBS containing $Ca^{++}$ and $Mg^{++}$, 100 µl/well. After overnight incubation at 4° C., the strips are washed twice with washing buffer (PBS containing 0.05% Tween® 20) and blocked with PBS containing 1% BSA, 5% normal mouse serum and 0.05% Tween® 20 at room temperature for 1 hour. The strips are washed 5 times with washing buffer. Lysate (100 µl) diluted 1:10 in PBS containing 1% BSA, 0.1% $NaN_3$ is added into each well and incubated at room temperature for 1 hour. After washing, 100 µl of 0.5 µg/ml biofinylated monoclonal anti-(non-phosphorylated) tau (HT7, Polymedco, Inc.) in PBS-BSA is added into each well. Strips are washed 5 times and HRP-conjugated streptavidin is added, incubated at room temperature for 30 minutes and washed extensively with washing buffer. TMB substrate (Pierce) is used for color development and the reaction is stopped by adding an equal volume of 0.8 M sulfuric acid. Strips are read on an ELISA plate reader using a 450 nm filter. The concentration of compound that inhibits tau phosphorylation to 50% of the maximal level (i.e., $IC_{50}$) is determined by fitting a sigmoidal curve to the plotted data.

Example 365

Testing the Potential of GSK3 Inhibitors to Protect Primary Hippocampal Cells from Glutamate Excitotoxicity Hippocampai were dissected from embryonic day 18-19 rats. The tissue was collected in Hibernate TM media (Gibco BRL) and minced into approximately 1 mm pieces. Tissue was dissociated using the Papain Dissociation System (Worthington Biochemical Corporation). Following-isolation the cells were resuspended in serum-free media composed of Neurobasal TM (Gibco BRL), 2% B27 supplement (Gibco-BRL), L-glutamine and antibiotics. Cells were plated in 35 mm tissue culture dishes coated with poly-L-lysine at a concentration of $7.5 \times 10^4$ cells per dish. Following 10-14 days at 37° C. in 5% CO2 cells were rinsed and fed with fresh media. The next day representative compounds of the invention were added to the culture media to a final concentration of between 1 nM and 100 µM. Four to eight hours following compound addition the conditioned media was removed from cells and stored at 37° C. Cultures were rinsed twice with HEPES-buffered balanced salt solution (HBSS) containing 10 µM glycine. Grabb and Choi, *J. Neuroscience* 19:1657-62 (1999). Cultures were then exposed for 5 min at room temperature to 200 µM glutamic acid in the same HBSS. Following exposure, cultures were rinsed three times with the buffer and then returned to their original conditioned media containing the compounds. Twenty to twenty-four hours following glutamic acid exposure, cultures were rinsed in HBSS and exposed for 10 min to Trypan Blue. This dye is taken up by dead cells. The cultures were rinsed and then fixed for 30 min in 4% paraformaldehyde. The number of live and dead (blue nuclei) large neurons are counted (at least 200 cells from each culture) by phase contrast microscopy and photographed. Using this method, compounds of this invention have been shown to be capable of significantly reducing the potential of glutamate to induce neuronal cell death.

Example 366

Evaluation of Efficacy in Diabetic Rodents The Glucose Tolerance Test

Compound Formation for Oral Dosing:

Test compounds were typically formulated for oral gavage as solutions in water or suspensions in 1% carboxymethylcellulose/0.1% tween-80 (both from Sigma Chem., MO) the day prior to administration. Some early compounds were formulated as solutions in 15% Captisol (a modified cyclodexytrin by CyDex Co., IL) following procedures common to those below. For water solutions, dry and lyophilized test compound powder is solubilized in distilled water and mixed well by vortexing and sonicating. If necessary, test solution is pH adjusted with 1 N NaOH or 1 N HCl and is finally sterile filtered through a syringe appended with a 0.2 micron cellulose acetate membrane (Millipore Co., MA). For oral suspensions, the test compound powder is mixed with a fresh suspension of 1% carboxymethylcellulose/0.1% tween-80 and extensively sonicated, pH adjusted if necessary as described above, and vortexed until particle size is homogeneous and <10 micron in size.

Diabetic Mouse Glucose Tolerance Test:

Obese db/db (female C57B1Ks/J) mice were obtained from Jackson Labs (Bar Harbor, Me.) at 8 weeks of age and used for efficacy testing 1-2 weeks later. On the morning of a test, food was removed early in the morning (7-8 hrs prior to the glucose bolus). Local anesthetic (EMLA crème, Astra Pharm., MA) was applied to the end of the tail and 50-100 ul blood samples were obtained from snips of the tail tip and collected into eppendorf tubes containing 5 ul 500 U/ml sodium heparin (Elkins-Sinn, NJ) with subsequent isolation of plasma. Samples were obtained at various intervals throughout the day for a total of 6-8 time points. Mice were randomized into treatment groups and administered the first oral dose of test compound (0.2 ml volume) 4.5 hr prior to the glucose and again 0.5 hr prior to administration of 0.2 ml 50% dextrose (Abbott Lab., IL) via oral gavage (oGTT) or intraperitoneal injection. After the final blood sample about 2 hr following the glucose administration, food was returned to the animals.

Regulation of Basal Glycemia and Insulinemia:

Test compounds were typically orally administered to db/db mice (see above) or ZDF rats (Genetic Models, Inc.; Indianapolis, Ind.) in the context of a multi-day, multi-dose regimen or as a single bolus. The ZDF rats were received at 8 weeks of age and used for efficacy testing 1-2 weeks later. Food was removed about 30 min prior to dosing and a single bolus of test compound (dosing volume ranging from 1-8 mg/ml) was administered. Blood was sampled as described above at 1-6 time points over the next 2-3 hr. Food was returned to the animal cages following the blood sampling.

Primary Endpoints:

Glucose and insulin levels are measured from plasma and/or blood samples. Glucose levels are measured from whole blood by the One-Touch glucometer (Lifescan Co., CA) and from plasma by Beckman glucose analyzer. Glucose results typically reflect blood values for mouse and plasma values for rat studies. Measurement of insulin levels has been via ELISA (Crystal Chem. Co., IL) following the supplier's protocol.

Results Quantitation:

Efficacy may be expressed as mg/dL glucose or ng/ml insulin or represented as area under the curve (AUC) for plasma glucose (taken above the normoglycemic baseline of 100 mg/dL) and insulin (taken above the normoinsulinemic baseline of 1 ng/mL). Typically, when expressed as AUC, the results are actually represented as reduced AUC ([(vehicle control AUC—test group AUC)/vehicle control AUCX100]). Such expression provides a single quantitative expression of the magnitude of improved glucose disposal and/or reduced basal hyperglycemia or insulin conservation relative to the placebo control group.

Results:

Representative compounds of the invention exhibited good in vitro potency, and when formulated in captisol and administered s.c. to mice (30 mg/kg), exhibited high bioavailability and tissue penetrance in vivo. A significant reduction in basal hyperglycemia just prior to the glucose tolerance test, and significantly improved glucose disposal following glucose challenge were observed. A 45-50% reduction in the AUC relative to the control group was observed if the glucose response is quantitated by determining the area under the blood glucose curve (AUC) from −60 min to +120 min. This is comparable to the efficacy obtained with Troglitazone (when dosed orally for at least several days at either 60 or 100 mg/kg/day). Also of significance was the observation that insulin levels in treated animals remained lower than in control mice.

While the preferred embodiment of the invention has been illustrated and described, it will be appreciated that various changes can be made therein without departing from the spirit and scope of the invention.

What is claimed is:

1. A compound having the structure:

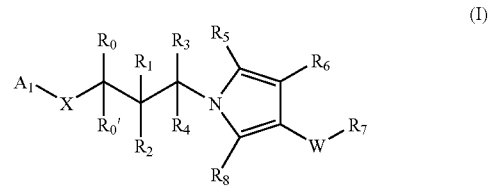

(I)

wherein:

X is nitrogen, oxygen, or optionally substituted carbon;

W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, —CHF—, —CONH—, —CONR'—, and —NR'—, where R' is alkyl, substituted alkyl, cycloalkyl, aryl, heteroaryl, heterocyclo;

A$_1$ is an optionally substituted six-membered heterocyclic group having N as the only ring heteroatom;

R$_0$ and R$_0$' are independently selected from the group consisting of hydrogen and methyl;

R$_1$, R$_2$, R$_3$, and R$_4$ are independently selected from the group consisting of hydrogen, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, and aryl;

R$_5$ and R$_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkylcarbonylamino, cycloimido, amidino, cycloamidino, guanidinyl, aryl, biaryl, and arylsulfonamido;

R$_6$ is selected from the group consisting of hydrogen and optionally substituted aryl;

R$_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, alkylcarbonyloxy, arylcarbonyloxy, aralkylcarbonyloxy, alkylaminocarbonyloxy, arylamino-carbonyloxy, formyl, loweralkylcarbonyl, loweralkoxycarbonyl, aminocarbonyl, aminoaryl, alkylsulfonyl, sulfonamido, aminoalkoxy, alkylamino, alkylcarbonylamino, alkylaminocarbonylamino, arylaminocarbonylamino, aralkylcarbonylamino, arylcarbonylamino, cycloamido, cyclothioamido, cycloamidino, cycloalkyl, cycloimido, guanidinyl, aryl, arylsulfonyl and arylsulfonamido;

the tautomers thereof;

or a pharmaceutically acceptable salt thereof.

2. A compound of claim 1 wherein X is nitrogen.

3. A compound of claim 1 wherein R$_1$, R$_2$, and R$_3$ are hydrogen and R$_4$ is selected from the group consisting of hydrogen, methyl, ethyl, aminoethyl and dimethylaminoethyl.

4. A compound of claim 1 wherein R$_1$, R$_2$, R$_3$, and R$_4$ are hydrogen.

5. A compound of claim 1 wherein $A_1$ has the formula:

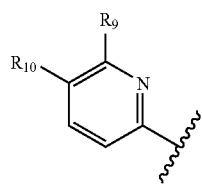

(IV)

wherein $R_9$ and $R_{10}$ are independently selected from the group consisting of hydrogen, hydroxy, nitro, amino, cyano, halo, thioamido, arnidino, oxamidino, alkoxyarnidino, imidino, guanidinyl, sulfonamido, carboxyl, formyl, loweralkyl, aminoloweralkyl, loweralkylamino loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl.

6. A compound of claim 1 wherein at least one of $R_5$ and $R_8$ is a substituted or unsubstituted moiety of the formula:

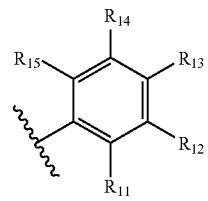

(V)

wherein $R_{11}$, $R_{12}$, $R_{13}$, $R_{14}$, and $R_{15}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkylcarbonylamino, heteroaralkylcarbonylamino, arylcarbonylamino, heteroarylcarbonyl-amino, aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyl-oxyalkyl, and heteroaralkearbonyloxyalkyl.

7. A compound of claim 6 wherein $R_{11}$, $R_{12}$, $R_{14}$ and $R_{15}$ are hydrogen and $R_{13}$ is selected from the group consisting of halo, loweralkyl, hydroxy, loweralkoxy, haloloweralkyl, aminocarbonyl, alkylaminocarbonyl and cyano.

8. A compound of claim 6 wherein $R_{11}$, $R_{13}$, and $R_{15}$ are hydrogen and $R_{12}$ and $R_{14}$ are independently selected from the group consisting of halo, loweralkyl, hydroxy, loweralkoxy, haloloweralkyl and cyano.

9. A compound of claim 6 wherein $R_{11}$, $R_{12}$, $R_{14}$, and $R_{15}$ are hydrogen and $R_{13}$ is heteroaryl.

10. A compound of claim 6 wherein $R_{11}$, $R_{12}$, $R_{14}$, and $R_{15}$ are hydrogen and $R_{13}$ is a heterocycloalkyl.

11. A compound of claim 6 wherein at least one of $R_{11}$, $R_{12}$, $R_{13}$, $R_{14}$, and $R_{15}$ are halo and the remainder of $R_{11}$, $R_{12}$, $R_{13}$, $R_{14}$, and $R_{15}$ are hydrogen.

12. A compound of claim 1 wherein at least one of $R_5$ and $R_8$ is selected from the group consisting of dichlorophenyl, difluorophenyl, trifluoromethylphenyl, chlorofluorophenyl, bromochlorophenyl, ethylphenyl, methylchlorophenyl, cyanophenyl, and cyanochlorophenyl.

13. A compound of claim 1 wherein $R_6$ is substituted or unsubstituted aryl.

14. A compound in claim 1 wherein $R_5$ and $R_8$ are independently hydrogen or lower alkyl.

15. A compound having the structure:

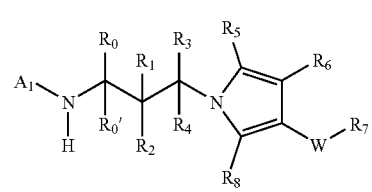

(II)

wherein:
W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, —CHF, —CONH—, —CONR'—, and —NR'—, where R' is alkyl, substituted alkyl, cycloalkyl, aryl, heteroaryl, heterocyclo;

$A_1$ is an optionally substituted six-membered heterocyclic group having N as the only ring heteroatom;

$R_0$ and $R_0'$ are independently selected from the group consisting of hydrogen and methyl;

$R_1$, $R_2$, $R_3$, and $R_4$ are independently selected from the group consisting of hydrogen, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, and aryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkylcarbonylamino, cycloimido, amidino, cycloarnidino, guanidinyl, aryl, biaryl, and arylsulfonamido;

$R_6$ is selected from the group consisting of hydrogen, and optionally substituted aryl;

$R_7$ is selected from the group consisting of hydrogen, hydroxy, halo, carboxyl, nitro, amino, amido, amidino, imido, cyano, sulfonyl, methanesulfonyl, and substituted or unsubstituted alkyl, alkoxy, alkylcarbonyl, arylcarbonyl, aralkylcarbonyl, alkylcarbonyloxy, arylcarbonyloxy, aralkylcarbonyloxy, alkylarninocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, alkylcarbonylamino, alkylamino-carbonylamino, arylaminocarbonylamino, aralkylcarbonylamino, aryl-carbonylamino, cyclothioamido, cycloamidino, heterocycloamidino, cycloalkyl, cycloimido, guanidinyl, aryl, arylsulfonyl and arylsulfonamido;

the tautomers thereof;
or a pharmaceutically acceptable salt thereof.

16. A compound of claim 15 wherein $R_1$, $R_2$, and $R_3$ are hydrogen and $R_4$ is selected from the group consisting of hydrogen, methyl, ethyl, aminoethyl and dimethylaminoethyl.

17. A compound of claim 15 wherein $R_1$, $R_2$, $R_3$, and $R_4$, are hydrogen.

18. A compound of claim 15 wherein $A_1$ has the formula:

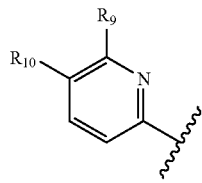

(IV)

wherein $R_9$ and $R_{10}$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkyl -aminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkyl -carbonyl, alkylthio, aryl and, aralkyl.

19. A compound of claim 15 wherein at least one of $R_5$ and $R_8$ is a substituted or unsubstituted moiety of the formula:

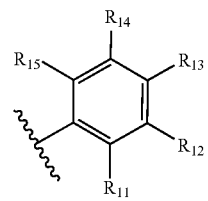

(V)

wherein $R_{11}$, $R_{12}$, $R_{13}$, $R_{14}$, and $R_{15}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkyl-carbonylamino, heteroaralkylcarhonylamino, arylcarbonylamino, heteroarylcarhonylarnino, aminocarbonyl, loweralkylaminocarbonyl, aminoaralkyl, loweralkylaminoalkyl, aryl, heteroaryl, cycloheteroalkyl, aralkyl, alkylcarbonyloxy, arylcarhonyloxy, aralkylcarbonyloxy, arylcarbonyloxyalkyl, alkylcarbonyloxyalkyl, heteroarylcarbonyloxyalkyl, aralkycarbonyl-oxyalkyl, and heteroaralkcarbonyloxyalkyl.

20. A compound of claim 19 wherein $R_{11}$, $R_{12}$, $R_{14}$ and $R_{15}$ are hydrogen and $R_{13}$ is selected from the group consisting of halo, loweralkyl, hydroxy, loweralkoxy, haloloweralkyl, aminocarbonyl, alkylaminocarbonyl and cyano.

21. A compound of claim 19 wherein $R_{11}$, $R_{13}$, and $R_{15}$ are hydrogen and $R_{12}$ and $R_{14}$ are independently selected from the group consisting of halo, loweralkyl, hydroxy, loweralkoxy, haloloweralkyl and cyano.

22. A compound of claim 19 wherein $R_{11}$, $R_{12}$, $R_{14}$, and $R_{15}$ are hydrogen and $R_{13}$ is heteroaryl.

23. A compound of claim 19 wherein $R_{11}$, $R_{12}$, $R_{14}$, and $R_{15}$ are hydrogen and $R_{13}$ is a heterocycloalkyl.

24. A compound of claim 19 wherein at least one of $R_{11}$, $R_{12}$, $R_{13}$, $R_{14}$, and $R_{15}$ are halo and the remainder of $R_{11}$, $R_{12}$, $R_{13}$, $R_{14}$, and $R_{15}$ are hydrogen.

25. A compound of claim 15 wherein at least one of $R_5$ and $R_8$ is selected from the group consisting of dichiorophenyl, difluorophenyl, trifluoromethyiphenyl, chiorofluorophenyl, bromochiorophenyl, ethyiphenyl, methyichiorophenyl, cyanophenyl and cyanochiorophenyl.

26. A compound of claim 15 wherein $R_6$ is substituted or unsubstituted aryl.

27. A compound in claim 15 wherein $R_5$ and $R_8$ are independently hydrogen or lower alkyl.

28. A compound having the structure:

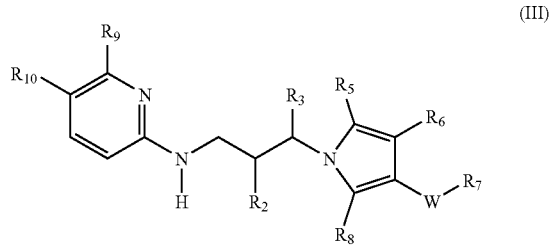

(III)

wherein W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;

$R_2$ and $R_3$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, and aryl;

$R_5$ and $R_8$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkylcarbonylamino, cycloimido, amidino, cycloamidino, guanidinyl, aryl, biaryl, and arylsulfonamido;

$R_6$ is selected from the group consisting of hydrogen; and optionally substituted aryl;

$R_7$ is selected from the group consisting of hydrogen, hydroxy, halo, carboxyl, nitro, amino, arnido, amidino, irnido, cyano, sulfonyl, methanesulfonyl, and substituted or unsubstituted alkyl, alkoxy, alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aininoaryl, alkylsulfonyl, sulfonamido, aminoalkoxy, alkylamino, alkylcarbonylarnino, alkylamino-carbonylamino, arylaminocarbonylarnino, aralkylcarbonylamino, aryl-carbonylamino, cyclothioamido, cycloamidino, heterocycloarnidino, cycloalkyl, cycloimido, guanidinyl, aryl, arylsulfonyl and arylsulfonamido;

$R_9$ and $R_{10}$ are independently selected from the group consisting of hydrogen, hydroxy, nitro, amino, cyano, halo, thioarnido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl; the tautomers thereof; or a pharmaceutically acceptable salt thereof.

29. A compound of claim 28 wherein $R_1$, $R_2$, and $R_3$ are hydrogen and $R_4$ is selected from the group consisting of hydrogen, methyl, ethyl, aminoethyl and dimethylaminoethyl.

30. A compound of claim 28 wherein $R_1$, $R_2$, $R_3$, and $R_4$, are hydrogen.

31. A compound of claim 28 wherein at least one of $R_5$ and $R_7$ is a substituted or unsubstituted moiety of the formula:

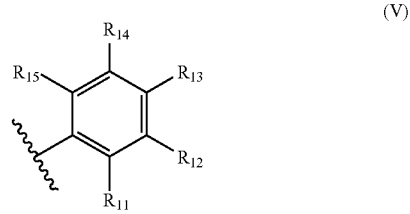

wherein $R_{11}$, $R_{12}$, $R_{13}$, $R_{14}$, and $R_{15}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkylcarbonylamino, heteroaralkylcarbonylamino, arylcarbonylamino, heteroarylcarbonyl-. amino, aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyl -oxyalkyl, and heteroaralkcarbonyloxyalkyl.

32. A compound of claim 31 wherein $R_{11}$, $R_{12}$, $R_{14}$ and $R_{15}$ are hydrogen and $R_{13}$ is selected from the group consisting of halo, loweralkyl, hydroxy, loweralkoxy, haloloweralkyl, aminocarbonyl, alkylaminocarbonyl and cyano.

33. A compound of claim 31 wherein $R_{11}$, $R_{13}$, and $R_{15}$ are hydrogen and $R_{12}$ and $R_{14}$ are independently selected from the group consisting of halo, loweralkyl, hydroxy, loweralkoxy, haloloweralkyl and cyano.

34. A compound of claim 31 wherein $R_{11}$, $R_{12}$, $R_{14}$, and $R_{15}$ are hydrogen and $R_{13}$ is heteroaryl.

35. A compound of claim 31 wherein $R_{11}$, $R_{12}$, $R_{14}$, and $R_{15}$ are hydrogen and $R_{13}$ is a heterocycloalkyl.

36. A compound of claim 31 wherein at least one of $R_{11}$, $R_{12}$, $R_{13}$, $R_{14}$, and $R_{15}$ are halo and the remainder of $R_{11}$, $R_{12}$, $R_{13}$, $R_{14}$, and $R_{15}$ are hydrogen.

37. A compound of claim 28 wherein at least one of $R_5$ and $R_8$ is selected from the group consisting of dichlorophenyl, difluorophenyl, trifluoromethyiphenyl, chiorofluorophenyl, bromochlorophenyl, ethyiphenyl, methylchlorophenyl, cyanophenyl, and cyanochlorophenyl.

38. A compound of claim 28 wherein $R_6$ is substituted or unsubstituted aryl.

39. A compound in claim 28 wherein $R_5$ and $R_8$ are independently hydrogen or lower alkyl.

40. A composition comprising an amount of a compound of claim 1 effective to inhibit GSK3 activity in a human or animal subject when administered thereto, together with a pharmaceutically acceptable carner.

41. A composition comprising an amount of a compound of claim 15 effective to inhibit GSK3 activity in a human or animal subject when administered thereto, together with a pharmaceutically acceptable carrier.

42. A composition comprising an amount of a compound of claim 28 effective to inhibit GSK3 activity in a human or animal subject when administered thereto, together with a pharmaceutically acceptable carrier.

* * * * *

UNITED STATES PATENT AND TRADEMARK OFFICE
CERTIFICATE OF CORRECTION

PATENT NO. : 7,250,443 B2  
APPLICATION NO. : 10/646625  
DATED : July 31, 2007  
INVENTOR(S) : M. C. Desai et al.

It is certified that error appears in the above-identified patent and that said Letters Patent is hereby corrected as shown below:

| COLUMN | LINE | ERROR |
|---|---|---|
| 86 (Claim 1, | 26 line 10 of text) | "heteroaryl," should read --heteroaryl, or-- |
| 86 (Claim 1, | 51 line 35 of text) | "arylamino-carbonyloxy," should read --arylaminocarbonyloxy,-- |
| 87 (Claim 5, | 15 line 4 of text) | "arnidino," should read --amidino,-- |
| 87 (Claim 5, | 15 line 4 of text) | "arnidino," should read --amidino,-- |
| 87 (Claim 5, | 16 line 5 of text) | "alkoxyarnidino," should read --alkoxyamidino,-- |
| 87 (Claim 5, | 21 line 7 of text) | "alkylamino loweralkyl," should read --alkylaminoloweralkyl,-- |
| 87 (Claim 5, | 18 line 10 of text) | "aryl and," should read --aryl, and-- |
| 87 (Claim 6, | 45 line 11 of text) | "heteroarylcarbonyl -amino," should read --heteroarylcarbonylamino,-- |
| 87 (Claim 6, | 51 line 17 of text) | "nyl-oxyalkyl," should read --nyloxyalkyl,-- |
| 87 (Claim 6, | 51 line 17 of text) | "heteroaralkearbonyloxyalkyl." should read --heteroaralkcarbonyloxyalkyl.-- |
| 88 (Claim 15, | 27 line 7 of text) | "–CHF," should read -- –CHF–,-- |

UNITED STATES PATENT AND TRADEMARK OFFICE
CERTIFICATE OF CORRECTION

PATENT NO. : 7,250,443 B2  
APPLICATION NO. : 10/646625  
DATED : July 31, 2007  
INVENTOR(S) : M. C. Desai et al.

Page 2 of 6

It is certified that error appears in the above-identified patent and that said Letters Patent is hereby corrected as shown below:

| COLUMN | LINE | ERROR |
|---|---|---|
| 88 (Claim 15, | 29 line 9 of text) | "heteroaryl," should read --heteroaryl, or-- |
| 88 (Claim 15, | 44 line 32 of text) | "cycloarnidino," should read --cycloamidino,-- |
| 88 (Claim 15, | 46 line 34 of text) | "hydrogen," should read --hydrogen-- |
| 88 (Claim 15, | 53 line 41 of text) | "alkylarninocarbony-" should read --alkylaminocarbony- -- |
| 88 (Claim 15, | 57 line 45 of text) | "alkylamino-carbonylamino," should read --alkylaminocarbonylamino,-- |
| 88 (Claim 15, | 58 line 46 of text) | "aryl-car-" should read --arylcar- -- |
| 89 (Claim 18, | 19 line 6 of text) | "loweralkyl -ami-" should read --loweralkylami- -- |
| 89 (Claim 18, | 23 line 10 of text) | "lowerhetero -carbonyl," should read --lowerheteroaralkylcarbonyl,-- |
| 89 (Claim 19, | 47 line 11 of text) | "arylalkyl-carbonylamino," should read --arylcarbonylamino,-- |
| 89 (Claim 19, | 47 line 11 of text) | "heteroaralkylcarhonylamino," should read --heteroaralkylcarbonylamino,-- |
| 89 (Claim 19, | 48 line 12 of text) | "heteroarylcarhonylarnino," should read --heteroarylcarbonylamino,-- |

UNITED STATES PATENT AND TRADEMARK OFFICE
CERTIFICATE OF CORRECTION

PATENT NO.       : 7,250,443 B2
APPLICATION NO.  : 10/646625
DATED            : July 31, 2007
INVENTOR(S)      : M. C. Desai et al.

It is certified that error appears in the above-identified patent and that said Letters Patent is hereby corrected as shown below:

| COLUMN | LINE | ERROR |
|---|---|---|
| 89 (Claim 19, | 51 line 15 of text) | "arylcarhonyloxy," should read --arylcarbonyloxy,-- |
| 89 (Claim 19, | 54 line 18 of text) | "nyl-oxyalkyl," should read --nyloxyalkyl,-- |
| 90 (Claim 25, | 5 line 2) | "dichiorophe-" should read --dichlorophe- -- |
| 90 (Claim 25, | 6 line 3) | "trifluoromethyiphenyl," should read --trifluoromethylphenyl,-- |
| 90 (Claim 25, | 6 line 3) | "chiorofluo-" should read --chlorofluo- -- |
| 90 (Claim 25, | 7 line 4) | "bromochiorophenyl," should read --bromochlorophenyl,-- |
| 90 (Claim 25, | 7 line 4) | "ethyiphenyl," should read --ethylphenyl,-- |
| 90 (Claim 25, | 7 line 4) | "methi-" should read --methyl-- |
| 90 (Claim 25, | 8 line 5) | "chiorophenyl," should read --chlorophenyl,-- |
| 90 (Claim 28, | 31 line 6 of text) | "CHF," should read -- –CHF–,-- |

UNITED STATES PATENT AND TRADEMARK OFFICE
CERTIFICATE OF CORRECTION

PATENT NO. : 7,250,443 B2
APPLICATION NO. : 10/646625
DATED : July 31, 2007
INVENTOR(S) : M. C. Desai et al.

It is certified that error appears in the above-identified patent and that said Letters Patent is hereby corrected as shown below:

| COLUMN | LINE | ERROR |
|---|---|---|
| 90 (Claim 28, | 33 line 8 of text) | "eroaryl," should read --eroaryl, or-- |
| 90 (Claim 28, | 46 line 21 of text) | "hydrogen;" should read --hydrogen,-- |
| 90 (Claim 28, | 49 line 24 of text) | "arnido," should read --amido,-- |
| 90 (Claim 28, | 50 line 25 of text) | "irnido," should read --imido,-- |
| 90 (Claim 28, | 56 line 31 of text) | "aininoaryl," should read --aminoaryl,-- |
| 90 (Claim 28, | 58 line 33 of text) | "alkylcarbonylarnino," should read --alkylcarbonylamino,-- |
| 90 (Claim 28, | 58 line 33 of text) | "alkylamino-carbonylamino," should read --alkylaminocarbonylamino,-- |
| 90 (Claim 28, | 59 line 34 of text) | "laminocarbonylarnino," should read --laminocarbonylamino,-- |
| 90 (Claim 28, | 59 line 34 of text) | "aryl-car-" should read --arylcar- -- |
| 90 (Claim 28, | 61 line 36 of text) | "cloarnidino," should read --cloamidino,-- |
| 90 (Claim 28, | 65 line 40 of text) | "thioarnido," should read --thioamido,-- |

UNITED STATES PATENT AND TRADEMARK OFFICE
CERTIFICATE OF CORRECTION

PATENT NO. : 7,250,443 B2
APPLICATION NO. : 10/646625
DATED : July 31, 2007
INVENTOR(S) : M. C. Desai et al.

It is certified that error appears in the above-identified patent and that said Letters Patent is hereby corrected as shown below:

| COLUMN | LINE | ERROR |
|---|---|---|
| 91 (Claim 28, | 4 line 45 of text) | "aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl; the tautomers thereof; or a pharmaceutically acceptable salt thereof." should read --aryl and aralkyl; the tautomers thereof; or a pharmaceutically acceptable salt thereof.-- |
| 91 (Claim 31, | 41 line 12 of text) | "heteroarylcarbonyl-. amino," should read --heteroarylcarbonylamino,-- |
| 92 (Claim 31, | 4 line 18 of text) | "nyl -oxyalkyl," should read --nyloxyalkyl,-- |
| 92 (Claim 37, | 22 line 3) | "trifluoromethyiphenyl," should read --trifluoromethylphenyl,-- |
| 92 (Claim 37, | 22 line 3) | "chiorofluo-" should read --chlorofluo- -- |
| 92 (Claim 37, | 23 line 4) | "ethyiphenyl," should read --ethylphenyl,-- |

UNITED STATES PATENT AND TRADEMARK OFFICE
CERTIFICATE OF CORRECTION

PATENT NO.         : 7,250,443 B2
APPLICATION NO.    : 10/646625
DATED              : July 31, 2007
INVENTOR(S)        : M. C. Desai et al.

It is certified that error appears in the above-identified patent and that said Letters Patent is hereby corrected as shown below:

| COLUMN | LINE | ERROR |
|---|---|---|
| 92 (Claim 40, | 33 line 4) | "carner." should read --carrier.-- |

Signed and Sealed this

Seventeenth Day of February, 2009

JOHN DOLL
*Acting Director of the United States Patent and Trademark Office*